United States Patent [19]
Riitano

[11] Patent Number: 6,059,572
[45] Date of Patent: May 9, 2000

[54] ENDODONTIC METHODS FOR THE ANATOMICAL, SECTIONAL AND PROGRESSIVE CORONO-APICAL PREPARATION OF ROOT CANALS WITH THREE SETS OF DEDICATED INSTRUMENTS

[75] Inventor: Francesco Riitano, Soverato, Italy

[73] Assignee: Ultradent Products, Inc., South Jordan, Utah

[21] Appl. No.: 09/325,035

[22] Filed: Jun. 3, 1999

Related U.S. Application Data

[63] Continuation-in-part of application No. 09/014,763, Jan. 28, 1998, which is a continuation-in-part of application No. 08/885,906, Jun. 30, 1997, Pat. No. 5,775,904, which is a continuation of application No. 08/656,988, Jun. 6, 1996, Pat. No. 5,642,998.

[51] Int. Cl.$^7$ ..................................................... A61C 5/02
[52] U.S. Cl. ............................................................. 433/224
[58] Field of Search ..................................... 433/102, 224

[56] References Cited

U.S. PATENT DOCUMENTS

| | | | |
|---|---|---|---|
| 322,265 | 7/1885 | Donaldson . | |
| 621,873 | 3/1899 | Vajna . | |
| 1,168,052 | 1/1916 | Bolls . | |
| 1,369,112 | 2/1921 | Jones . | |
| 4,231,738 | 11/1980 | Riitano et al. | 433/102 |
| 4,332,561 | 6/1982 | McSpadden | 433/102 |
| 4,353,696 | 10/1982 | Bridges | 433/125 |
| 4,364,730 | 12/1982 | Axelsson | 433/141 |
| 4,518,356 | 5/1985 | Green | 433/102 |
| 4,571,183 | 2/1986 | Nash | 433/116 |
| 4,836,780 | 6/1989 | Buchanan | 433/102 |
| 4,850,867 | 7/1989 | Senia et al. | 433/102 |
| 4,889,487 | 12/1989 | Lovaas | 433/102 |
| 4,971,556 | 11/1990 | Ritano | 433/102 |
| 4,992,048 | 2/1991 | Goof | 433/102 |
| 5,017,138 | 5/1991 | Schilder | 433/102 |
| 5,026,284 | 6/1991 | Martin | 433/102 |
| 5,219,284 | 6/1993 | Velvart et al. | 433/102 |
| 5,257,934 | 11/1993 | Cossellu | 433/102 |
| 5,498,158 | 3/1996 | Wong | 433/102 |
| 5,503,554 | 4/1996 | Schoeffel | 433/102 |
| 5,605,460 | 2/1997 | Heath et al. | 433/224 |
| 5,642,998 | 7/1997 | Riitano | 433/224 |
| 5,658,145 | 8/1997 | Maillefer et al. | 433/102 |
| 5,735,690 | 4/1998 | Malentacca | 433/102 |
| 5,752,825 | 5/1998 | Buchanan | 433/32 |

FOREIGN PATENT DOCUMENTS

| | | |
|---|---|---|
| 2597327 | 4/1986 | France . |
| 1169326 | 7/1983 | Italy . |
| 1199941 | 3/1985 | Italy . |
| 2022475 | 1/1979 | United Kingdom . |

*Primary Examiner*—Nicholas D. Lucchesi
*Attorney, Agent, or Firm*—Workman, Nydegger, Seeley

[57] ABSTRACT

A root canal is sequentially cleaned in sections from the crown to the apex by dividing it into three sections including an operative coronal portion, an operative middle portion and an apical portion. An operative phase corresponds with each section and specific instrumentation is used in each phase. After an opening is formed into the tooth to provide access into the root canal, the opening is preferably rectified to remove obstructions so that the anatomical root canal can be fully accessed. The pulp material is then sequentially removed from the portion of the root canal above the apical portion of the root canal with a set of instruments and then from the apical portion with another set of instruments. An optional set of instruments can also be used to improve the access into the apical portion such that irrigants can be delivered to the apical portion. Cleaning of the pulp material from the root canal also shapes the root canal to ease filling of the root canal with a filling material. The root canal preparation and shaping are completed while maintaining the original anatomy of the root canal. Each instrument comprises a handle connected to a file. Each file has an abrading portion and terminates at a tip. The files used to clean the portion of the root canal above the apical portion have properties which enable the abrading portion of the file to conform to the configuration of the root canal while simultaneously moving the file in a cleaning motion.

48 Claims, 32 Drawing Sheets

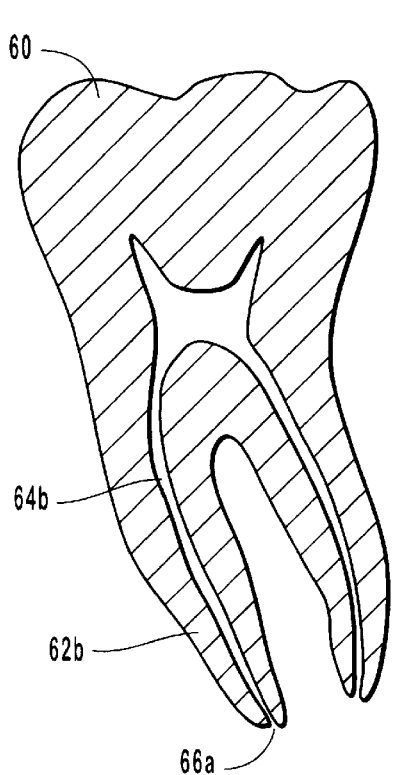
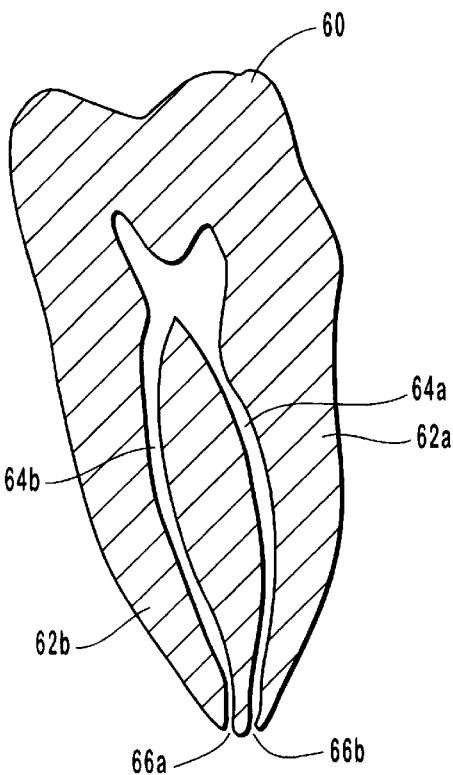
FIG. 6A  FIG. 6B
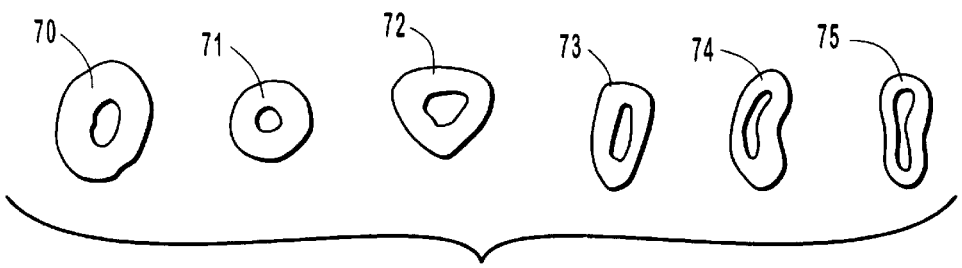
FIG. 7

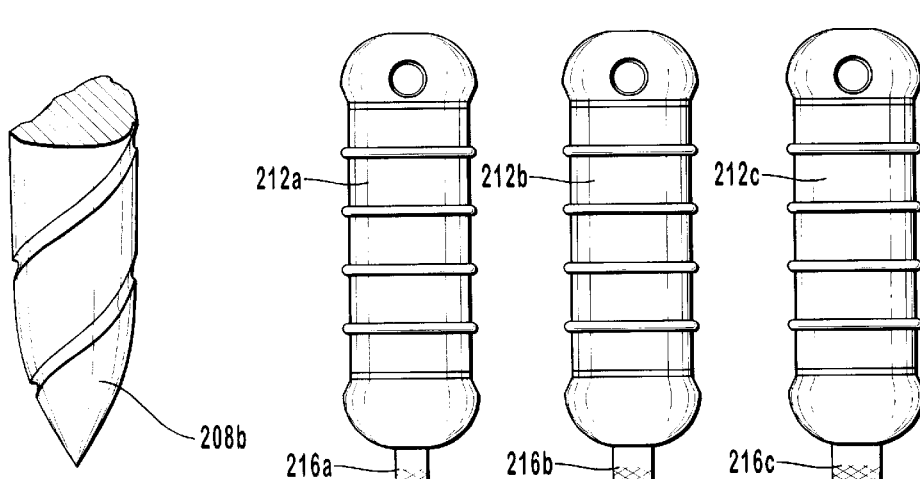
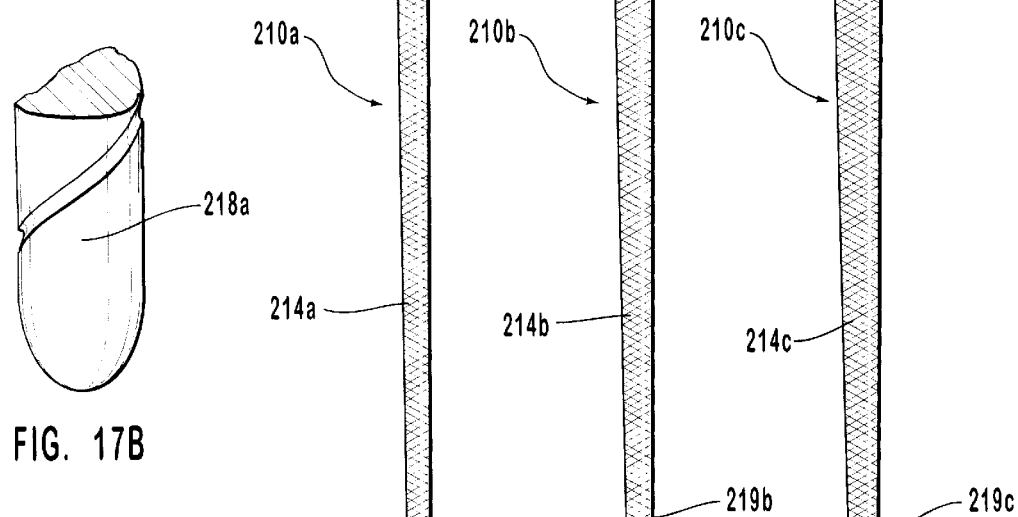
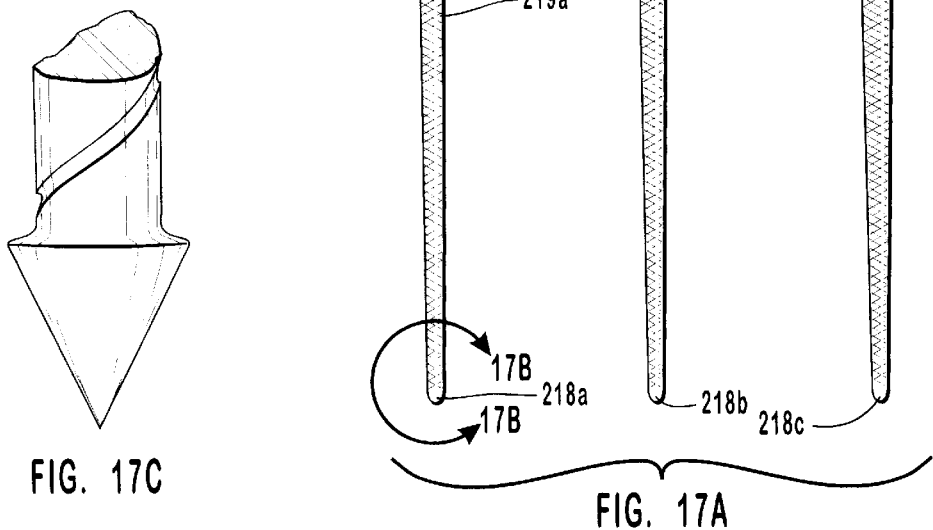
FIG. 16B
FIG. 17B
FIG. 17C
FIG. 17A

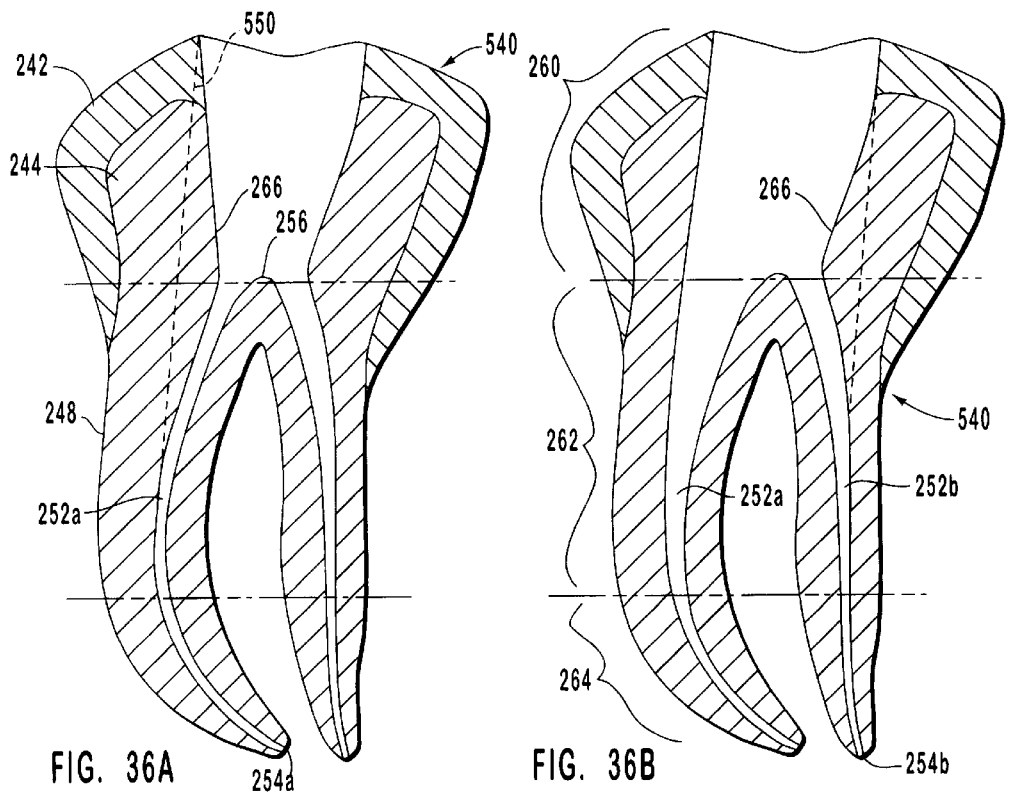

ENDODONTIC METHODS FOR THE ANATOMICAL, SECTIONAL AND PROGRESSIVE CORONO-APICAL PREPARATION OF ROOT CANALS WITH THREE SETS OF DEDICATED INSTRUMENTS

RELATED APPLICATIONS

This application is a continuation-in-part of U.S. patent application Ser. No. 09/014,763 which was filed on Jan. 28, 1998 and is entitled Endodontic Methods for Progressively, Sectionally and Anatomically Preparing Root Canals with Specific Instruments for each Section having Predetermined Working Lengths, now pending. Ser. No. 09/014,763 which is a continuation-in-part of U.S. patent application Ser. No. 08/885,906 which was filed on Jun. 30, 1997, now U.S. Pat. No. 5,775,904 which is a continuation of U.S. patent application Ser. No. 08/656,988 filed Jun. 6, 1996, which issued on Jul. 1, 1997 as U.S. Pat. No. 5,642,998. Priority of U.S. Pat. No. 5,642,998 is based on Italian Patent Application No. RM95A000377 which was filed on Jun. 6, 1995. For purposes of disclosure of the present invention, each of the foregoing applications is incorporated herein by specific reference.

BACKGROUND OF THE INVENTION

1. The Field of the Invention

The present invention is related to the field of endodontistry. More particularly, the invention is related to systems and operating methods for the preparation of root canals for obturation. The systems and methods involve the use of instruments which are dedicated for specific purposes in the inventive methods and systems.

2. The Relevant Technology

To preserve a tooth with a pulp that is diseased or is potentially diseased, it is generally necessary to remove as much of the pulp material as is possible from the pulp canal of the tooth, to shape the root canal(s) without excessively weakening the root canal walls, to prevent or minimize the presence of bacteria through the use of irrigants and dressings, and lastly, to clean the walls of the root canal(s) by removing the smear layer created during instrumentation of the root canal(s). These steps are all done to prepare the root cavity for sealing or obturation which involves filling the root canal with biocompatible materials, such as gutta percha, before the pulp cavity is sealed, thereby promoting the healing and functional recovery of the tooth. This procedure is referred to as root canal therapy.

As indicated hereinabove, root canal preparation involves pulp removal, cleaning of the root canal walls and shaping of the canal walls. This is typically achieved through a guided procedure with the use of instruments which are moved either manually, mechanically or by combinations thereof. These instruments are files or bits that are configured to bore and/or cut. Mechanical instrumentation can be achieved through the use of endodontic handpieces coupled to instruments such as files. The endodontic handpieces can impart rotational motion to a file, reciprocal motion by alternately rotating a file clockwise and counterclockwise, sonic movements or ultrasonic movements.

Before endodontic therapy is begun, a preoperative x-ray image is obtained to assess the health and the pathological status of the tooth and to determine the approximate initial length of the root canal(s). Once the approximate length of the root canal(s) has been determined, an instrument can be selected for use in the root canal which has an appropriate working length.

The schematic representations shown in FIGS. 1A and 1B are similar to a typical x-ray image. As shown in FIGS. 1A and 1B, an x-ray image of teeth generally show teeth with sufficient clarity to view some of the properties of roots 12 and the root canals 14 located therein, particularly the location of the radiographic apex 17. The location of the radiographic apex often does not coincide with the true apical terminus of the canal just beyond the apical foramen 16. The distance between radiographic apex 17 and a fixed reference position on the occlusal surface of a tooth is used to determine the working length of the instruments. FIG. 1B, which is an enlarged view of root 12a shown in FIG. 1A, shows the relative position of the radiographic apex designated at line 17 in relation to that of the endodontic apex and the anatomical apex designated respectively by lines 18 and 19. This condition is typical of an apex in living teeth, whereas a pathological apex can appear in a partially autolyzed state, as shown in FIG. 34C.

Preoperative or intraoperative x-ray images of a tooth requiring endodontic treatment, such as the x-ray image depicted in FIG. 1A. are obtained by lingual placement of film packets as shown in FIG. 2 at 22 which is supported by an x-ray film packet holder (not shown) and a long cone x-ray head (not shown) located outside of the cheek. Although, x-ray images obtained as shown in FIG. 2 from a buccal-lingual x-ray projection are generally useful for determining the overall characteristics of a tooth, the approximate initial length of the root canal(s), and the working length for a file, such images provide only limited information regarding the overall anatomy of the root canal.

The information is limited because only one dimension of the overall anatomy of the pulp cavity can be viewed in vivo. In the standard buccal-lingual projection such images show only a linear profile of the root canal and cannot show a tridimensional view of a tooth and its root canal(s). Although, it would be very helpful to view a tooth from a position between the teeth or from the interproximal space such a mesial-distal view cannot be clearly produced when the tooth is still positioned in a patient's mouth. Since information is need of all three dimensions in order to correctly understand the overall anatomy of the root canal and yet only two-dimensional images of a tooth can be obtained, x-ray images are sometimes relied on to reach incorrect conclusions regarding the anatomy of the root canal. More particularly, if not properly evaluated, x-ray images can be misleading as to the actual length of the root canal and the position of the foramen or foramina.

The difficulties encountered by an endodontist in assessing the overall anatomy of teeth from just the x-ray images obtained from buccal-lingual x-ray projections can be clearly identified with reference to FIGS. 3–6. FIGS. 3A–6A are longitudinal cross-sectional schematic views of extracted teeth taken from the front or back of the respective tooth which correspond with typical images obtained from buccal-lingual x-ray projections. FIGS. 3B–6B are longitudinal cross-sectional schematic views of the same extracted teeth shown respectively in FIGS. 3A–6A taken from the mesial-distal or side view that cannot be obtained or seen while the teeth are still positioned in a patient's mouth.

Note that by varying the angle of incidence of the x-ray beam mesiodistally and distomesially additional x-ray images can be made which provide some additional information about the anatomy of the tooth. However, we can never obtain a three-dimensional image!

FIGS. 3–4 illustrate that in order to properly prepare a root canal it is necessary for practitioners to rely heavily on their experience, knowledge acquired through a stud, of typical anatomical structures, and on their visually acquired experience with longitudinal and transverse dental cross-sections at various heights. FIG. 3A depicts a lower premolar 30 from the buccal-lingual view of the tooth which shows root 32 and a root canal 34 therein that appears to be rather narrow and to have a relatively uniform perimeter along its length. FIG. 3B, however, shows that when seen from the mesial-distal view, the root canal is initially fairly wide over more than half its length, and then tapers significantly before reaching the apical foramen 36. Comparing FIG. 3A with FIG. 3B clearly shows that when limited to knowledge derived from an x-ray corresponding to the image shown in FIG. 3A, the practitioner may not be able to accurately assess the anatomical structure of the root anatomy. Additionally, FIG. 3C shows that instead of an apical foramen there may be double, triple or quadruple foramina as indicated in research performed by the applicant and by others. The triple foramina 36a, 36b and 36c shown in FIG. 3C may not be detectable when viewed only from the buccal-lingual view shown in FIG. 3A.

FIG. 4B depicts an upper premolar 40 with roots 42a and 42b and root canals 44a and 44b located therein. Comparing FIG. 4A and FIG. 4B reveals a problem which is similar to the problem revealed by comparing FIG. 3A with FIG. 3B. More particularly, by comparing FIG. 3A with FIG. 3B or FIG. 4A with FIG. 4B, it is easily understood that the practitioner may not be able to accurately assess the anatomical structure of the root anatomy when limited to knowledge derived from an x-ray image. Since the configuration of pulp chamber 48 may be difficult to accurately and fully ascertain from only an x-ray image, a practitioners also relies, as indicated hereinabove, on accumulated experience, knowledge of dental anatomy, and knowledge of typical anatomical structures.

The potential inaccuracy of a conclusion derived from information obtained from an x-ray image is further illustrated by comparing FIG. 5A and FIG. 5B and also FIG. 6A with FIG. 6B. More particularly, as discussed hereinbelow, FIGS. 5–6 show that practitioners encounter anatomies with widely varying aberrations and intercommunications of root canals which may not be apparent to the practitioner from the limited information derived from x-ray images.

FIG. 5A depicts a mandibular or lower incisor 50 from the buccal-lingual view of the tooth which shows root 52 and root canal 54. FIG. 5B depicts the same lower incisor 50 from the mesial-distal view of the tooth. The mesial-distal view shows in FIG. 5B clearly reveals that root canal 54 branches and then rejoins to have a single foramen 56. Root canal morphological variations, such as that shown in FIG. 5B, may not be detectable by a practitioner who relies solely on a preoperative or intraoperative x-ray image, such as the image of lower incisor 50 shown in FIG. 5A.

Similarly, a root canal may branch without merging so as to yield multiple foramina, such as the root canal of a lower first molar 60 shown in FIGS. 6A–6B. Again, the buccal-lingual view, as shown in FIG. 6A, provides inadequate information when compared with the depiction taken from the mesial-distal view of mesial root 62b in FIG. 6B. FIG. 6B reveals that branches 64a and 64b do not merge and accordingly have two foramina 66a and 66b.

In addition to the morphological variations in anatomy as discussed above, consideration should also be given to the substantially different perimetrical configurations of root canals, as revealed by various dental cross-sections shown in FIG. 7 and FIG. 8. Additionally, the shape of root canal perimeters varies not only between different types of teeth as shown in FIG. 7 and FIG. 8 but also along the length of a single root canal of a tooth as is illustrated in FIGS. 9A–9B.

FIG. 7 shows a classification system devised by A. Latrou which divides the perimetrical anatomies of root canals into those that have primarily a tubular morphology and those that have primarily a laminar morphology. Examples of root canals with tubular perimetrical anatomies are shown at 70, 71, and 72 which are respectively primarily oval, round and triangular. The laminar perimetrical anatomies include root canals with essentially slit-like configurations such as those shown at 73, 74, and 75 which are respectively primarily straight, semi-lunar shaped and figure eight shaped as it has vestibular and lingual bulges. The laminar shape is more common than the tubular type root canals.

FIG. 8 shows cross-sectional views of the middle third of different teeth 80a–80l that have been extracted and then cut along a transverse cross-section of the tooth to show root canals 82a–82l as well as corresponding pulp chambers 84 and floors or cervical aspects 86. Conventional file instruments 88 are also shown inserted into root canals 82. From this view, which can only be seen in vitro, it is evident that a certain degree of variation occurs in the perimetrical anatomy of the pulp cavity of teeth. The practitioner may at first be unaware of such variation; however, the practitioner must keep in mind the possibility of such variation while working with instruments in the root canal so that all of the canal walls will be treated and the irregularities caused by greater parietal thicknesses can be removed without unduly weakening the walls.

FIG. 9A depicts a maxillary right upper first molar 90 with dashed cutting lines included to identify the division of the tooth into transverse cross-sections for segmentation as shown in FIG. 9B. FIG. 9B displays roots, 92a, 92b and 92c of molar 90 as cut into four respective segments, 100–103, to clearly show the variations of root canals 94a, 94b and 94c. Also displayed in FIG. 9B are segments 104 and 105, which respectively contain the pulp chamber 98 and its floor. A comparison of the perimeters of root canals 94a, 94b and 94c starting at segment 104 as each root canal tapers to its respective apices 96a, 96b and 96c, clearly shows that the perimeter anatomy varies and transitions in configuration along the entire length of each root canal. So not only must a practitioner deal with root canals having different shapes as discussed in reference to FIG. 7 and FIG. 8, but the practitioner must also utilize an instrument in a root canal with a perimetrical or circumferential anatomy that varies depending on the height at which the observation is made.

From the discussion above, it is apparent that when a practitioner views a preoperative or interoperative x-ray image of a tooth, the practitioner can only guess about the actual anatomy of the pulp cavity and the root canal(s) of the tooth. While the practitioner may be able to confirm that a root canal has been cleaned along the length of the pulp chamber from the coronal portion to the apex of the root, the length that has been contacted or abraded by the file may only be a portion of the root canal system.

Since it is impossible to obtain a mesial-distal view of the root canal or to view the perimetrical anatomy on different points along the length of the root canal, the practitioner is prevented from obtaining a proper preliminary understanding of the overall root canal anatomy in order to assess the necessary relationship between the canal walls and the instrument inserted in the root canal. Accordingly, as shown in FIG. 10A and FIG. 10B, when a file instrument such as instrument 114 is inserted as far as the apex into a root canal such as canal 112a of tooth 110a or canal 112b of tooth 110b and then rotated, significant portions are not cleaned.

The inability to clean all surfaces of a root canal by merely inserting and rotating a file instrument in a root canal is further illustrated by FIG. 8. FIG. 8 depicts the position of file instrument 88 in transverse cross-sectional views of root canals after file instrument 88 has been inserted to the apex of each respective root canal. FIG. 8 clearly shows that simply drilling from one position into the root canal will often miss large sections of the perimeter of the root canal, thereby leaving portions of live, diseased or necrotic pulp material undisturbed. If the operator is unable to apply the instrument to every segment of the perimeter of the canal, the undisturbed pulp material may ultimately cause undue pain, lengthy healing times or even cause the procedure to fail.

To compensate for the failure to adequately clean the entire root canal, solvents such as sodium hypochlorite are used to contact the recesses in the anatomy of the canal. Such solvents are particularly relied on to contact the apical recesses that cannot be reached with the instruments and that may even be full of necrotic tissue. Some practitioners even leave the sodium hypochlorite in place to act on the canals for an extended period of time.

The next step is neutralization or obturation of the root canal which involves coating or filling the root canal with a plastic obturation material such as heated gutta percha. The object of obturation is to prevent the ingress of bacteria or tissue fluids which might act as a culture medium for any bacteria remaining within the root canal system by sealing the system. In order to reach the recesses with filling material that cannot be treated with the instruments, vertical pressure must be applied with a plugger; however, there is never any assurance that all of the necrotic residue has been coated. There is also a risk that such techniques will cause infected material to be pressed beyond the apex. Such an extrusion of infected material beyond the apex is very undesirable as it may contain polymicrobial loads or charges that may produce damaging bacteremia or cause chronic inflammations of the apical and periapical tissues.

Based on all of the foregoing observations, it can be concluded that inadequate attention is given to understanding the dental chambers on a three-dimensional basis, the varying configurations of the perimeter of the root canal(s), the diameter of the canals, and the thickness of the walls. Note that research is still needed to investigate and catalog the thickness of dental walls in order to increase understanding amongst practitioners.

The inability to fully identify the anatomy of the pulp cavity restricts the ability of the practitioner to confidently conclude that the procedure has been successful. Although problems may result from having incomplete information regarding the anatomy of a particular root canal, many practitioners using conventional methods and instruments are not overly concerned with completely cleaning the entire root canal since their failure rate is not at an unsatisfactory level. While these conventional methods and instruments may result in satisfactory failure rates, it would be very beneficial to still lower the failure rate and to better preserve the integrity of teeth.

As discussed hereinbelow, most of the methods and instruments that have been and continue to be employed and produced are relatively arbitrary with regard to root canal anatomy. To compensate for the limited understanding of the inability to contact all root surfaces and the lack of knowledge of the actual anatomy of the root canal, many working methods have been devised, which in turn have prompted the creation of a multitude of instruments of varying diameters and sizes.

With regard to operating procedures, there are two basic methods from which all of the canal-preparation techniques can be derived. These methods have been interpreted by various authors in an operational context and also in terms of the instrumentation. The primary conventional systems and methods for removing pulp material from the root canal of a tooth are the apico-coronal (step-back) technique and the corono-apical (crown-down) technique. Although these conventional cleaning techniques both rely generally on sequential increases in the diameter of instruments inserted into the root canal, the step-back technique involves cleaning the root canal from the apex toward the crows while the crown-down technique involves cleaning the root canal from the crown down to the apex. Each has its own unique benefits and disadvantages which are discussed hereinbelow.

The step-back technique involves the use of various sets of file instruments which are sequentially inserted into a root canal after the root canal has been exposed by removing the roof of the pulp chamber as depicted in FIG. 11A and FIG. 11B. More particularly, before pulp material 160 can be removed in accordance with the step-back technique, an instrument, such as instrument 120 shown with bur 122 in FIG. 11A and FIG. 11B, is utilized to remove the overhanging portions of enamel 152 and dentin 154 in order to provide access into the pulp chamber 156. FIG. 12 depicts a set of step-back file instruments with each file instrument 130 comprising a handle 132 connected to a file 134 or a shaft with tines or an abrading portion. Each file has a tip 136 opposite a top end 138 where file 134 joins handle 132. As viewed in FIG. 12 from left to right, the diameter at top end 138 of each file increases progressively from the smallest to the largest such that the diameter of 138a is less than the diameter of 138b. The diameter of each successive file at tip end 136 is also successively larger. Accordingly, the taper of each file remains essentially the same even though each file is progressively larger that the preceding file.

In the step-back technique, the apical portion of the tooth is prepared first and then the remainder of the canal is flared from apex to crown. This process essentially involves inserting a series of progressively larger files into the apex of the root canal and rotating each file and/or moving the file up and down in a longitudinal motion until a file can be inserted that is considered to be a suitable standard size for completing the process or that meets some resistance to rotation. The rest of the canal is then flared by sequentially using each file in the set, as shown in FIG. 12, with each file being larger than the preceding file and by alternately advancing and then withdrawing each instrument.

FIG. 13A depicts a molar 150 being prepared by the step-back technique after the removal of enamel 152 and dentin 154 that extend into pulp chamber 156, and after the first stage of the step-back technique has been completed. The first stage of the step-back technique involves the insertion of a file into pulp chamber 156 and into root canal 158a in order to remove material 160 in the lower portion of the canal above the apex or apical end 162a. After the portion above apex 162a is cleaned, each file shown in FIG. 12 is sequentially inserted downward toward apical end 162a of root canal 158a, starting with file instrument 130a as shown in FIG. 13A. As a result of this technique, the diameter of the area being contacted at the apical portion is increasingly larger.

FIG. 13B is a cross-sectional view taken along cutting line 13B—13B in FIG. 13A of tooth 150 during cleaning of root canal 158a with file instrument 130a in the step-back technique. Insertion of the files of the other file instruments 130b and 130c may further clean out material 160 because each file has an increasingly larger diameter. With each increase in diameter the rigidity increases and the flexibility of the files decreases. As a result, it becomes increasingly difficult for the files to adjust to or to follow the contours of the perimeter surfaces of the root canal. This reduced flexibility also increases the likelihood that the files will fail to contact some portions while removing too much of the surrounding dentin 154 in some areas through excessive abrasion and resulting in overthinning of the walls.

Note that the views depicted in FIGS. 13A and 13B depict the problem previously discussed with regard to the difficulty in assessing the actual root canal anatomy in vivo. When viewed in FIG. 13A, it appears that the root canal has been cleaned; however, FIG. 13B shows that a significant portion of material 160 remains. Accordingly, when the root canal is viewed in an x-ray photograph which is the same view shown in FIG. 13A, a practitioner may mistakenly believe that the tooth has been adequately cleaned. This mistaken belief may be further incorrectly relied on as the root canal is widened by the insertion of the larger files which gives an impression of complete cleaning. There is resultingly some possibility for failure of the root canal therapy due to incompleteness.

Not only is the completeness effected by the use of a set of files wherein each file is more rigid than the preceding file but the ability to safely move the file within the canal is also limited. More particularly, the increasing rigidity results in decreased ability to negotiate the curves in the canal. Significant problems that can result from inserting increasingly rigid files and also from initially inserting a file all the way down to the apex includes laceration and transportation of the apical foramen, as well as misdirection and perforation of the wall. As shown in FIG. 14A, after tooth 170 was prepared by removal of portions of the enamel 172 and dentin 174, file 132 was inserted into root canal 176 and perforated apex 178. Perforating the apex can also result from an error in estimating the length of a root canal, by failure of a stop such as stop 140 to remain at a predetermined position or by failure to observe the calibration or graduation hatch markings on the file, which can be used instead of a stop to designate the length.

The apex can be perforated by extrusion of the infected material 180 through the apex due to the force exerted by the file on the material as the file is pushed downward to reach the apex. As a result, the periapical region can be invaded and contaminated. The potential for extruding infected material through the apical foramen of a necrotic tooth during the initial insertion of a file instrument all the way down to the apex is a particular disadvantage of the step-back technique. Another disadvantage is that the procedure has identical steps for working in either necrotic or vital root canals. In addition to exposing the tissue surrounding the tooth to the infected material, apical perforations may allow irrigants, amalgam filling or obturating material to flow out of the apex. Such apical perforations, as well as wall perforations, may delay tooth healing and may compromise the outcome of the therapy.

Perforations can also occur due to a failure to maintain a proper working length of the instrument during the procedure. As the canal is widened, curvatures are straightened thereby decreasing the required working length needed for the instrument to work. Accordingly, the rubber stop 140 must be adjusted, thereby continually providing an opportunity for the instruments to become contaminated by bacteria. To properly determine the appropriate working length, many radiographs must be taken throughout the operation as the canal is continuously being modified, which alters the length. The time required to obtain the x-ray photographs or images and to adjust the working length of the instruments by repositioning the stops can result in a lengthy process. The step-back technique is also time intensive because a large number of instruments are required to complete the root canal therapy.

As shown in FIG. 14B, another problem is the formation of ledges such as ledge 182. Ledges can occur when a practitioner attempts to insert a file such as file 134 as far as the apex and the file is too inflexible to properly curve with the root canal or move around a protrusion. When a file is too inflexible to curve or flex as needed and is halted prematurely, the downward pressure exerted on the file, in conjunction with the tendency of the file to straighten itself, causes the tip of the file to dig into the side of the root canal and form a ledge. Such ledges are difficult to bypass, and if the ledge occurs very close to the apex, the ledge may give the practitioner the mistaken impression that the apex has been reached.

The crown-down technique was developed for several reasons. It was desired to shape the canal "conically" so as to keep the diameter of the foramen as straight as possible. The crown-down technique was also developed to prevent the discharge of septic material or obturation material from the apex after the initial canal-preparation step and to prevent subsequent vertical condensation due to the vertical pressure used to obturate the canals with heated gutta-percha. Additionally, the crown-down technique was intended to reduce the number of instruments utilized compared with the step-back technique. However, as discussed hereinbelow, significant potential problems may inherently result from use of the crown-down technique.

The crown-down technique generally involves the use of a set of file instruments wherein each file in the set of file instruments has a progressively different diameter at the top of the cutting portion of the file, i.e., the point where the file becomes smooth and no longer has cutting capabilities. The smooth portion may have a constant diameter. The diameter at the top of the cutting portion of each file may be either constant or graduated for the entire set of instruments such that the top of the cutting portion of each file is progressively larger than that of the preceding file. As a result of this configuration, the taper of each file is larger than the preceding file in the set. By using such files of increasingly larger diameters, the area that is initially and subsequently abraded, as work proceeds toward the apex, will always be primarily at the top portion of the root canal.

Gradual progressive conicity or taper, and the constant diameter of the tip (characteristics which, paradoxically, have been inflated, despite the prior teachings of the present applicant in earlier patents, such as Italian patents No. 1,199,941 and No. 1,169,326, and U.S. Pat. No. 4,971,556) are characteristics which are now so standard among the multitude of crown-down instruments made of nickel/titanium that have been introduced onto the market, that competitors have shifted toward other features of the instruments. For example, increasing value is being attached to the so-called "overall" originality of an operating procedure that uses so-called "dedicated" instrumentation to solve the multiple problems associated with root canal preparation in terms of ergonomics, operational safety, the time and cost of the procedure, and the likelihood of success.

One example of the operational deficiency of the crown-down method lies in its association with instruments made of nickel/titanium. Based on the greater flexibility of files formed from nickel/titanium compared with files formed from steel, proponents of the crown-down method in conjunction with nickel/titanium files assert that such files can better follow the curvatures of a root canal. Additionally, it has been asserted that such files are more likely to stay in the center of the root canal, thereby decreasing the likelihood of ledging or perforating the root canal walls. As set forth hereinbelow in greater detail, each material has its own unique advantages and disadvantages.

The ability of a nickel/titanium file to stay in the center is not necessarily desirable, in view of the morphology and perimetrical variety of root canals, and particularly the variety in the upper two-thirds of laminar root canals. In fact when rotation is imparted to an instrument that stays in the center of the canal, the file instrument works simultaneously and indiscriminately on all of the walls within reach of the file. Since root canal walls do not have equal thicknesses in all directions and at all different points along a root canal, some walls can be overthinned or perforated, while other walls remain untouched.

Moreover, because nickel/titanium files are more flexible than steel files, they tend to follow the path of least resistance and therefore cannot be used, in the same way as steel files, to be applied actively and intentionally by the operator. As a result, even when the operator knows the thickness of a particular portion, such as an interference or obstruction which the operator desires to rectify or straighten, the operator lacks the freedom to aggressively drive the file as needed and clean the portions that are difficult to reach. Accordingly, when a nickel/titanium file is used to clean a non-cylindrically shaped root canal the file moves only at the center of the canal and/or the area of least resistance and fails to remove all of the necrotic tissue.

FIGS. 15A, 15B, 15C, 15D and 15E depict transverse cross-sections of tooth 190 that has been cleaned in a manner that has resulted in either overthinning of root canal walls, perforation of a root canal wall, excessively weakening of the walls of the tooth or a failure to fully contact all of the canal walls. These problems can be easily caused by the passive, self-guiding use of nickel/titanium files with progressively larger tapers in the transition from the first instrument to the next one in the set, and increasing rigidity in accordance with the crown-down technique which prevents the tiles from being laterally moved to enable the files to clean the entire perimeter of the root canal. The cross-sections shown in FIGS. 15A–E may be considered independently from each other as being cross-sections from different teeth or from a single tooth such that FIG. 15A shows two roots 192a and 192b of a tooth 190 while FIGS. 15B–15E show root canal 194a as the root canal tapers to the apex.

FIG. 15A depicts the overthinning that can occur to the furcation walls of root canals 194a and 194b near the bifurcation as a result from the indiscriminate thinning of the distal walls of the root canals by maintaining a file instrument in a central location during working rotation. The resulting boreholes are shown at 196a and 196b while the outlines of root canals 194a and 194b before cleaning are shown in phantom lines. Such overthinning and potential furcal perforation can have devastating results. The inability to adequately direct a file used in accordance with the crown-down technique based on the practitioner's knowledge of the relative thicknesses of the portions of canal walls is a significant disadvantage of the technique.

FIG. 15B shows a lateral perforation that has occurred when a hole was made through dentin 198 and cementum 197 during the cleaning of root canal 194a. The lateral perforation resulting from the formation of borehole 196a may be obscured from the x-ray due to concavities or curvatures in the root canal. The practitioner may then mistakenly conclude that the root canal has been successfully cleaned without realizing that there is a perforation.

In FIG. 15C, the segment shown of root canal 194a was overly thinned during the cleaning of root canal 194a as borehole 196a is shown extending through dentin 198 and into the cementum 197. As mentioned in reference to FIG. 15B, the formation of borehole 196a may be obscured from the x-ray view. As a result, the practitioner may not realize that the borehole extends into the cementum and may therefore mistakenly conclude that the root canal treatment has been successful. Infective bacteria that remained in the root canal, perhaps in the portions that were not contacted with the files, as well as toxins produced by the bacteria may then permeate through the cementum and cause infection or other complications.

FIG. 15D provides an example of a cross-section of a laminar-type root canal cleaned by the crown-down technique which may result in successful root canal therapy since the instrumentation has not resulted in a perforation and the cementum 197 has not been exposed. Although, problems such as perforations or overthinning have been avoided, FIG. 15D shows that large portions of root canal 194a remain untouched despite the change in morphology through the formation of large borehole 196a. Note that the change in the morphology of the canal shown in FIG. 15D resulting from crown-down technique instrumentation occurs due to drilling in a passive, circular manner with instruments having gradual and progressive tapers. The failure to contact significant portions of a root canal while forming a large borehole in a root canal as shown in FIG. 15B–D is a very typical result of the crown-down technique since most root canals can be characterized as a laminar-type root canal.

It would be preferable to avoid the risk posed by failing to contact significant portions of the root canal as shown in FIG. 15D. Since the practitioner is prevented from removing and cleaning essentially all pulp material, the practitioner cannot be assured of the reliability of the treatment. Additionally, the practitioner may not suspect that the working instruments have failed to contact every segment of the root canal as use of a set of files, with increasingly greater tapers can contribute to a potentially incorrect conclusion that cleaning by such a conventional process has resulted in removing all material from root canal 194a. Further, the x-ray view of tooth 190, as with the step-back technique shown in progress in FIGS. 13A and 13B, would give the impression that the root canal had been cleaned. It should also be remembered that while rotation of a set of passively actuated files, with increasingly greater tapers, in the center of the canal, in accordance with the crown-down technique, may yield a configuration as shown in FIG. 15D and result in successful root canal therapy, there is a significant hazard, as shown in relation to the FIGS. 15A–C, due to the passivity of the instruments when linked to canal diameters and wall thicknesses that are still statistically unknown.

As in the configuration shown in FIG. 15D. the configuration shown in FIG. 15E may also result in successful root canal therapy—but only for canals of the wholly tubular type. Although, borehole 196a does not extend through dentin 198 and into the cementum 197, the diameter of the preparation or borehole 196a is nevertheless significantly larger than that of the original root canal was as shown by the phantom lines at 194a. The excessive thinning of the dental wall may resultingly significantly weaken the resistance of the walls to the stress of chewing, and may also cause a fracture of the root.

From the above discussion in relation to FIGS. 15A–E, it is clear that the actual morphology of the canals is not sufficiently considered when using this method and that the use of files with increasingly larger tapers limits the range of motion of the files. More specifically, due to the use of files with successively larger tapers which therefore are increasingly rigid, each file, if actuated passively, is primarily limited to being rotated without substantial lateral movements guided by the operator. Since the majority of files are of the laminar type, this limitation poses a significant problem. Without the ability to laterally move the files, it is not possible to make contact with every segment of the perimeter of the canal and some portions may receive too much contact.

In any event, if the files are rotated passively in a laminar canal or a canal which has a laminar-type anatomy for the first two-thirds of the canal, the result is a circular opening whose diameter corresponds to that of the file that was used. The file typically stays in the center of the canal during rotation, such that the tip of each file acts like a fulcrum and "ideally" stays in the same position as a rotation point. Since each successive file can move less laterally, each file simply makes a big(ger borehole than the preceding file. Accordingly, the files cannot clean a root canal without significantly altering the original anatomy by leaving a footprint or borehole corresponding to the configuration of the instruments used. More specifically, the result is a footprint or borehole with a perimeter that corresponds to the perimeter of the biggest tile that extends well beyond the original anatomy of the root canal and yet in most instances does not adequately clean significant portions of the root canal.

As discussed above, the flexibility of the files used in the crown-down technique, which are typically formed from nickel/titanium, prevents the files from being successfully urged against the perimeter or against the various surface features of the root canal. As also discussed above, the flexibility of the files also increases the tendency of the files to remain in the center or at the location where less resistance to movement is encountered. Accordingly, the flexibility of the files also contributes to the configuration of borehole 196a which substantially deviates from the original anatomy of the root canal 194a.

There are also other disadvantages to the use of nickel/titanium files. The flexibility of nickel/titanium files increases the likelihood that the file may bend and be deformed upon encountering a hard substance. Since nickel/titanium files are more fragile and more flexible than stainless steel files, the nickel/titanium files can break more easily and unexpectedly than steel files. When a nickel/titanium file instrument is used with a large file diameter the flexibility decreases to the point of being as rigid as stainless steel and yet breaks more easily. More particularly, beyond a certain diameter, the upper halves of larger diameter files are still as rigid as that of steel files while the flexible lower halves of nickel/titanium file instruments are more prone to break.

Additionally, rotation of a file in a canal that has a laminar upper two-thirds exposes the tip of the file to the risk of breaking when the tip of the file is embedded or stuck in a canal whose diameter is smaller than its own diameter! To avoid breaking the tip when it is embedded or stuck in a canal whose diameter is smaller than the diameter of the tip, operators who use nickel/titanium files are advised to employ catheterization in order to obtain a prophylactic widening of the canal, using a series of instruments with increasingly larger tip diameters.

Another disadvantage of nickel/titanium files is that nickel embodied in the alloy may potentially result in an allergic reaction. Further, nickel/titanium files costs about four times as much as steel files and yet nickel/titanium files generally wear out faster than steel files. Nickel/titanium files wear out so quickly that some manufacturers mark their products as being intended for single use only.

Moreover, the crown-down instruments currently available on the market, almost all of which are made of nickcel/titanium, in some respects violently conflict with the use of the crown-down method, because, paradoxically, these instruments are smooth in areas where the method requires that they first perform a cutting action. The reason for this deficiency lies in the length of the abrading portion of the instruments, which portion is only 16 mm long and which extends into a smooth portion leading to the handle, onto which rubber stops are affixed, or into which millimeter-based calibration marks are engraved in order to allow visual control of the working depth of the instrument in the canal. For example, note in FIGS. 13A and 13B that when file 134a is inserted into root canal 162a that the abrading portion 138a is not long enough to contact the dentinal shelves 166, instead the upper portion of the file is smooth shank portion 136a. Since the length of the root canal often exceeds the standard 16 mm length abrading portion of conventional instruments, see Table 1 hereinbelow, we may reasonably ask how an instrument which, according to the crown-down method, is supposed to prepare a canal starting at its coronal third, can perform this task if its coronal segment is smooth!

TABLE 1

Average Root Canal Lengths

| Tooth | Upper | Lower |
| --- | --- | --- |
| Central | 23 mm | 20.5 mm |
| Lateral | 22 mm | 21 mm |
| Canine | 26.5 mm | 25.5 mm |
| First Premolar | 20.5 mm | 20.5 mm |
| Second Premolar | 21.5 mm | 22 mm |
| First Molar | 20.5 mm | 21 mm |
| Second Molar | 20 mm | 20 mm |

Obviously, from a review of the average root canal lengths in Table 1, significant segments of a root canal cannot be abraded by standard 16 mm long abrading portions of conventional files and are contacted only by the smooth portion of the files.

Although, the crown-down technique typically enables a practitioner to more efficiently clean a root canal than the step-back technique they both require the practitioner to utilize many different instruments. The need to frequently change the cleaning instrument results in significant time requirements for cleaning a root canal. However, careful instrumentation in accordance with either tedious time consuming method does not avoid the problems set forth above in relation to apical perforation, wall perforation, overthinning or failure to clean all of the wall surfaces.

Based on the foregoing observations, methods and systems are needed in the endodontic arts which enable a dental practitioner to remove and clean essentially all pulp material in a root canal requiring root canal therapy.

It would also be an advancement in the endodontic arts to provide methods and systems that are based on the three-dimensional reality of teeth and do not relate solely to buccolingual x-ray views, thereby enabling a practitioner to remove and clean pulp material in a root canal without compromising the strength of the walls and the apical anatomy.

It would also be a beneficial development in the endodontic arts to provide methods and systems which encourage perimetrical contact of the instruments with the canal walls.

Additionally, it would be an advancement in the endodontic arts to provide methods and systems that enable a practitioner to remove and clean pulp material in a root canal in a manner that is less likely to result in failure due to bacterial contamination, overly thinning the root canal, perforations or due to infected material being pushed beyond the root from the coronal aspects of canals.

Finally, it would also constitute progress in the endodontic arts to provide methods and systems which yield a predictable success rate, minimal risk of breaking an instrument, lower costs, and an abbreviated operating time or an operating time that is at least as efficient as conventional techniques.

SUMMARY AND OBJECTS OF THE INVENTION

An object of the present invention is to provide, methods and systems which enable a dental practitioner to remove and clean essentially all pulp material in a root canal requiring root canal therapy by progressively cleaning sections of the root canal from the crown to the apex.

Another object of the present invention is to provide methods and systems developed based on the three-dimensional reality of teeth and not just buccolingual x-ray views, thereby enabling a practitioner to remove and clean pulp material in a root canal without compromising the strength of the walls and the apical anatomy.

An additional object of the present invention is to provide methods and systems which encourage perimetrical contact of the instruments with the canal walls.

Additionally, another object of the present invention is to provide methods and systems that enable a practitioner to remove and clean pulp material in a root canal in a manner that is less likely to result in failure due to bacterial contamination, overly thinning the root canal, perforations or due to infected material being pushed beyond the root from the coronal aspects of canals.

Finally, it is an object of the present invention to provide methods and systems which yield a predictable success rate, minimal risk of breaking an instrument, lower costs, and an abbreviated operating time or an operating time that is at least as efficient as conventional techniques.

Some of the features of the invention which enable these objects to be achieved are summarized hereinbelow.

Root Canal Terminology

Rather than speaking generally of "canals" in connection with operative practice, the present applicant prefers the term "canal element", in order to emphasize that each canal has its own "anatomical personality" with which the operator should be familiar. For example, one canal element may have a perimeter shape which is primarily laminar according to the Latrou classification system discussed in the above section entitled the "Background of the Invention" while another canal element may be tubular. Even in a single tooth which has multiple canal elements, it is important to bear in mind that each canal element has a unique morphology.

When referring to a polyradiculated tooth, which has more than one canal element, such as an upper first premolar, applicant prefers the term "canal apparatus" when referring to a set of canal elements.

Applicant utilizes a terminology based on the methodology disclosed herein. The term "operative canal" refers to the pathway which starts at the occlusal surface of the tooth, continues with the cameral wall segment and the anatomical canal per se, and finally reaches the foramen. Of course, the anatomical root canal extends from the pulp chamber or the floor of the pulp chamber to the apex.

The operative root canal is divided into three sections or portions which are referred to herein as "the operative coronal portion", "the operative middle portion" and "the apical portion". The operative coronal portion essentially includes the access cavity walls. The operative middle portion is the upper portion of the anatomical root canal while the apical portion is the lower portion of the anatomical root canal. A typical apical portion is the last or bottom 3 mm of the anatomical root canal.

The terms "operative coronal portion", "operative middle portion" and "apical portion" are unique terms that are distinct from the terminology conventionally utilized to refer to segments of a root canal. In the conventional crown-down method, the canal is customarily divided into the so-called "three thirds", including: the crown, the middle third, and the apical third. In reference to the conventional crown-down method, it is common to use the term "coronal third" to refer to the first part of the "anatomical" canal, originating at the floor of the pulp chamber or the upper limit of the middle third into which a tooth is customarily divided, with a theoretical line at the height of the neck.

Methodology Overview

During the root canal therapy, the pulp chamber can be opened to expose the anatomical root canal by any conventional method or instrument. Additionally, conventional methods and instruments can be used to prepare the operative coronal portion. However, unique methods and instruments are used in the operative middle portion while preferably simultaneously abrading the operative coronal portion. Additionally, after the operative middle portion has been cleaned, unique methods and instruments are used to improve access into the apical portion and to then clean the apical portion.

The present applicant developed the methodology disclosed herein based on the anatomical reality discussed above in the section entitled "Background of the Invention". By envisioning the canal in which they are operating as starting at the occlusal surface, practitioners can immediately identify any "interferences" or obstructions, as well as any protrusions of enamel, which may be disregarded. As a result, the instruments disclosed herein come into contact with every segment of the canal walls, including the obstructions, in order to achieve anatomical widening and also the rectification or straightening of the first two portions of the canal which include the operative coronal portion and the operative middle portion. This procedure opens the pathway for the preparation of the apical portion of the canal.

The methodology disclosed herein involves the use of distinct instruments in the three portions of the anatomical root canal in different phases such that the root canal is cleaned progressively and sectionally. The instrument(s) associated with each phase have been designed specifically for that particular phase and accordingly have unique customized characteristics and features. The instruments are described hereinbelow after explaining the procedures for completing each phase.

By cleaning the root canal in sections, the instruments can be adapted to the perimetrical or perimetral anatomy of the root canal. As a result, the entire perimeter or substantially all of the perimeter is contacted and cleaned along the length of the perimeter without substantially altering the configuration of the perimetrical anatomy. For example, a perimetrical anatomy that was primarily tubular or laminar perimetrical anatomy will be enlarged but will still be primarily tubular or laminar. There will not be a large round borehole in the canal superimposed on the original perimetrical anatomy which corresponds to the diameter of the file that is used, as is the case with the nickel/titanium files that stay in the center of the canal even when the canal is laminar.

Additionally, the invention also enables the practitioner to prepare root canals in accordance with the anatomy of the root canal, even though the practitioner may not have been able to adequately identify the overall anatomy due to the inability to see the root canal as is the case from the mesial-distal view using standard radiography. Further, the invention also enables the practitioner to adapt to the contours of the root canal of all different types of teeth, by guiding instruments that have been designed to come into contact with every perimetrical segment of the walls.

Interferences and Rectification

The term "interference" refers to everything in the operative canal that hinders the rectilinear insertion of the instruments used, during the final cleaning phase of the procedure, preparation of the apical portion. The term "rectification" refers to the placement of the operative coronal portion or access cavity on the same axis as the operative middle portion. Rectification is achieved through the removal of interferences from the operative coronal portion and preferably from the operative middle portion of the operative canal as well.

Instrumentation of the Operative Coronal Portion

In this phase, the access cavity is created, after elimination of all of the coronal tissue from a carious and weak tooth, and after removal of any infiltrated restoration(s). The access cavity is also created prior to coronal reconstruction, if considered necessary in order to facilitate the installation of the dam.

It is not necessary to perform a prophylactic cuspidal flattening or cuspidectomy in accordance with the methodology as disclosed herein. However, it may be desirable to perform a cuspidectomy with some teeth, particularly lateral postcanine quadrants, in order to create a flat reference plane for the stop, to create an approach nearer to the pulpar horns, to eliminate occlusal contact, and to reduce the masticatory stress on a weakened coronal structure. Weakening of the coronal structure is typically caused by the primary carious process and by the subsequent removal of the roof or top of the chamber due to the need to create the cavity that allows access to the pulp chamber and to the root canal. However, in view of the fact that the top of the chamber is the natural connection between the cuspids, and that after destruction of the top of the chamber, which connects the cuspids, the diameter of the base of the cuspidal columns remains weak in terms of resisting lateral masticatory stress; the operator needs to be assured of the usefulness of performing the prophylactic cuspidectomy on the postcanine teeth.

Apart from avoiding the risk of fractures, the rehabilitative reconstruction of the root canal element may subsequently be facilitated.

Instrumentation of the Operative Middle Portion

The most important part of this phase is the determination of the so-called "working length" of the first two portions of the operative root canal including the operative middle portion and the operative coronal portion. The methods for identifying the working length involve the use of x-rays or videography, performed with the aid of a centering device and through use of the long-cone method. After the working length has been determined, then the proper instruments can be selected for use in the preparation of the operative middle portion.

The working length is determined by measuring the canal axis from the occlusal plane, in order to arrive at the apical limit of the root as indicated on the x-ray. A distance of 3 mm is deducted from the measured length. The result is the maximum working depth that the operative middle portion instrument(s) should reach. The foregoing calculations also figure in the predetermination of the working lengths for all other instruments utilized in the procedure.

The preparation of the first two portions also involves catheterization. Additionally, this phase involves the anatomical widening of the perimeter of the operative middle portion as well as the removal of the interferences from the operative coronal portion and the operative middle portions, thereby allowing the rectification of the first two portions of the operative root canal.

Please note that during preparation of the operative middle portion and rectification of the first two portions, any and all intrusion of the instrument(s) into the apical portion is avoided. The boundary between the operative middle portion and the apical portion has been estimated to be located between 3 mm and 5 mm from the end of the root canal, as shown on the x-ray. After preparation of the operative middle portion and rectification of the first two portions have been completed, the procedure moves to the third stage, in which the apical portion is prepared.

After the working length has been determined for the first two portion including the operative coronal portion and the operative middle portion, the operator selects an instrument from a set of instruments designed for use in the operative middle portion. The instruments are preferably held in a mini-container whose length is about the same as the identified working length of the instruments.

The contours of the perimeter of the root canal in the operative middle portion are followed as the file of the instrument(s) is flexed or curved against the surfaces of the root canal and simultaneously moved in a cleaning motion. Since the contours are followed, the perimeter is widened and smoothed but the original shape is not substantially altered.

Instrumentation of the Apical Portion

Before preparation of the apical third is begun, the apical and periapical condition of the element is evaluated, in accordance with the following guidelines. For living or necrotic teeth "without rearrangement of the apex" or apical rarefaction, the instrument(s) should be kept no closer than 2 mm from the apex as shown on the x-ray image. Conversely, for necrotic teeth with apical autolysis, the preparation work may be performed up to a distance of 1 mm from the apex as shown on the x-ray image. The predetermination of the widening of the canal leading to the apex, and the widening of each root canal for polyradiculated teeth, should be made bearing in mind the guidelines for the widening limits set forth in the morphometric data provided in Tables 2 and 3.

In most cases, the radicular apex contains the final segment of the main canal, which divides into a delta configuration as discussed above in reference to FIG. 3C. This structure is hard to detect with x-rays. Therefore, the morphology of the dental apex is unpredictable, and the location of the junction between the cementum and dentin in any endodontic apex is random. Likewise random is the hypothetical apical constriction that can be detected by the most expert professionals. A degree of confidence can be obtained through the use of electronic measurement devices in living canals that have not been treated with liquid medications, but only when the foramen has been passed, in order to be subsequently withdrawn into the canal with a probe instrument. This maneuver should be avoided in necrotic canals, because of the risk of carrying germs beyond the apex.

The guidelines discussed above should be kept in mind when redetermining the approximately working length to the apex after the operative middle portion has been prepared. It is necessary to redetermine the working length as the working length has likely changed due to the instrumentation of the operative middle portion.

Instrumentation in the apical portion can begin after the working length has been determined. There are two phases of instrumentation within the apical portion of the operative root canal including widening and cleaning of the apical portion.

After the operative middle portion has been cleaned then access is improved into the apical portion such that an irrigation needle can be deployed to deliver irrigants to the apical portion. By widening the access into at least the entrance of the apical portion and preferably the entire apical portion, irrigants can be delivered into the apical portion to maintain the debris derived from cleaning the root canal in suspension. The debris would otherwise prevent the proper preparation and filling of the apical portion of the root canal as the particles of the smear layer yielded from the action of the files used to prepare the canal would result in clogging the apical portion of the root canal with a plug.

The apical portion may be cleaned after the operative middle portion of the operative root canal has been cleaned and preferably after appropriate instrumentation to enable irrigants to be delivered into the apical portion.

Instruments operative middle portion of the operative root canal is cleaned with a first instrument or set of instruments. An optional second instrument or set of instruments can then be used to improve the access into the apical portion to enable irrigants to be delivered into the apical portion from an irrigation needle. A third instrument or set of instruments is provided to clean the apical portion of the operative root canal after the operative middle portion of the root canal has been cleaned and after the access into the apical portion has been widened.

Each instrument in the first set of instruments comprises a handle connected to a file with an abrasive surface or in other words a shaft with tines or an abrading portion. Each file has a length such that the operative middle portion of the operative root canal is cleaned without significantly removing pulp material from the apical root portion. Additionally, each file is designed to have a taper that is larger than the taper of each preceding file. Each file or shaft has an abrading portion for abrading the surfaces or walls of the root canal. In contrast to conventional files, as set forth in greater detail hereinbelow, the abrading portion may extend along the entire length of the file to enable the instrument to be used to clean the operative middle portion while also abrading the operative coronal portion.

The files of the instruments in the first set are designed such that each file has sufficient flexibility to be flexed or curved to urge the abrading portion against the surfaces of the root canal and sufficient rigidity to apply pressure against the surfaces of the root canal as the abrading portion of the file is urged against the surfaces of the root canal and simultaneously moved in a cleaning motion. Additionally, the files have adequate resilience to avoid being substantially deformed as the file is flexed or curved to urge the file, particularly the abrading portion, against the surfaces of the root canal.

Each instrument in the second set of instruments used to improve or widen the access for the introduction of an irrigation needle to the apical portion comprises a handle connected to a file. Each file terminates at a tip and each file is configured with an abrading portion. Each file has a length sufficient to at least approximately reach the apex and to enable the abrading portion of the files to improve the access into the apical portion of the root canal.

Each instrument in the third set of instruments used to clean the apical portion comprise a handle connected to a file. Each file terminates at a tip and each file is configured with an abrading portion. Each file has a length sufficient to at least approximately reach the established apical working limit and to enable the abrading portion of the files to substantially contact and clean the pulp material in the apical portion of the root canal. The tip of the file is preferably rounded to prevent ledging.

These and other objects and features of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages and objects of the invention are obtained, a more particular description of the invention briefly described above will be rendered by reference to a specific embodiment thereof which is illustrated in the appended drawings. Understanding that these drawings depict only a typical embodiment of the invention and are not therefore to be considered to be limiting of its scope, the invention will be described and explained with additional specificity and detail through the use of the accompanying drawings listed hereinbelow.

FIG. 6A is a longitudinal cross-sectional view of an extracted lower first molar to show the anatomy of the tooth from the buccal-lingual view.

FIG. 6B is a longitudinal cross-sectional view of the extracted lower first molar shown in FIG. 6A from the mesial-distal view.

FIG. 7 is a cross-sectional view of extracted teeth which have been cut along into transverse cross-sectional segments to show the general categorization of root canal perimetrical anatomies.

FIG. 16B is an enlarged perspective view of a tip of one of the files of an endodontic file instrument shown in FIG. 16A.

FIG. 17A is a perspective view of another embodiment of a set of endodontic instruments for cleaning of the coronal portion of a root canal.

FIG. 17B is an enlarged perspective view of a tip of one of the files of an endodontic file instrument shown in FIG. 17A.

FIG. 17C is another embodiment of a file tip of an endodontic file instrument.

FIG. 36A is a cross-sectional view of a tooth after the pulp chamber has been accessed and before rectification.

FIG. 36B is a cross-sectional view of the tooth shown in FIG. 36A after rectification and after the operative middle portion has been cleaned.

FIG. 36C is a cross-sectional view of the tooth shown in FIG. 36A after the apical portion has been widened.

FIG. 36D is a cross-sectional view of the tooth shown in FIG. 36A after the apical portion has been cleaned.

DETAILED DESCRIPTION OF THE PREFERRED EMBODIMENTS

The present invention relates to systems and methods for cleaning root canals through the removal of pulp material from the root canals. The invention provides for cleaning the root canal in progressive sections from crown to apex. After the pulp chamber is opened and preferably after further preparations, a first instrument or set of instruments is introduced into the root canal to clean the root canal up to the apical root portion. A second instrument or set of instruments is then optionally introduced to improve the access into the apical portion. The apical root portion is then cleaned with a third instrument or set of instruments. The invention enables a dental practitioner to remove and clean essentially all the pulp material in a root canal requiring root canal therapy. The cleaning is achieved in a manner that is safer in terms of over thinning of the root canal and perforations and yet requires less instrumentation than conventional techniques.

Figure 18:
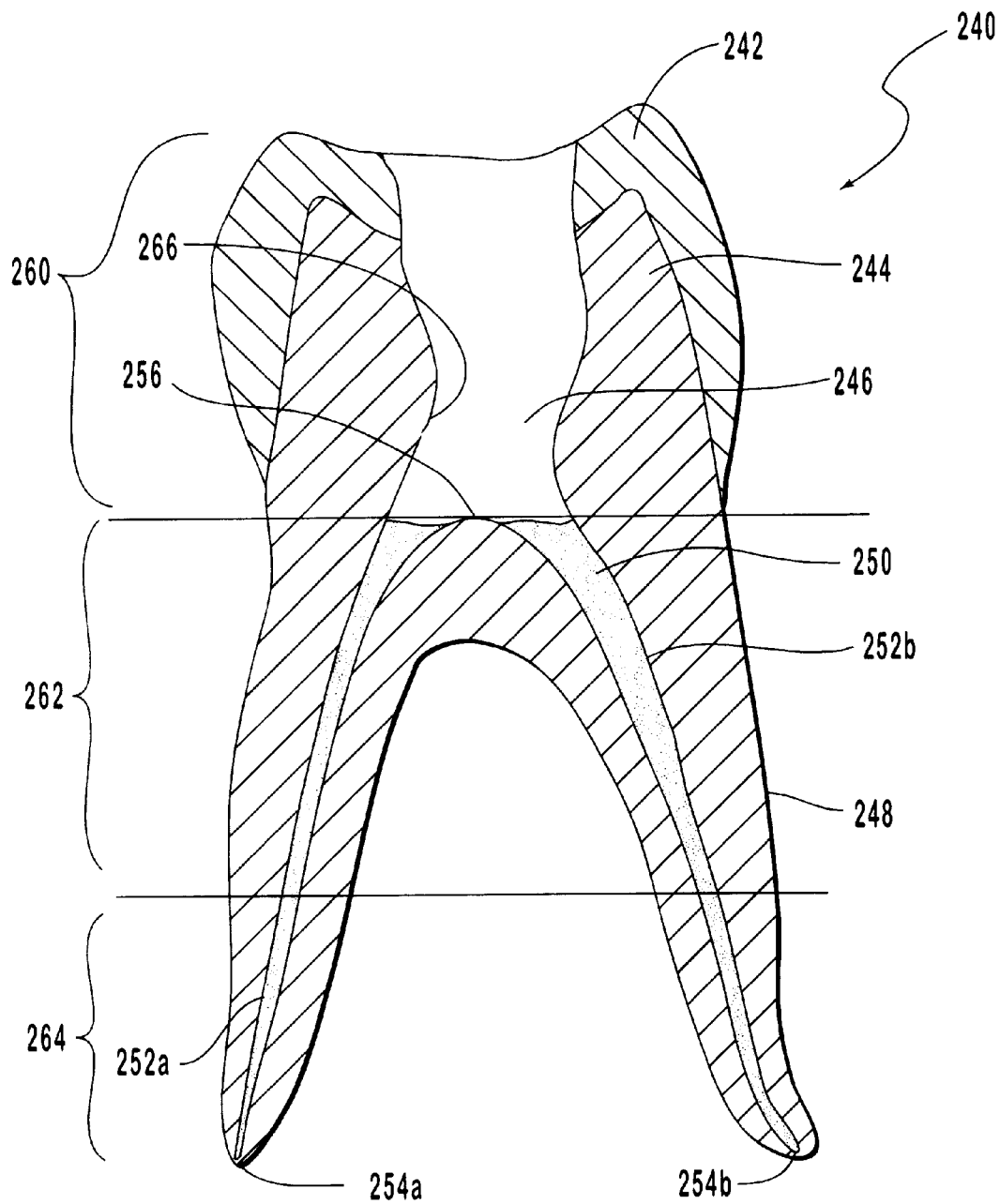
FIG. 18 is a longitudinal view of a tooth with an exposed pulp chamber.

The techniques described herein for progressive root canal therapy, from crown to apex, are essentially divided into distinct phases. The phases generally correspond with the particular sections or portions of the operative root canal. After the pulp chamber has been opened to expose the anatomical root canal, during the root canal therapy, as shown in FIG. 18, the operative root canal is considered to include the anatomical root canal, which extends from the pulp chamber or the floor 256 of the pulp chamber 246 to the apex 254, and the operative coronal portion thereabove. More specifically, the operative root canal comprises the operative coronal portion 260, the operative middle portion 262 and the apical portion 264. Operative coronal portion 260 essentially includes the access cavity walls. The operative middle portion 262 is the upper portion of the anatomical root canal while the apical portion 264 is the lower portion of the anatomical root canal.

The divisions of the operative root canal are distinguished from the nomenclature of the anatomical root canal as used to designate the sections before opening the tooth wherein the anatomical root canal is divided into the apical portion and the coronal portion. The coronal portion of the anatomical root portion is conventionally defined as the upper portion of the anatomical root canal which terminates at the floor of the pulp chamber. However, once the pulp chamber is exposed and instruments are introduced into the root canal, the opening into the tooth should be treated as an extension of the operative root canal as it is then a continuous chamber or open tract. Accordingly, the access walls are considered part of the operative root canal and are designated as the operative coronal portion or the access portion.

Apical portion 264 extends from the apex of root canal 252 up to an area of anatomical root canal 252, such that the length of the apical portion is less than half of the length of the anatomical root canal as measured from the apex to floor 256. More specifically, apical portion 264 is generally the bottom one-half of the anatomical root canal 252. The actual length of the apical portion varies depending on many factors such as the type of tooth and the age of the tooth. However, the apical portion typically has a length in a range from about 3 mm to about 4 mm as measured from the apex.

As also indicated hereinabove, operative middle portion 262 is the top portion of the anatomical root canal 252 and extends from floor 256 down to an area of anatomical root canal 252, such that the length of the operative middle portion is greater than half of the length of anatomical root canal 252. More specifically, operative middle portion 262 is generally the top two-thirds of anatomical root canal 252 as measured down from floor 256. The length of operative middle portion can be estimated by identifying the overall length of the root canal, typically by use of radiography, and then subtracting about 3 mm to about 4 mm from the overall length.

Figure 16A:
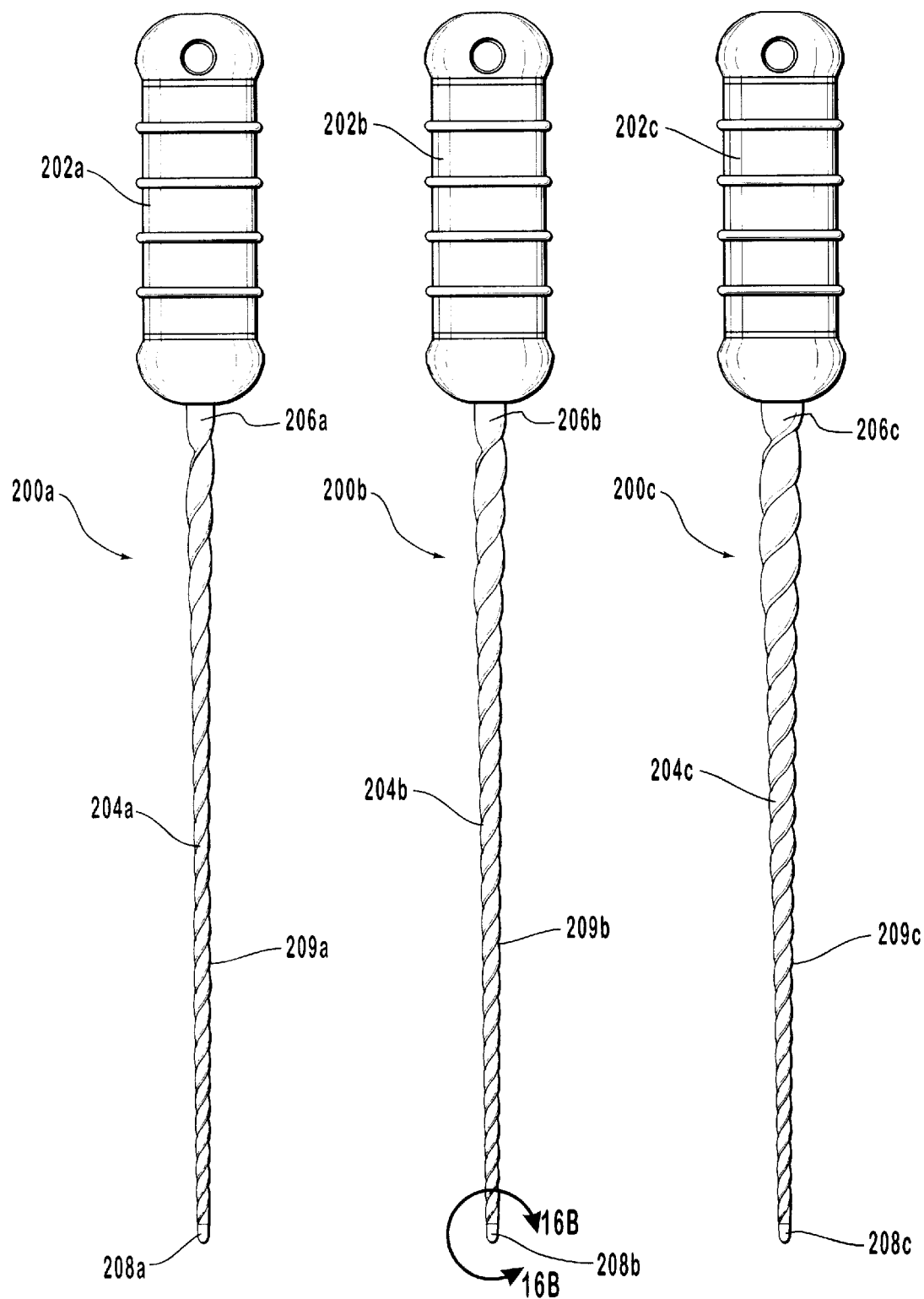
FIG. 16A is a perspective view of a set of endodontic instruments for cleaning of the coronal portion of a root canal.
Figure 21:
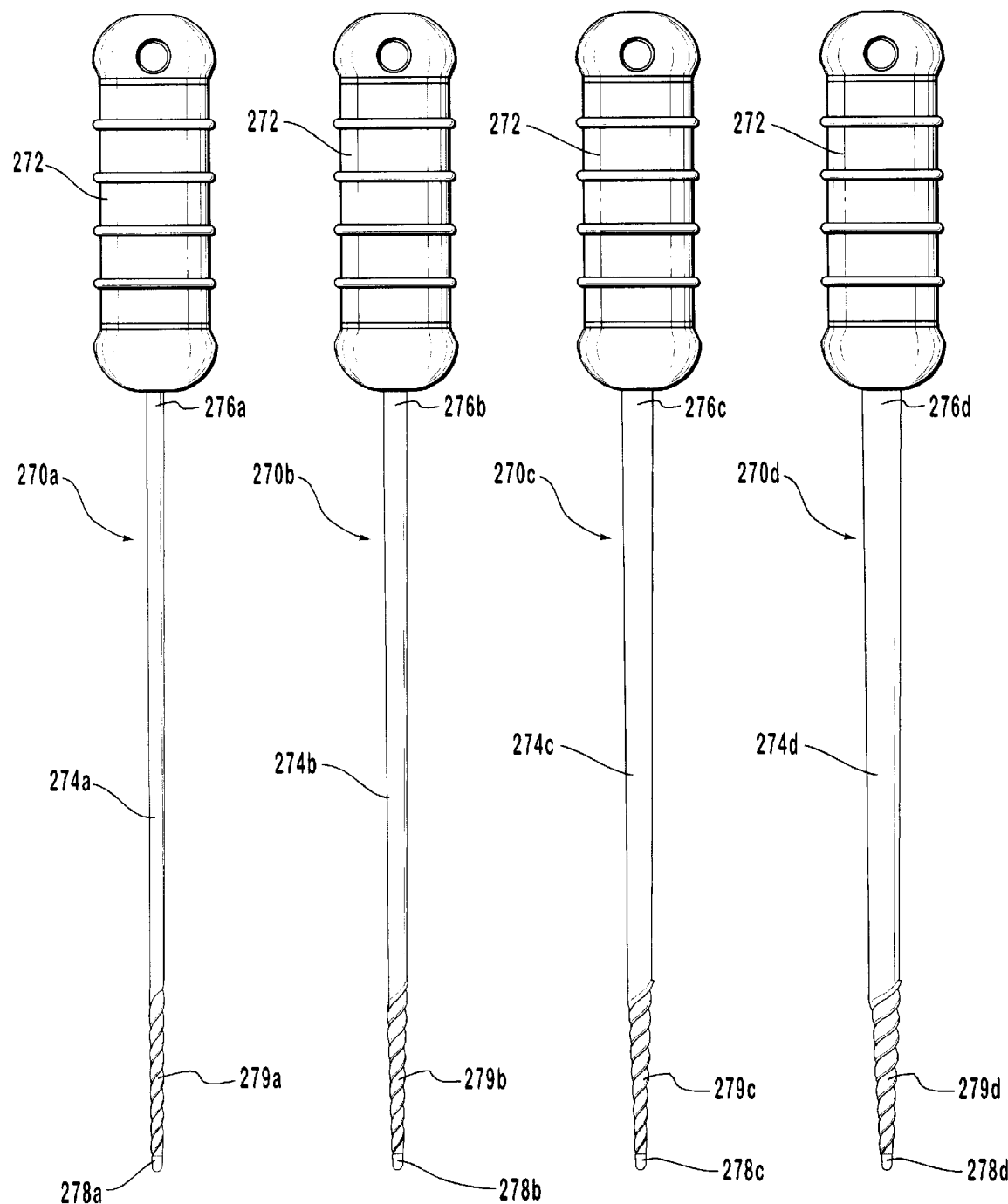
FIG. 21 is a perspective view of a set of endodontic instruments for improving the access into the apical portion of a root canal.
Figure 22:
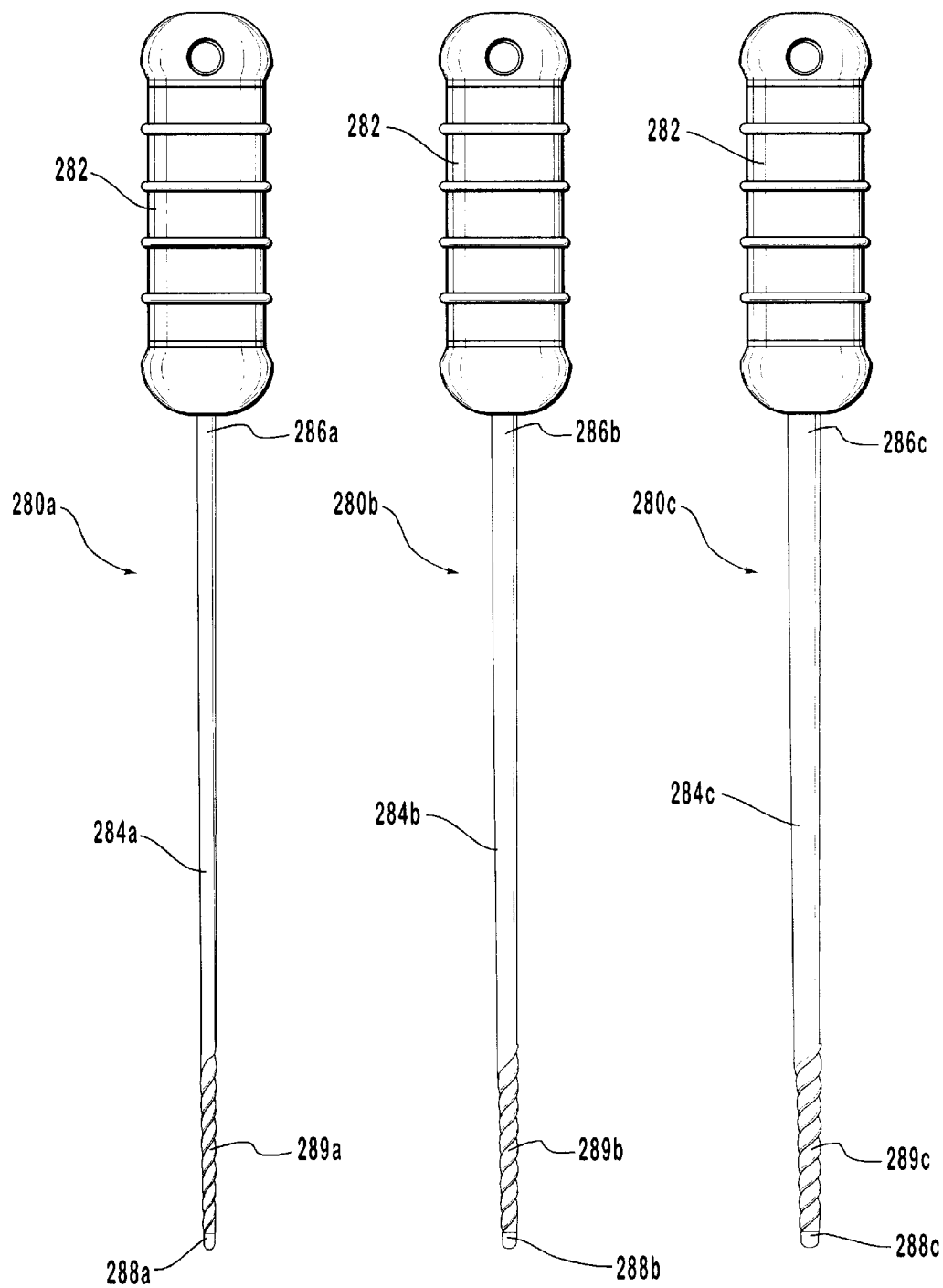
FIG. 22 is a perspective view of a set of endodontic instruments for cleaning the apical portion of a root canal.
Figure 23:
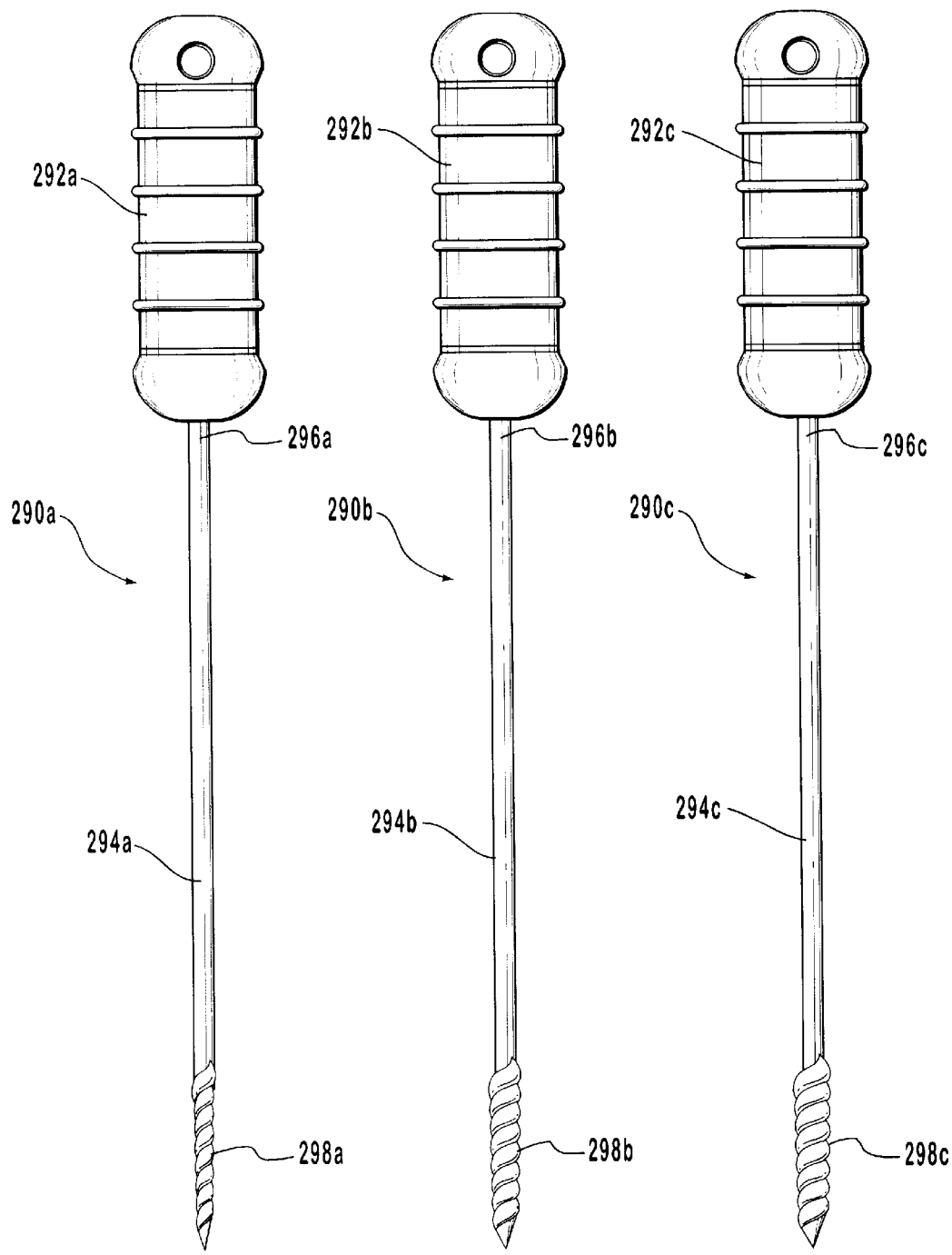
FIG. 23 is a perspective view ot another embodiment of a set of endodontic instruments for cleaning the apical portion of a root canal.
Figure 24:
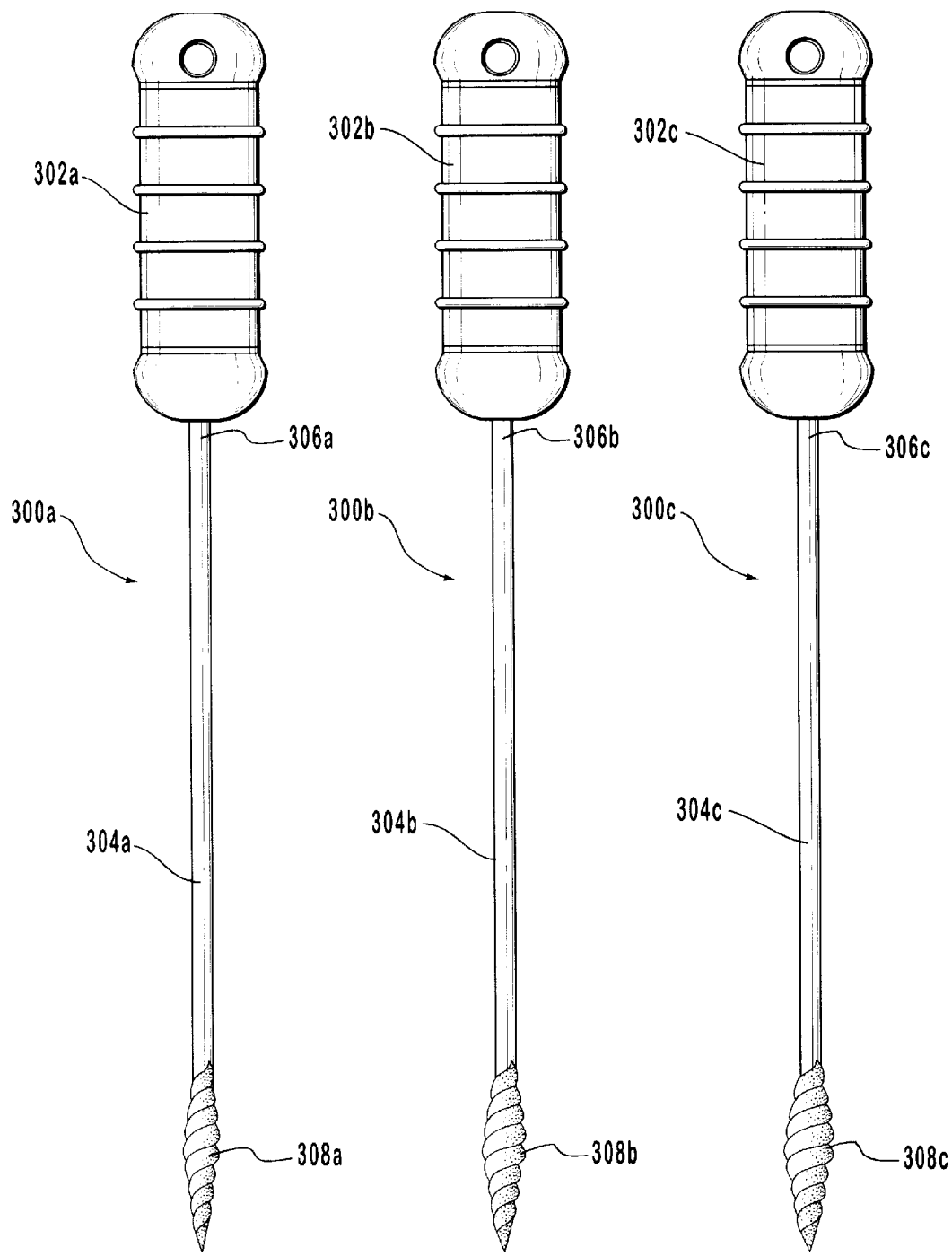
FIG. 24 is a perspective view of an additional embodiment of a set of endodontic instruments for cleaning the apical portion of a root canal.

As previously indicated, the three sections are treated in primarily distinct sequential phases including: preparation of the operative coronal portion, then cleaning or preparation of the operative middle portion, improving access to the apical root portion and finally cleaning of the apical portion. Examples of instruments intended for use in the cleaning the operative middle portion are shown in FIG. 16A and FIG. 17B. FIG. 21 depicts an example of a set of instruments designed for use in improving the access to the apical root portion. Examples of instruments intended for use in cleaning the apical portion are shown in FIGS. 22–24.

Figure 11A:
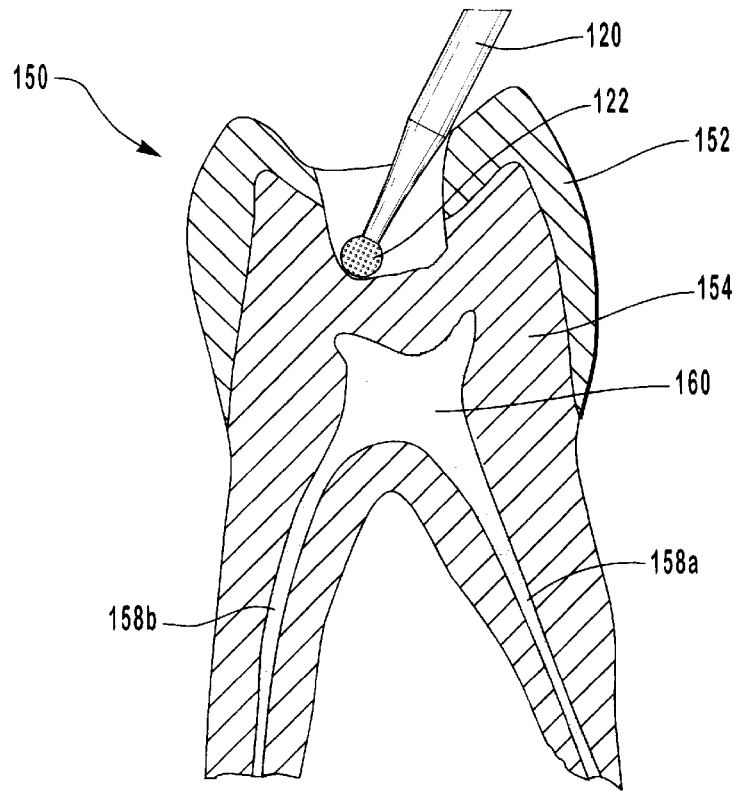
FIG. 11A is a longitudinal cross-sectional view of a burr being utilized to remove the overhanging enamel and dentin above the pulp chamber.
Figure 11B:
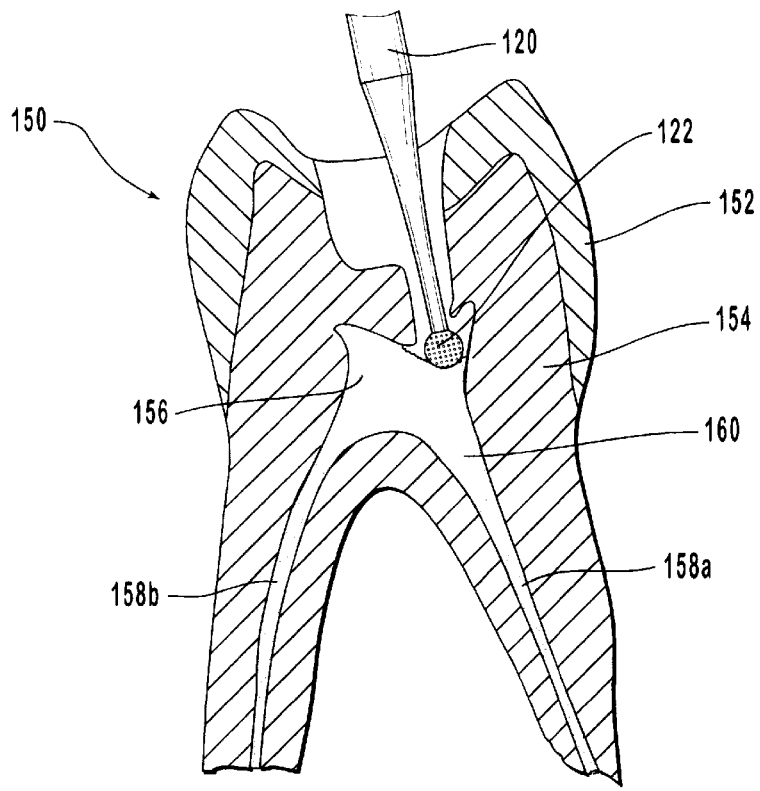
FIG. 11B is a longitudinal view of a burr extending through the enamel and the dentin into the pulp chamber.
Figure 12:
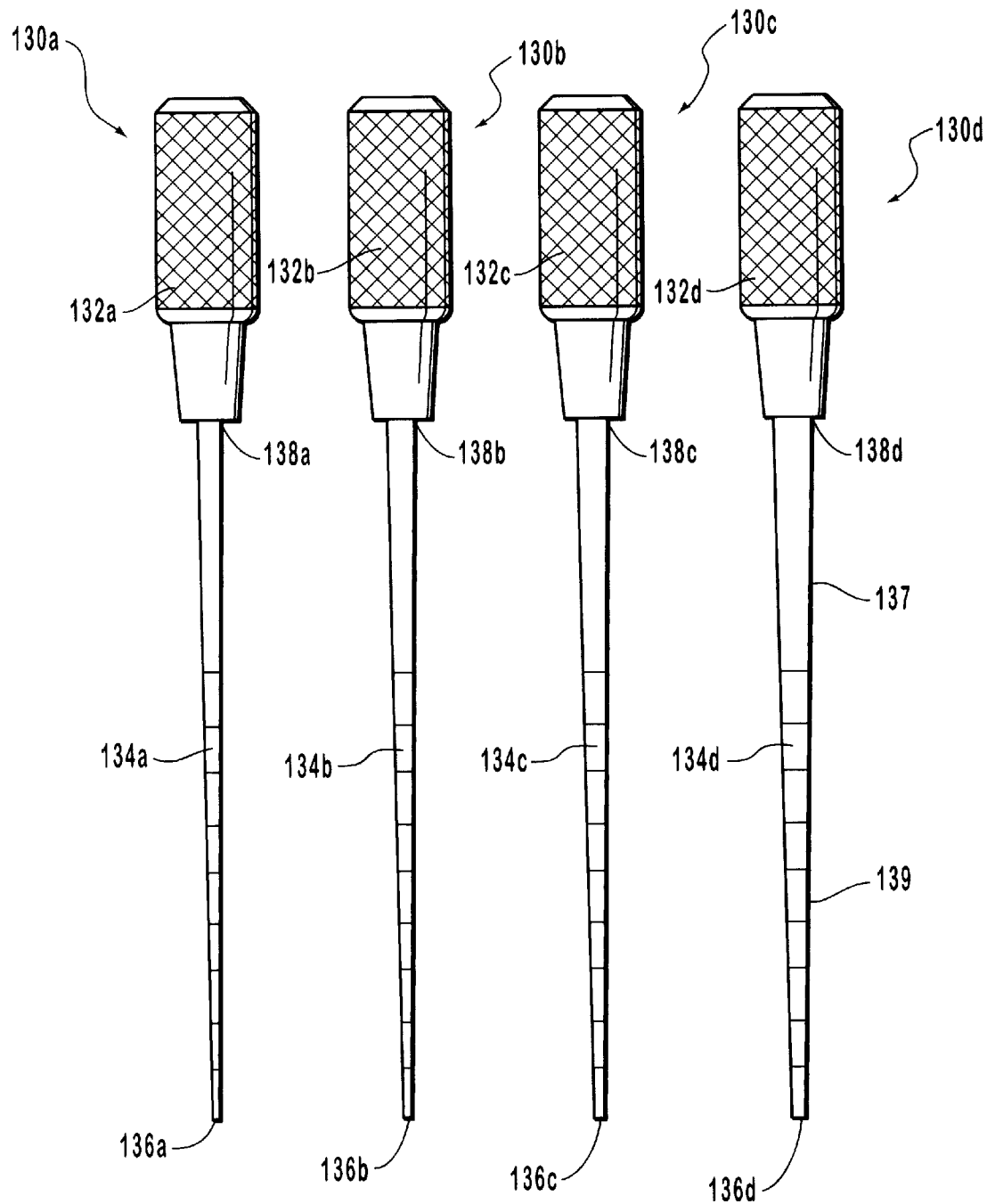
FIG. 12 is a perspective view of a prior art set of endodontic instruments utilized in the step-back technique.

The first phase or coronal phase involves exposing the pulp chamber and also preferably other steps to enhance accessibility into operative middle portion 262 and also apical portion 264. Accordingly, the coronal or access phase is initiated by removing the top of the chamber to expose the pulp chamber. This can be achieved, for example, through the use of an instrument such as instrument 120 with bur 122 as shown in FIGS. 11A and FIG. 11B, which is preferably a diamond bur used in conjunction with a lout or high speed handpiece. However, any suitable instrument can be utilized such as those disclosed in Italian Patent No. 1,142,983 or Italian Patent No. 1,149,157, which are hereby incorporated by reference.

After the pulp chamber has been exposed and after the pulp material has been removed, a tooth appears as shown in FIG. 18 wherein a molar 240 is depicted with the overhanging portions of enamel 242 and dentin 244 removed to provide access into pulp chamber 246. Pulp material 250 still extends within root canal 252 from apices 254a and 254b to the floor 256 of pulp chamber 246. Also designated at 248 is the cementum of the tooth.

During the first phase, it is preferable to remove or reduce dentinal or enamel protrusion or irregularities that may obscure or hinder access of instruments into the remaining portions of the operative root canal. For example, dentinal shelves 266 depicted in FIG. 18 are preferably reduced or rectified to provide greater access for instrumentation during the subsequent phases. More particularly, interferences are preferably removed or minimized such that instruments can be inserted in the anatomical root canal in a relatively straight manner. Accordingly, in the subsequent related drawings, such as FIG. 19A, the dentinal shelf is shown removed on the canal being cleaned and as not being yet removed above the other canal. Rectification or regularization can be achieved by any suitable means. An example of a means for rectifying dentinal shelves is set forth in U.S. Pat. No. 5,642,998 which was incorporated by reference hereinabove. It may also be necessary to widen the tract of the operative coronal root canal. Some dentists man prefer to obtain greater access through a cuspidectomy.

During this phase as well as the others, it is generally necessary to utilize irrigants. Any irrigation means can be utilized. However, it is preferable to utilize an irrigation tip as set forth in copending U.S. patent application Ser. No. 09/014,764 entitled Endodontic Irrigator Tips and Kits and filed by Francesco Riitano on Jan. 28. 1998; the disclosure of which is hereby incorporated by reference. During the procedure, a rubber dam is typically used to isolate the tooth, which may require in some instances, the rebuilding of the pulp chamber walls.

After the operative coronal portion has been adequately prepared, it is preferable to prepare an x-ray image of the tooth to identify the length of the operative root canal in order to determine the preferred working length for the instrument or set of instruments to be used in the next phase. The preferred working length is preferably identified by subtracting about 3 mm from the total radiographic length of the operative root canal. The total radiographic length is preferably derived from a radiograph made using a localizator and a long cone radiographic head.

The second phase involves cleaning or preparation of operative middle portion 262. It may also involve to some extent further rectification of the operative coronal or access portion 260 through further removal of any ledges or outcroppings which prevent straight and 24 easy access into the operative middle portion 262. Additionally, it may also involve some degree of rectification of the upper region of operative middle portion 262.

An example of a set of instruments designed for cleaning the operative middle portion is shown in FIG. 16A. The set comprises three file instruments 200 which each comprise a handle 202 connected to a file 204 or a shaft with tines or an abrading portion. Each file 204 has a top end 206 where the file joins handle 202. Handle 202 is connected to top end 206 of file 204 such that movement of handle 202 also moves at least top end 206 of file 204 along a common longitudinal axis with handle 202.

The diameter of top end 206a is less than the diameter of top end 206b and the diameter of top end 206b is less than the diameter of top end 206c. When utilized to clean the operative middle portion of a root canal, file 200a is first introduced into the operative middle portion followed by file instrument 200b and then 200c. Accordingly, the diameter of the top end of each successive file introduced into the operative middle portion is greater than the diameter of the top end of each preceding file.

Each file terminates at a tip 208 located opposite top end 206. The diameter of each tip 208 in a set of instruments is essentially the same such that the diameter of tip 208a is about the same as the diameter of tip 208b and tip 208c. For example, a set of instruments may all have tip diameters of about 0.10 mm. A set may also be designed such that the instrument intended to be inserted first has a tip diameter of about 0.10 mm while the other instruments in the set have a tip diameter of about 0.13 mm. A set with slightly different tip diameters, such as a set of three or four instruments with respective tip diameters of 0.10 mm, 0.10 mm, 0.13 mm and 0.13 mm, and in any event not exceeding 0.15 m, is still considered to have substantially constant tip diameters within the set as the difference in size is very minor and the diameters do not sequentially increase for each instrument. In an alternative embodiment, the tip diameter may vary between instruments in a set such that, for example, the tip diameter of each sequentially inserted file is progressively larger. As shown in FIG. 16B, which is an enlarged view of tip 208b, the tips are generally sharp and are configured for at least minimal cutting capability.

Each operative middle portion file 204 is configured with a suitable abrading portion 209 along most or all of the length of each file. The file is preferably configured such that the abrading portion 209 extends along its entire length as shown in FIG. 16A, however, the files may also have a smooth upper shank portion. Abrading, portion 209 is at least the outer edge of the file 204. The abrading portion of the files in FIG. 16A are formed by twisting a blank such as a rectangular blank.

FIG. 17A depicts another set of file instruments 210 which have files with a different abrading portion compared to the abrading portion of the files of file instruments 200. The files 214 have abrading portions 219 that were formed by machining the files to have knurled surfaces. Abrading portion 219 as well as abrading portion 209 and the other abrading or cleaning surfaces disclosed herein are examples of means for abrading the walls of the root canal.

FIG. 17B is an enlarged view of tip 218a which is shown with a more rounded configuration than tip 208b such that the tip has essentially no cutting capability, FIG. 17C shows another embodiment of a suitable tip which is designed for more aggressive cutting than tip 208b at least as the tip is pushed downward.

Since the tip diameters are essentially equal and since the diameter of the top end of each successive file introduced into the operative middle portion is larger than the diameter of the top end of the preceding file, the taper of each successive file in the set is larger than the preceding file. For example, the taper may range from 0.04 to 0.13 and increase in increments for each successive file. Each successive file accordingly has an increased surface area for cleaning the root canal. Additionally, as files are inserted into a root canal with larger and largyer tapers, the rigidity of the upper half of each successive file also increases. The increase in rigidity is, however, minimized by maintaining the tip of each file at about the same diameter. The flexibility of the lower half remains essentially constant. The rigidity in the upper half is used to remove interferences and to properly, rectify, the operative coronal portion 260 and the operative middle portion 262. The consistency in rigidity at the upper half is useful since the lateral perimetrical force applied to the handle is primarily transferred to its upper half or at least the part closest to the handle, which is the strongest part of the file.

By properly selecting a combination of factors including the diameters of the files at the top ends and at the tips as well as the material used to form the files, the files are designed such that each file has sufficient flexibility to be flexed or curved to urge the abrading portion against the surfaces or walls of the root canal and sufficient rigidity to apply pressure against the surfaces of the root canal as the abrading portion of the file is urged against the surfaces of the root canal and simultaneously moved in a cleaning motion. Additionally, the files have adequate resilience to avoid being substantially deformed as the file instrument is flexed or curved to urge the abrading portion against the surfaces of the root canal.

The file can be formed from any suitable material. In forming a suitable file, the material is preferably selected in view of the dimensions and design, to yield a file having the desired properties with respect to flexibility, resilience and/ or rigidity as set forth above. The preferred material for forming files used to clean the operative middle portion of root canals is stainless steel. Other metals can also be used such as nickel/titanium; however, it may be necessary to design the files to have larger diameters than files formed from stainless steel when using nickel/titanium as nickel/ titanium tends to be more flexible than steel. Alternatively, the files can be formed from suitable non-metal materials, such as a plastic.

The length of each file in the set used to clean the operative middle portion depends on the length of the tooth being cleaned. More particularly after identifying the length of the root canal from an x-ray image the length of the file to be used in the operative middle portion is determined by subtracting 3 mm from this identified length of the root canal. This length is typically between about 15 and about 20 mm, however, longer files, such as a 25 mm long file, are typically required for canine teeth. To provide for the different root canal configurations which may be encountered, it is preferred to have files with lengths ranging from about 8 mm to about 35 mm. However, files with lengths ranging from about 10 mm to about 30 mm will be most utilized and files with lengths ranging from about 14 mm to about 26 mm will be the most frequently utilized.

When the files are formed from stainless steel or a material with comparable properties, the top end diameter of each file, where the abrading portion terminates, may range from about 0.25 mm to about 2 mm. However, the diameter will more typically range from about 0.3 mm to about 1.8 mm and most typically from about 0.4 mm to about 1.5 mm. Additionally, when the files are formed from stainless steel or a material with comparable properties, the tip diameter of each file may range from about 0.06 mm to about 0.4 mm. More typically, however, the tip diameter will range from about 0.08 mm to about 0.15 mm and most typically from about 0.08 mm to about 0.1 mm.

Figures 19A, 19B:
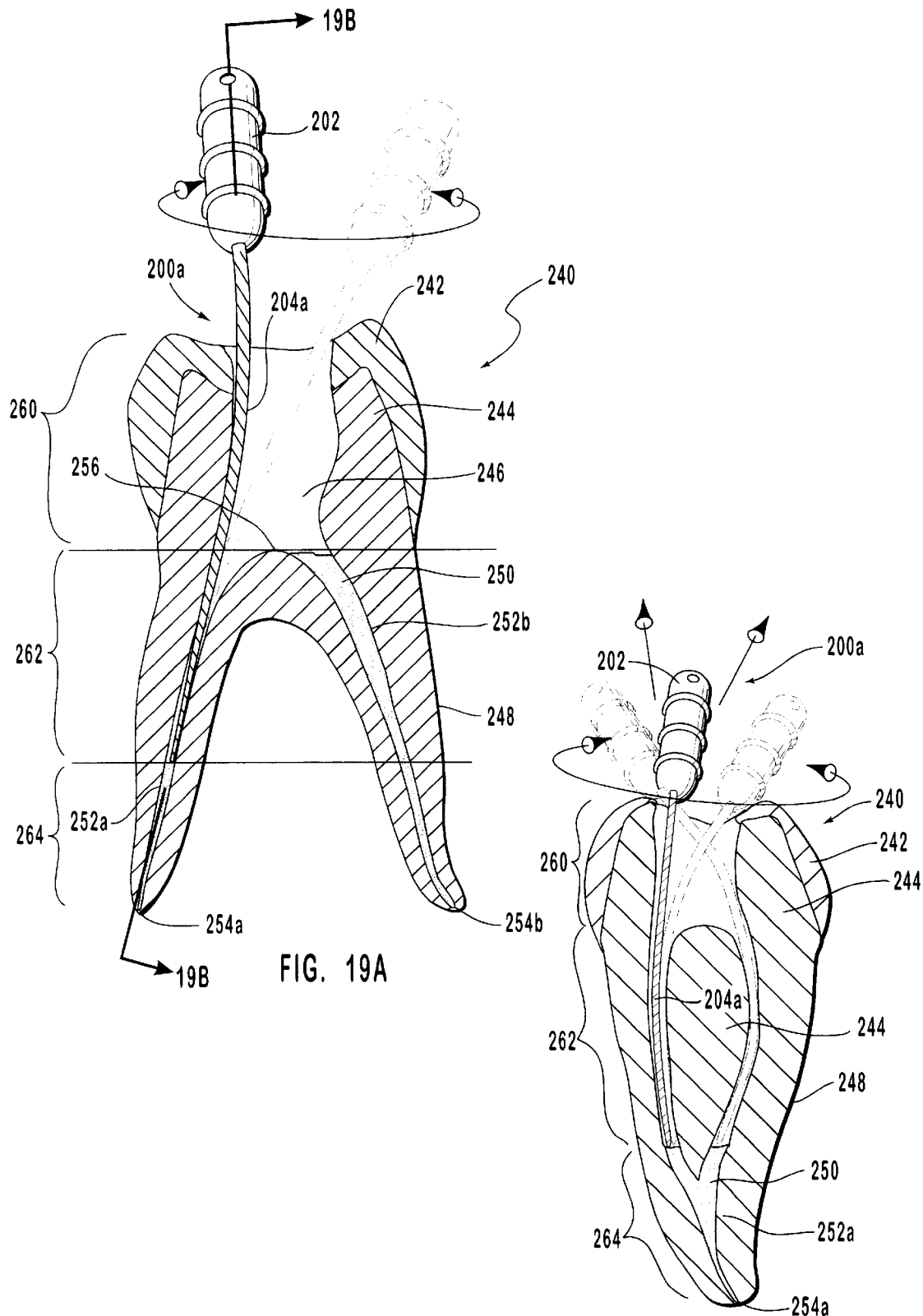
FIG. 19A is a longitudinal cross-sectional view of a tooth with a file portion of a file instrument inserted into the root canal up to the apical portion.
FIG. 19B is a longitudinal cross-sectional view of the tooth shown in FIG. 11A taken along cutting line 19B—19B to depict the cleaning of the pulp material from the coronal portion of the root canal.

After identifying the combined length of the operative middle portion and the operative coronal portion and after removing the overhanging enamel 242 and dentin 244, the practitioner selects a file instrument or a set of file instruments as shown in FIG. 16A or FIG. 17A with a file length corresponding to the combined length of the operative middle portion length and the operative coronal portion. As shown in FIG. 19A, file 204a of file instrument 200a is then inserted into root canal 252 down through operative middle portion 262 without extending substantially into apical portion 264. Each file 204 of each file instrument 200 in the set of instruments shown in FIG. 16A has a length that is only sufficient to enable the file to contact the operative middle portion and the operative coronal portion of the root canal. Accordingly, a file instrument such as file instrument 200a or a set of file instruments such as 200a, 200b and 200c comprises a first endodontic instrument means for anatomically removing and anatomically cleaning essentially all pulp material from the operative middle portion without significantly removing pulp material from the apical root portion.

The file length of files 204 enables a practitioner to aggressively clean the operative middle portion without worrying that the instrument will overly thin the root canal, perforate the apex or that cleaning will cause extrusion of material through the apex. Another benefit of cleaning the operative middle portion first is that the apical portion is then generally more accessible and easily cleaned. Additionally, since instruments are selected for use in cleaning the operative middle portion which have files lengths that do not permit entry into the apical portion, the likelihood of jamming or breaking a tip of an instrument while working in the confined space of the apical portion is prevented.

Figure 1A:
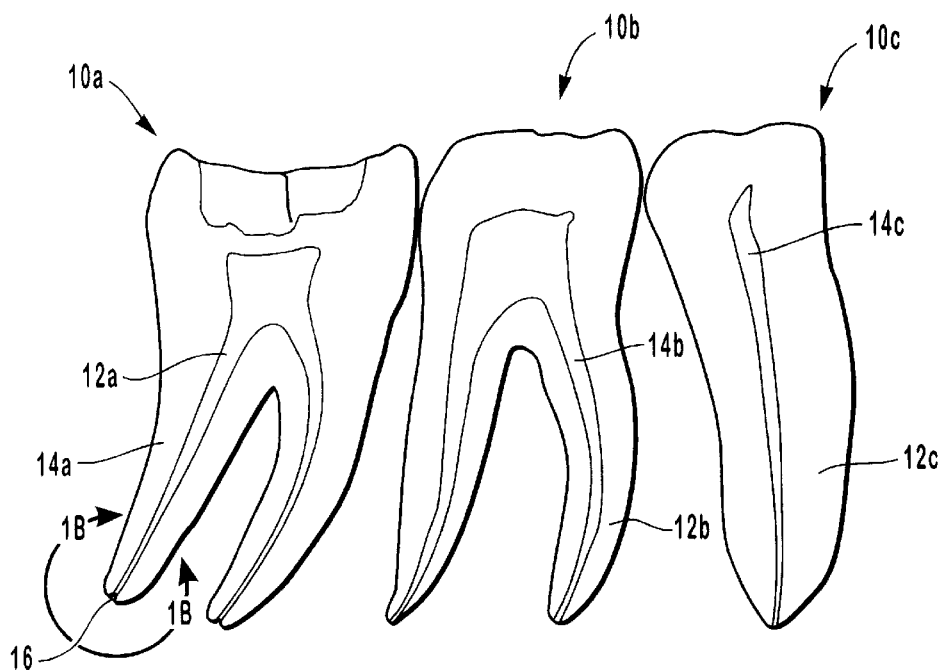
FIG. 1A is a perspective view of an x-ray image of several adjacent teeth taken in vivo.
Figure 1B:
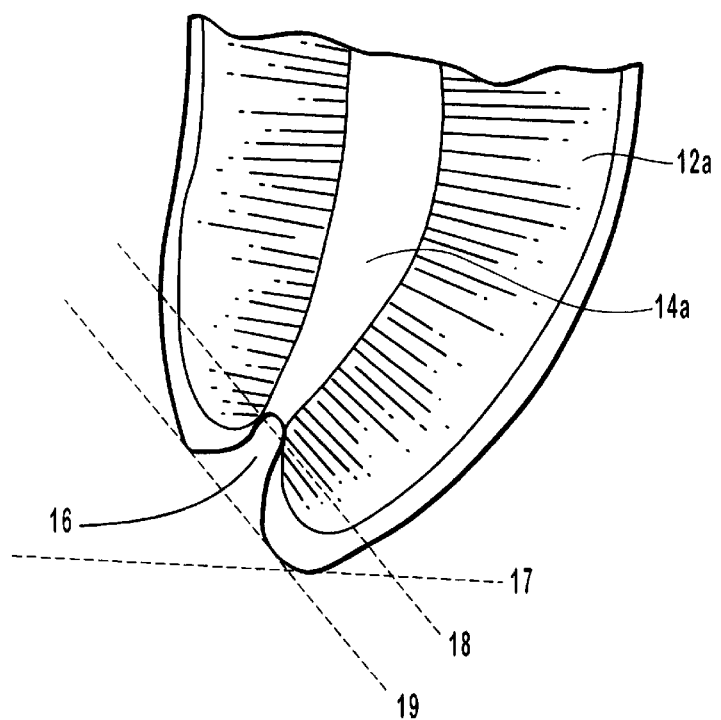
FIG. 1B is an enlarged perspective view of a root of a tooth shown in FIG. 1A.
Figure 2:
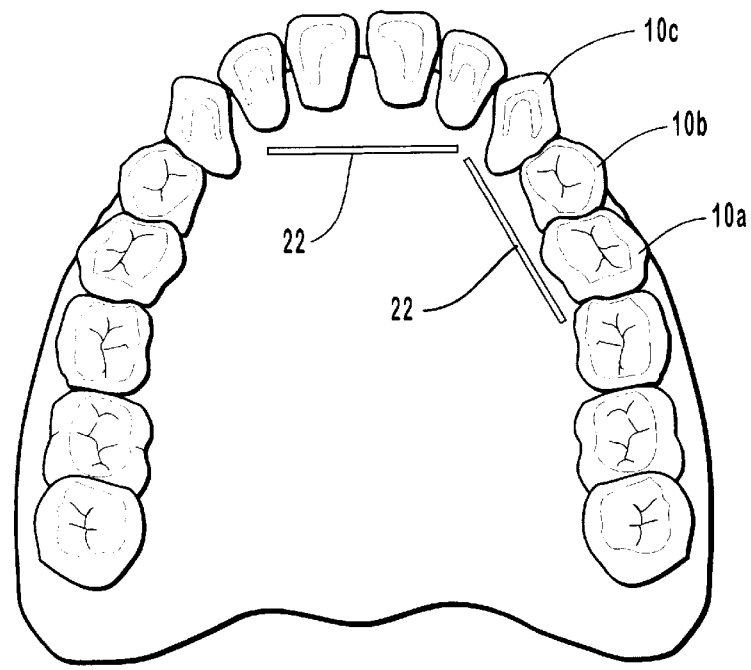
FIG. 2 is a perspective view of an x-ray film positioned adjacent to teeth to produce an image as shown in FIG. 1A.
Figures 3A, 3B, 3C:
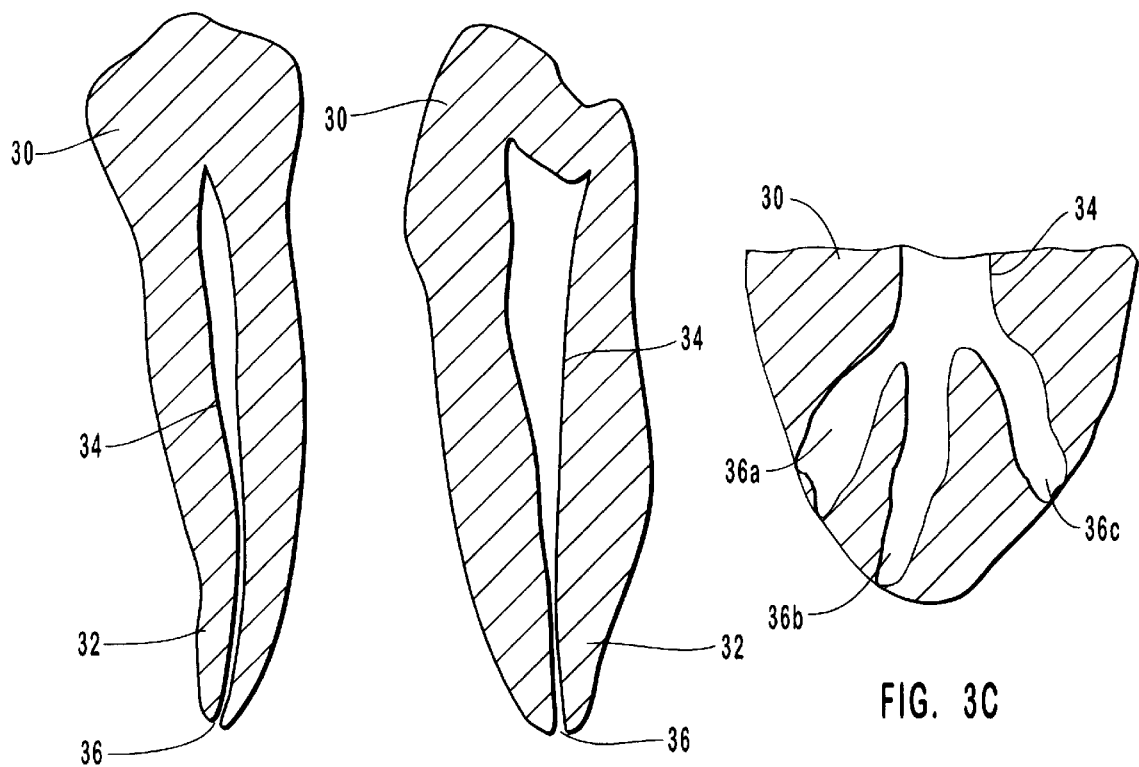
FIG. 3A is a longitudinal cross-sectional view of an extracted lower premolar to show the anatomy of the tooth from the buccal-lingual view.
FIG. 3B is a longitudinal cross-sectional view of the extracted lower premolar shown in FIG. 3A from the mesial-distal view.
FIG. 3C is an enlarged longitudinal cross-sectional view of an apex which divides into a delta configuration having three apical foramina. This configuration is presented as a possible alternative to the configuration of the tooth shown in FIG. 3B.
Figure 4A:
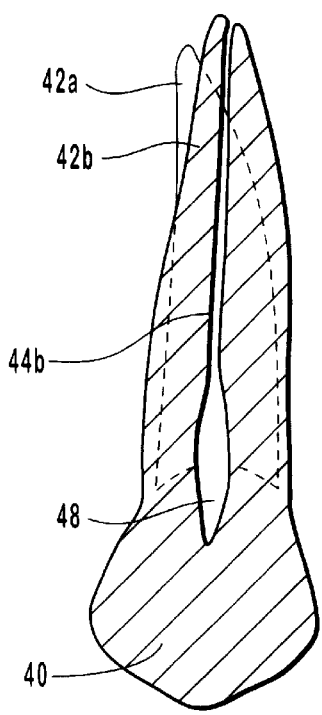
FIG. 4A is a longitudinal cross-sectional view of an extracted upper premolar to show the anatomy of the tooth from the buccal-lingual view.
Figure 4B:
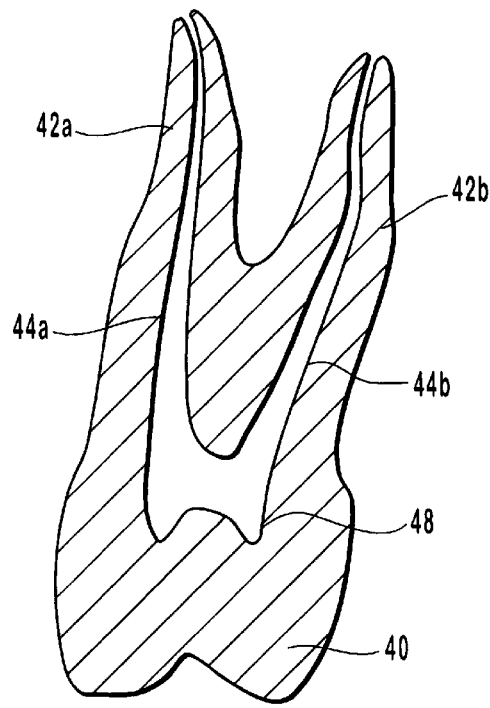
FIG. 4B is a longitudinal cross-sectional view of the extracted upper premolar shown in FIG. 4A from the mesial-distal view.
Figure 5A:
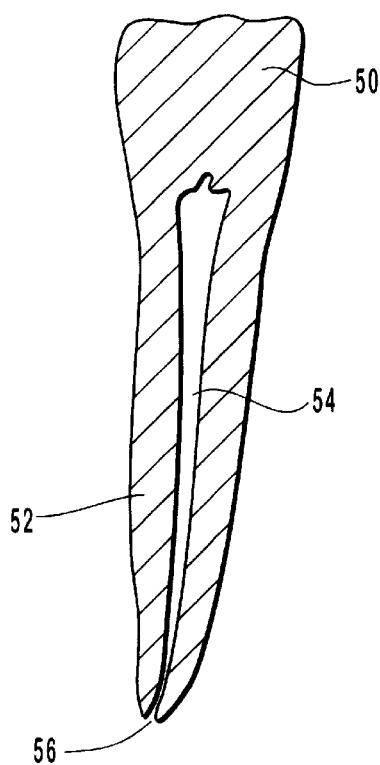
FIG. 5A is a longitudinal cross-sectional view of an extracted lower incisor to show the anatomy of the tooth from the buccal-lingual view.
Figure 5B:
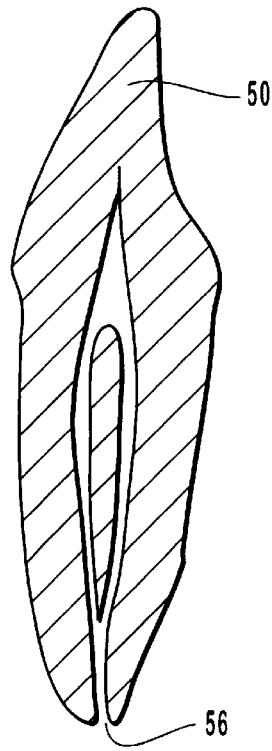
FIG. 5B is a longitudinal cross-sectional view of the extracted lower incisor shown in FIG. 5A from the mesial-distal view.
Figure 9A:
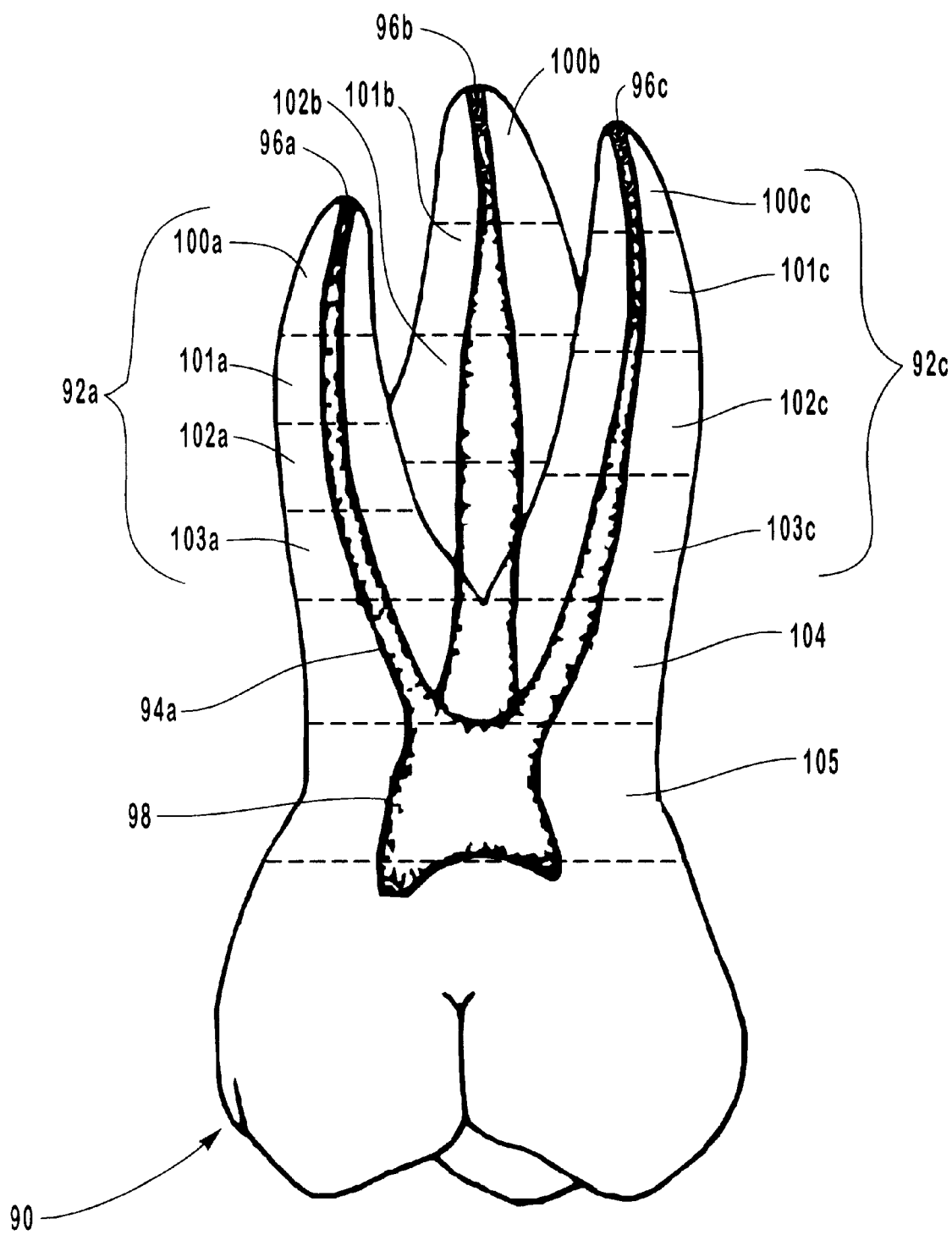
FIG. 9A is a schematic perspective view of an extracted maxillary right first molar with cutting lines which show the division of the tooth into transverse cross-sectional segments.

By instrumenting in the operative middle portion and the operative coronal portion before the cleaning the apical portion, the practitioner can use an instrument that is relatively flexible compared to the conventional instruments. As shown in FIG. 19B, which is a cross-sectional view taken along cutting line 19B—19B of tooth 240 in FIG. 1 9A, file 204a of file instrument 200a is sufficiently flexible to be flexed against any surface of operative middle portion 262 or operative coronal portion 260 and yet is sufficiently rigid to remain flexed against the surface during a cleaning motion such as a longitudinal motion, a rotational motion or a reciprocating rotational motion. The file is also sufficiently resilient that substantial deformation of the file does not occur due to the forces experienced during cleaning of the pulp material from the root canal.

File instrument 200a is shown in FIGS. 19A and 19B being moved in a longitudinal movement or up and down movement as well as being rotated while file 204a is flexed or arched to urge the file against the root canal surfaces. As shown, the configuration of the files used to clean the operative middle portion, and preferably the operative coronal portion as well, enable a practitioner to move the files around the perimeter or from side to side to contact the perimeter. Further, since the file is moved around the perimeter, the file has more than one center of motion during cleaning of the operative middle portion of the root canal, such as a pivot point or center of rotation, as the tip of the file or at least a part of the abrading portion does not generally remain primarily in one position. This is in sharp contrast to prior art methods which limited the practitioner to essentially rotating a conically shaped file to yield a cone shaped borehole.

Note the depicted movements in FIG. 19B occur in accordance with the present invention in the operative middle portion of all teeth and are not dicated by the outcropping of dentin identified as 244 in FIG. 19B which divides the canal. Stated otherwise, such movements enable the file to follow the contours of the root canal and are utilized in the operative middle portion of all root canals.

Due mainly to the configuration of the files, the contours of the operative coronal portion and the operative middle portion can be used during their cleaning by a practitioner as a guide for the movements of the files as the files are pushed against the surfaces of the root canal and simultaneously moved around the perimeter or periphery of the root canal until the practitioner has reached the beginning location of the cleaning and shaping process, or example, in root canals that are primarily noncircular, the files can be urged along one side and then along the next side wall in a manner such that the resulting cleaned and shaped root canal is generally widened but still primarily noncircular. In other words, there is essentially no borehole that obviously corresponds to the shape of the file.

Due to the ability to move the file as discussed the anatomy of the root canal remains substantially unaltered despite the cleaning of essentially all pulp material from the operative middle portion. The understanding that the final anatomy is guided by the shape of the original anatomy enables a practitioner to more confidently urge a file such as file 204a against all surfaces of root canal 252 and aggressively clean all of the surfaces of operative middle portion of the root canal since the likelihood of overly thinning the root canal or causing lateral perforations as shown in FIG. 15A–C and FIG. 15E is diminished. The assurance of the safety of the methodology is further bolstered by a general knowledge of wall thickness variations.

Another advantage of the configuration of operative middle portion instruments, such as file 204a shown in FIGS. 19A and 19B, is that the file can simultaneously abrade both operative coronal portion 260 and operative middle portion 262. The files can simultaneously abrade both portions as each file has an abrading portion along the entire length of the file. A primary benefit of simultaneously abrading both portions is the ability to further straighten the operative coronal portion while cleaning the operative middle portion.

Figure 13A:
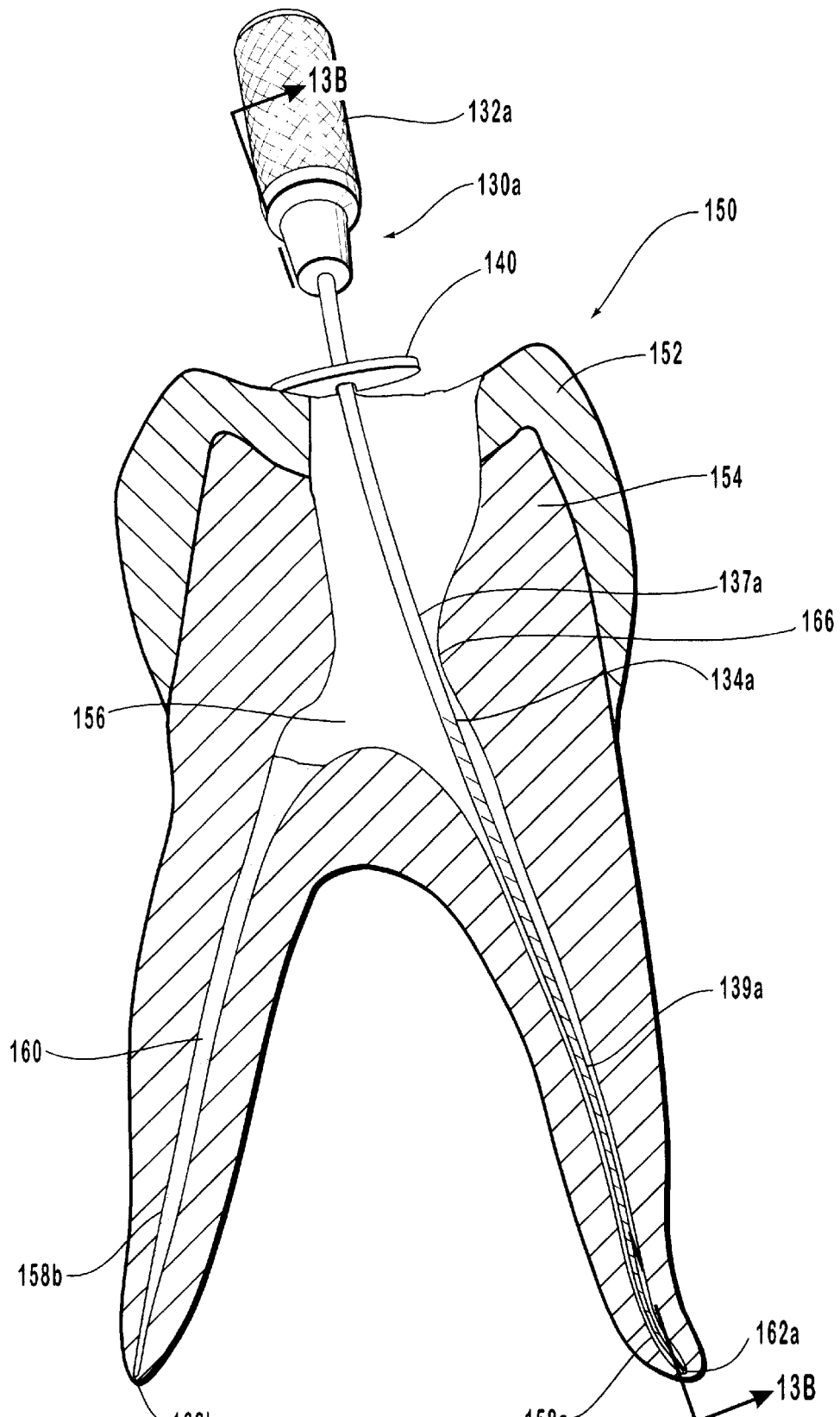
FIG. 13A is a longitudinal cross-sectional view of a tooth being cleaned lith a file instrument used in the step-back technique.
Figure 13B:
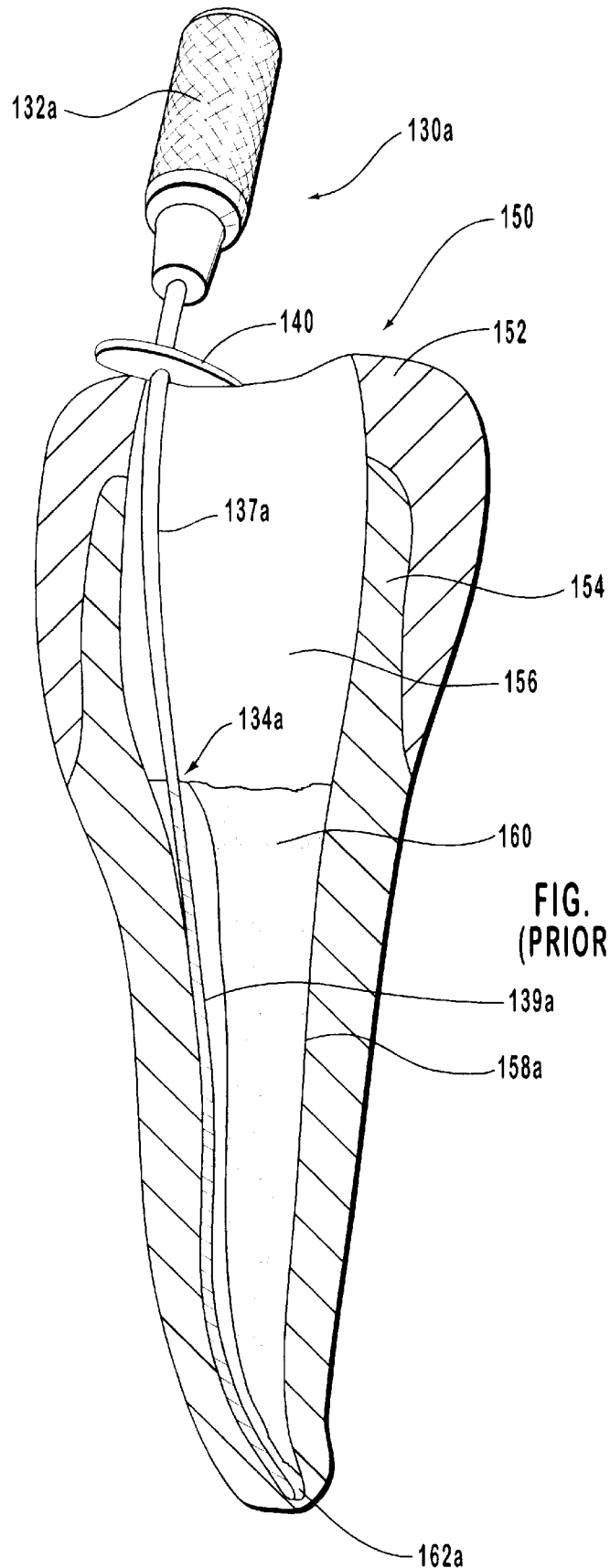
FIG. 13B is a longitudinal cross-sectional view of the tooth shown in FIG. 4A taken along cutting line 13B—13B, which shows the portion of the root canal which cannot be viewed in vivo.
Figure 14A:
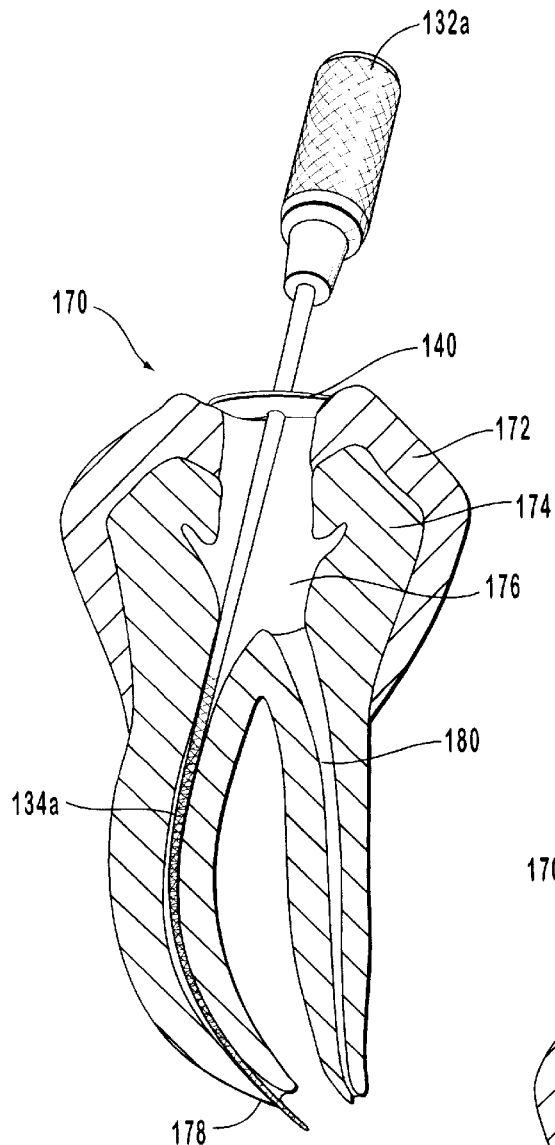
FIG. 14A is a longitudinal cross-sectional view of a tooth depicting apical perforation during cleaning of the root canal.
Figure 14B:
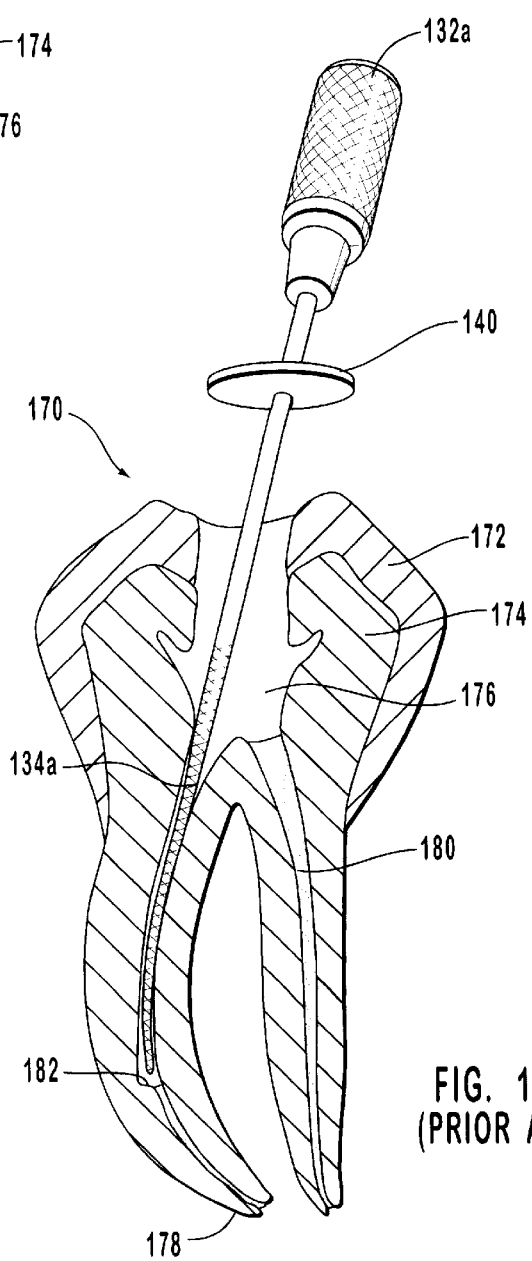
FIG. 14B is a longitudinal cross-sectional view of a tooth depicting ledging during cleaning of the root canal.
Figure 15A:
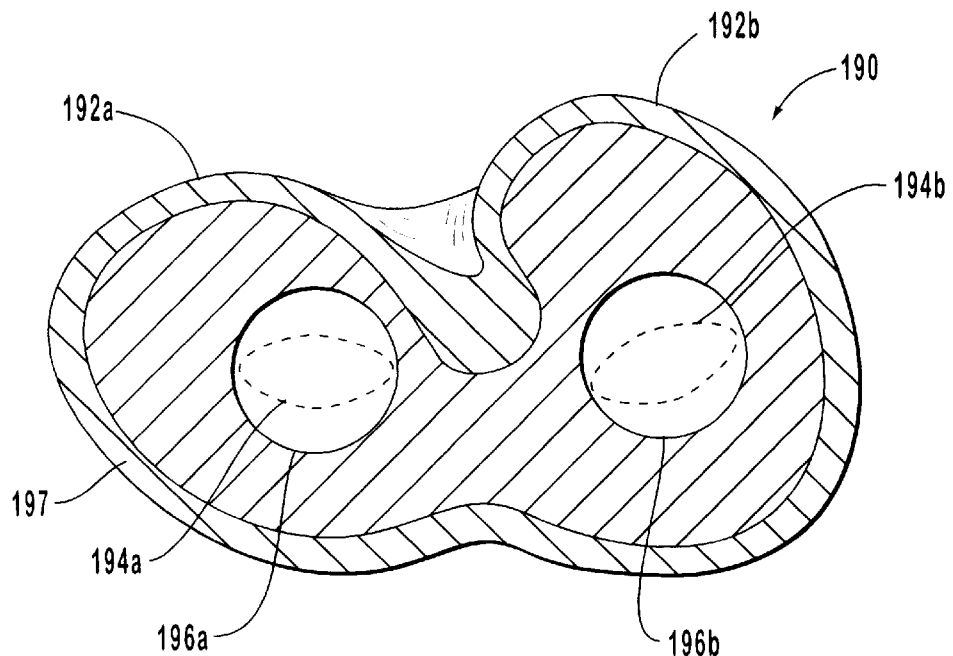
FIG. 15A is a transverse cross-sectional view of a tooth depicting a root canal cleaned by a prior art technique that has resulted in over thinning of the root canal.
Figure 15B:
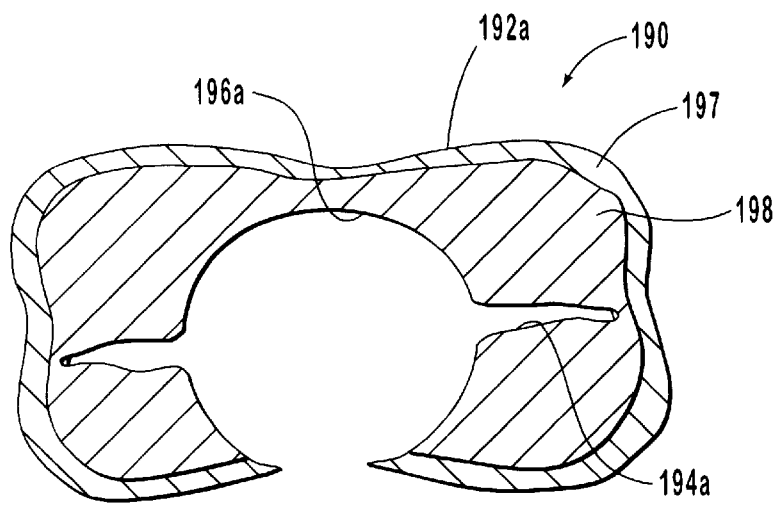
FIG. 15B is a transverse cross-sectional view of a tooth depicting a root canal cleaned by a prior art technique that has resulted in lateral perforation.
Figure 15C:
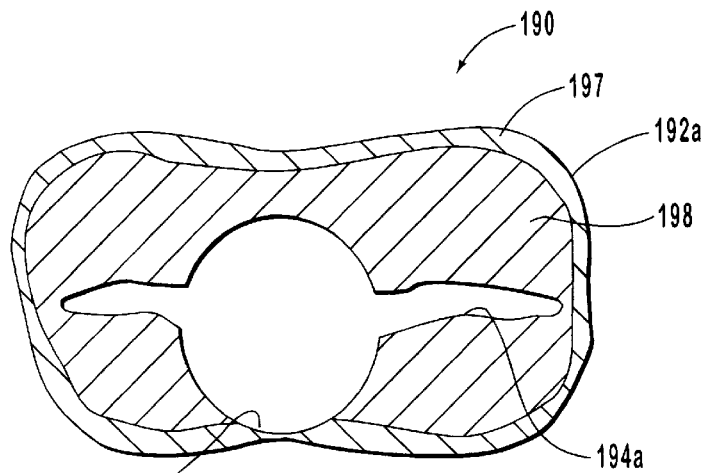
FIG. 15C is a transverse cross-sectional view of a tooth depicting a root canal cleaned by a prior art technique that has resulted in over thinning of the root canal.
Figure 15D:
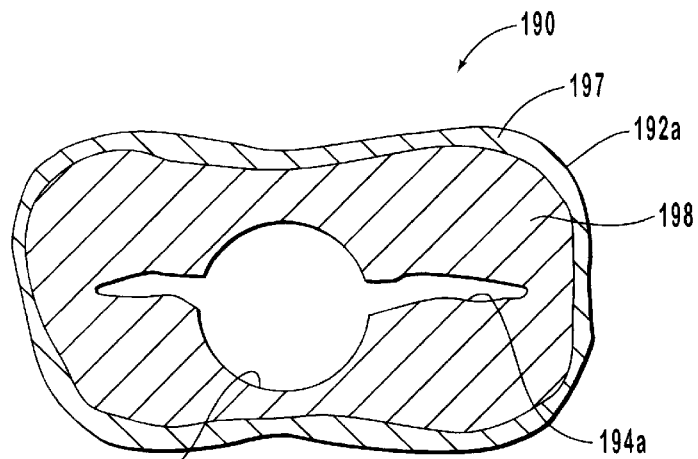
FIG. 15D is a transverse cross-sectional view of a tooth depicting a root canal cleaned by a prior art technique that has resulted in over thinning of the root canal.
Figure 15E:
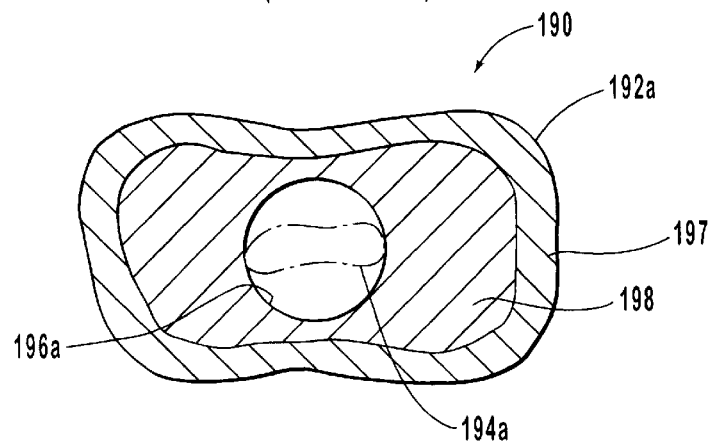
FIG. 15E is a transverse cross-sectional view of a tooth depicting a root canal cleaned by a prior art technique that has resulted in over thinning of the root canal.

Use of files in the operative middle portion which have an abrading portion along their entire length is in contrast to files formed in accordance with ISO standardization. ISO standardized files have abrading portions of up to 16 mm and the remainder of the file is a smooth shank. Examples of such files are shown in FIGS. 13A–B and 14A–B. Since such conventional files are inserted down to the apex, it is generally not possible to abrade any portion beyond the anatomical root canal. Since such conventional files frequently fail to remove interferences extending from the access or root chamber above the anatomical root canal, as shown in FIG. 13A, the instrument must bend around the interferences, thereby further increasing the likelihood of wall perforations, overthinning and failing to clean significant portions of the canal. It especially increases the likelihood of iatrogenic modifications resulting from the tip of the file.

File instrument 200a is preferably used in conjunction with an instrument designed for movement of endodontic file instruments. File instrument 200a can be continuously rotated in one direction only or file instrument 200a can be rotated in a reciprocating motion such that file instrument 200a rotates for example, clockwise for half of a revolution and then counterclockwise for half a revolution. A reciprocating motion is preferred as such motion enables the file to alternately engage material 250 and the walls of the operative middle portion of the root canal in a manner that removes material 250 and to then rotate in the opposite direction such that the file less aggressively engages material 250 and the operative middle portion walls, depending on the file design. Accordingly, rotating file instrument 200a in a reciprocating motion minimizes breakage of file 204a when file 204a encounters a surface that prevents rotation of file instrument 200a in a direction that enables cleaning and removal of material 250. File instrument 200a can also be vibrated or manipulated by hand. Hand milling is, however, more difficult and time consuming.

Figure 20A:
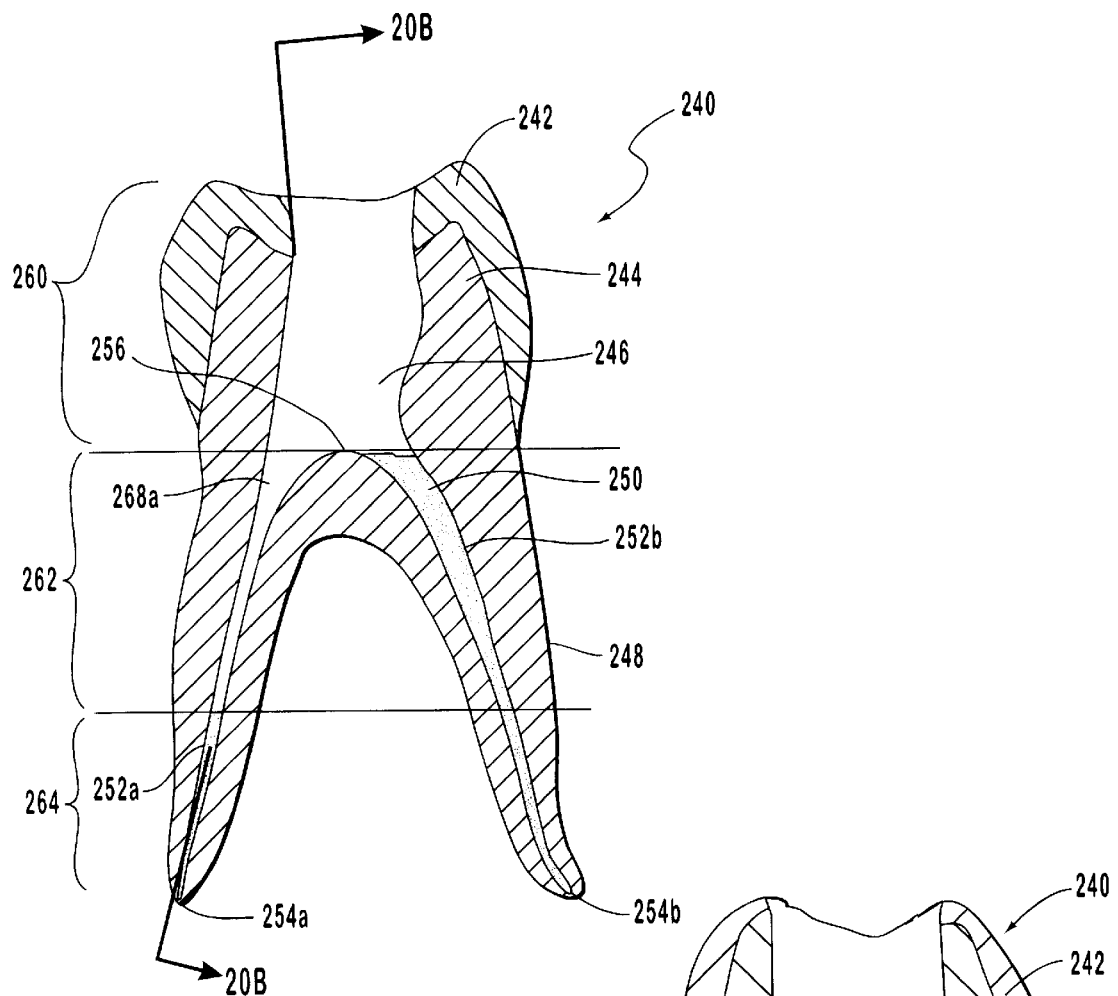
FIG. 20A is a longitudinal cross-sectional view of a tooth depicting a coronal portion of a root canal which has been cleaned by the removal of the pulp material.
Figure 20B:
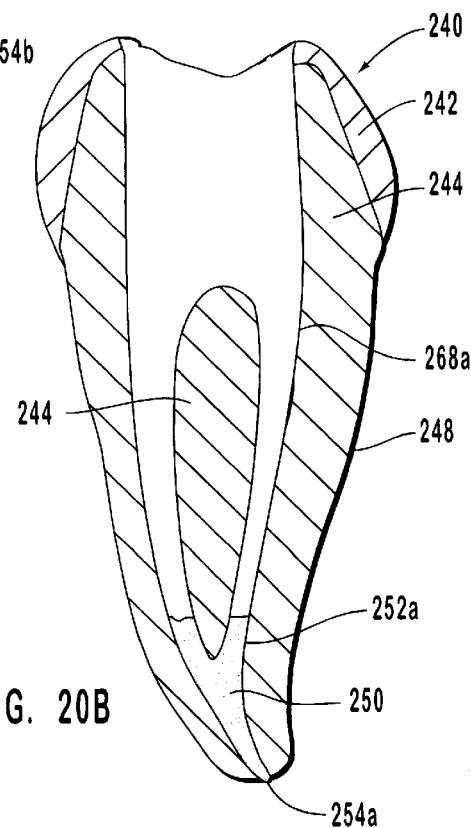
FIG. 20B is a longitudinal cross-sectional view of the tooth shown in FIG. 20A to show that essentially all pulp material has been removed from the coronal portion of the root canal.

FIG. 20A shows a cross-sectional view corresponding to the x-ray view after pulp material 250 has been removed from the operative middle portion 262 of root canal 252a and after the surfaces of root canal 252a have been shaped to yield shaped surfaces 268a of the root canal. FIG. 20B is a longitudinal cross-sectional view taken along cutting line 20B—20B of tooth 240 in FIG. 20B which clearly shows that essentially all pulp material has been removed and cleaned from operative middle portion 262.

Removal of pulp material 250 from operative middle portion 262 removes the majority of bacteria in the pulp canal since the majority of bacteria in an infected root canal is typically located in the operative middle portion. Not only is the greatest volume of bacteria in the operative middle portion but it is also believed that the concentration is greater in the operative middle portion. Since a certain minimum threshold must generally be reached for complications to arise due to microbial presence in a root canal, removal of the pulp material in the operative middle portion significantly reduces the likelihood of such complications.

By removing the majority of bacteria before cleaning the apical portion there is also less likelihood of exposing the surrounding tissue to bacteria due to overly thinning the root canal, perforation or extrusion of material from the canal. The greatest likelihood for the occurrence of complications such as over thinning of root canal walls, perforation or extrusion of material from the canal is in the apical portion. The apical portion is the most likely site for such complications as apical portions are more complex and delicate compared to the operative middle portions of teeth. Since such complications are most likely to occur in the apical portion, it is highly beneficial to have the material removed from the operative middle portion in order to minimize the amount of material that can come out of the root canal to cause problems. For example, in the event of an apical extrusion far less septic material may be expressed during instrumentation in accordance with present methodology than if the apical extrusion occcured as a result of cleaning in accordance with conventional methods wherein files are inserted to the apical portion before cleaning the operative middle portion. As a result, removal of the majority of bacteria before cleaning the apical portion increases the likelihood of successful root canal therapy in several ways compared with conventional methods.

To minimize the possible introduction of bacteria, it is preferable to utilize a kit such as the kit disclosed in copending U.S. patent application Ser. No. 09/014,765 entitled "Containing Device For Dental Tools with Foam Supporting Materials" and filed by Francesco Riitano on Jan. 28, 1998; the disclosure of which is hereby incorporated by reference. The kits preferably support a set of several instruments with identical lengths positioned to be easily grasped and preferably in an antimicrobial solution.

It should be noted that when there is an atresic root canal, it is preferable to use EDTA in a hydrosoluble gel and leave the composition in the canal for a few minutes. Similarly, for necrotic canals, it is advisable to work in a sodium hypochlorite saturated environment. For canals with living pulp, it is advisable to work in an environment saturated with 10% hydrogen peroxide.

After removing and cleaning essentially all pulp material from the operative middle portion of an operative root canal in conformance with the anatomical shape of the operative middle portion by flexibly moving an instrument within the operative middle portion, the apical root portion of the root canal can then be cleaned. However, it is preferable to improve the access into the apical root portion before cleaning the apical root portion of the root canal. More particularly, it is beneficial to widen the tract of the root canal to provide access for thin irrigation needles into the apical root portion so as to maintain the smear layer in solution within the apical root portion, thereby avoiding smear layer accumulation. Additionally, it is useful to maintain the debris derived from cleaning the root canal in suspension to avoid filling the apical portion of the root canal with a plug. If the apical portion becomes filled, there is an increased likelihood that the progress of the instrumentation may be stopped or that debris may be pushed out of the tooth. Accordingly, by widening the access to enable irrigation needles to deliver irrigants to the apical root portion, the apical root portion is more accessible to the subsequent apical cleaning instruments and the cleaning instruments are less likely to be blocked.

Thin irrigation needles typically have a diameter no smaller than about 0.30 mm so it may be necessary to increase the diameter of portions of the root canal up to about 0.35 mm or even up to about 0.40 mm, particularly within the region of the boundary between the operative middle portion and the apical root portion. Note that the diameter need only be slightly larger than a thin irrigation needle in order to provide adequate access.

While the diameters of some root canals within the region of the boundary between the operative middle portion and the apical root portion and even within the apical portion may already be large enough to enable irrigation needles to deliver irrigants as far as is necessary, it is generally necessary to widen the diameter within the apical portions or at least at the tops of the apical portions. Refer to Tables 2 and 3 in Example 1 for some average root canal diameters as measured 2 mm from the apex of each root canal. In Table 2 and Table 3, the largest average diameter in the apical portion for a particular type of tooth measured in the sampling was 0.54 mm while the smallest average was 0.18 mm. Note that the tip diameter of coronal portion instruments, as indicated hereinabove, typically range from 0.06 mm to 0.40 mm, more typically from about 0.08 mm to about 0.15 mm and most typically from about 0.08 mm to about 0.1 mm. In light of the apical portion diameters that are likely to be encountered, as indicated in Table 2 and Table 3, and the tip diameters of the instruments used to clean the operative middle portion just above the apical portion, it is apparent that widening is often necessary in-order to enable irrigation needles to adequately deliver irrigants.

It is not necessary for the entire apical portion to be widened up to about 0.35 mm or about 0.40 mm; just enough of the apical portion should be widened so that the irrigants can be delivered as needed. However, the length of files used to widen the apical portion is preferably sufficient to at least approximately reach the apex. Accordingly, the top of the abrading portion may be flared to enable the upper area of the apical portion to be widened up to about 0.40 mm while the tip diameter which is at or near the apex is preferably significantly smaller. Note that in addition to abrading at least the top of the apical portion, it may also be necessary to widen the diameter at the region of the base of the operative middle portion with the widening at the top of the apical portion.

Typically, the instruments used to improve the access into the apical portion, the apical portion access instruments, have the same lengths as the instruments subsequently used to clean the apical portion so that the entire apical portion is first widened and then cleaned. The instruments, however, have very different tip diameters and tapers along their respective abrading portions. The apical portion access instruments generally have much smaller tip diameters and much greater tapers than the instruments used to clean the apical portion for safe widening of apical portions. Refer to Example 2 and the accompanying FIGS. 36C–D for a discussion of specific instruments utilized and to observe the alteration of the apical portion after the apical portion widening phase and the apical portion cleaning phase.

Note that before widening the apical portion of the root canal, it is preferable to make a predetermination of the desired diameter. This predetermination is preferably made in light of average diameters, wall thicknesses, etc. for the particular root canal being cleaned. As indicated hereinabove, Table 2 and Table 3, hereinbelow in Example 1, provide a sampling of such morphometric data.

An example of a set of instruments designed for improving the access into the apical root portion is shown in FIG. 21. The set comprises four file instruments 270a, 270b, 270c and 270d. Each file instrument comprises a handle 272 connected to a file 274. Each file 274 has a top end 276 where the file joins handle 272. When utilized to widen the access into the apical root portion of a root canal, file 270a is first introduced followed sequentially by file 270b, 270c and then 270d. Each file terminates at a tip 278 located opposite top end 276. A file instrument such as file instrument 270a or a set of file instruments such as 270a, 270b, 270c and 270d comprises a second endodontic instrument means for improving access into the apical root portion after the pulp material has been essentially removed from the operative middle portion by the first endodontic instrument means.

Each file 274 of the file instruments designed for improving access to the apical root portion of a root canal is configured to have an abrading portion 279 along at least a portion of the length of file 274. The entire length of each file 274 can be configured with an abrading portion 279, however, abrading portion 279 preferably extends from tip 278 part way upward towards top end 276 such that the remainder of file 274 is relatively smooth. More particularly, each file is preferably configured with an abrading portion along less than about half of the length of the file and more preferably about one-third of the length between tip 278 and top end 276. Accordingly, the abrading portion may have any suitable length such as 3 mm or 10 mm; however, the abrading portion in a preferred configuration is about 5 mm or about 6 mm. The abrading portions as well as the tips can have a similar or identical configuration to the abrading portions and tips of the files disclosed herein for cleaning either the operative middle portion of the root canal or the apical root portion. However, the abrading portions and tips are preferably rounded as shown in FIG. 21.

As indicated above, the length of a file such as files 274a, 274b and 274c is preferably sufficient such that when the file is inserted into the root canal the tip can at least approximately reach the apex and the abrading portion 279 of the file can improve the access into the apical portion of the root canal. Although files used to improve the access into the apical root portion may be long enough to approximately reach the apex, the files can be used to improve the access as long as the files can reach the bottom of the operative middle portion and the top of the apical root portion. Such file lengths are typically within a range from about 8 mm to about 35 mm, more typically in a range from about 14 mm to about 35 mm and most typically in a range from about 12 mm to about 33 mm. The length of the abrading portion is generally within a range from about 1 mm to about 35 mm, more preferably in a range from about 2 mm to about 16 mm and most preferably in a range from about 3 mm to about 6 mm. The abrading portion is preferably long enough so that the entire apical portion can be abraded as well as at least the bottom of the operative middle portion.

In a set of instruments used to improve the access into an apical root portion, the file tips of the instruments preferably all have about the same diameter as shown in FIG. 21 at 278a–d. The diameter of the tips is generally within a range from about 0.06 mm to about 1 mm, however, the tips preferably have a diameter of about 0.08 mm. In a less preferred embodiment, the tip diameter of each file may also increase sequentially.

As shown in FIG. 21, the diameter of the abrading portions 279a–d increases from the tips 278a–d towards the top of the abrading portions. The diameter of the abrading portion at the top is preferably within a range from about 0.1 mm to about 0.4 mm and is more preferably in a range from about 0.2 mm to about 0.35 mm. As shown in FIG. 21. each successive file has an abrading portion. 279a, 279b, and 279c which is successively larger in diameter at the top of the abrading portion than the abrading portion of the preceding file. Accordingly, a set may have files with abrading portions having the following respective top diameters: about 0.2 mm, about 0.25 mm, about 0.3 mm and about 0.35 mm. Each abrading portion in such a set has a different taper as is shown in FIG. 21.

FIG. 21, however, also shows that the taper of the smooth or shank portions above the abrading portions may have essentially the same taper so that the taper of the shank portions remains essentially constant as the different files in the set are sequentially inserted. However, the shanks portions may have any suitable configuration. Accordingly, the diameter at top end 276, in addition to being greater than the diameter of the abrading portion, can also be equal to or less than the diameter of abrading portion 279 or tip 278.

Figure 34A:
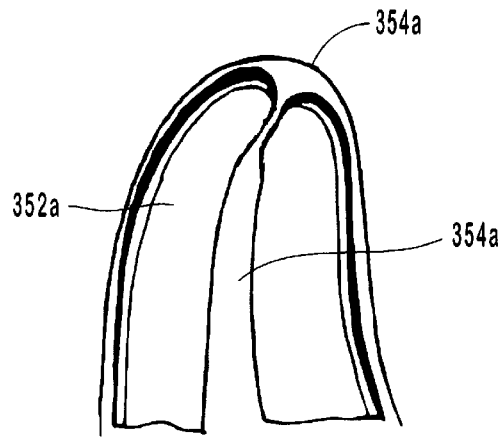
FIG. 34A is an enlarged perspective view of x-ray image of a root canal of a vital tooth without periapical rarefaction.
Figure 34B:
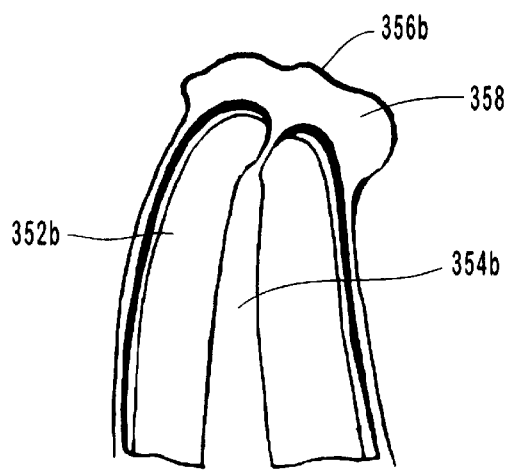
FIG. 34B is an enlarged perspective view of an x-ray image of a root canal of an infected root canal without periapical rarefaction.
Figure 34C:
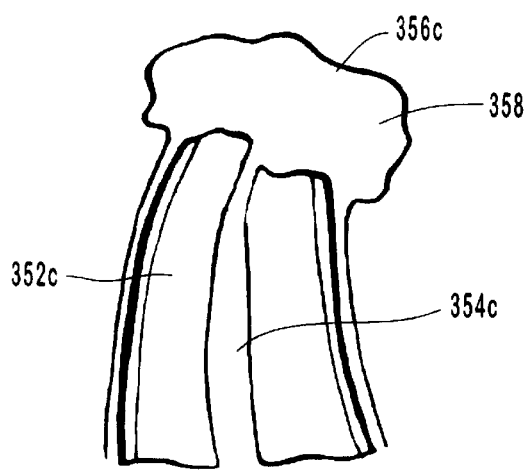
FIG. 34C is an enlarged perspective view of an x-ray image of a root canal of an infected root canal with apical and periapical resorption.

Before the apical root portion is cleaned, it is preferable to obtain further x-ray images while an instrument is inserted into a root canal to determine the desired working length of the instrument. In establishing the working length, the state of the apex and the periapical tissues should also be considered. The states most frequently shown in radiography are shown in FIGS. 34A–C wherein the apical portion of root canals 354a–c of roots 352a–c are depicted. FIG. 34A depicts a root canal 354a of a vital tooth without periapical rarefaction as shown by the normal border with the bone at 356a. FIG. 34B depicts an infected root canal 354b without periapical rarefaction as shown by radiolucency 358b. FIG. 34C depicts an infected root canal 354c with apical and periapical resorption as shown by radiolucency 358c. If the practitioner identifies the condition of the root canal as being that depicted in FIGS. 34A or FIG. 34B, then the working length of an instrument used to clean the apical root portion is in a range from about 0 to about 2 mm less than the distance from the occlusal surface to the radiographic apex of the tooth. However, if the root canal condition is infected and has apical and periapical resorption as depicted in FIGS. 34C, then the apical root portion is cleaned up to about 1.5 mm or about 0.5 mm from the radiographic apex or more particularly about 1 mm.

An example of a set of instruments designed for removing and cleaning essentially all remaining pulp material from the apical portion of a root canal is shown in FIG. 22. The set comprises three file instruments 280a, 280b and 280c. Each file instrument comprises a handle 282 connected to a file 284. Each file 284 has a top end 286 where the file joins handle 282. When utilized to clean the apical root portion of a root canal, file 280a is first introduced into the apical root portion followed by file 280b and then 280c. Each file terminates at a tip 288 located opposite top end 286. A file instrument such as file instrument 280a or a set of file instruments such as 280a, 280b, and 280c comprises a third endodontic instrument means for removing and cleaning essentially all remaining pulp material from the apical root portion after the pulp material has been essentially removed from the operative middle portion.

Tips 288a–c can have any configuration, however, tips 288a–c preferably have minimal cutting capability to decrease the likelihood of ledging. An example of a suitable configuration for tips 288a–c that is designed to minimize the cutting ability of the tips is that of the round tip shown in FIG. 17B.

Each file 284 of the file instruments designed for cleaning the apical root portion of a root canal is configured to have an abrading portion 289 along at least a portion of the length of file 284. The entire length of each file 284 can be configured with an abrading portion 289, however, abrading portion 289 preferably extends from tip 288 part way upward towards top end 286 such that the remainder of file 284 is relatively smooth. More particularly, each file is preferably configured with an abrading portion along less than about half of the length of the file and more preferably about one-third of the length between tip 288 and top end 286. The abrading portion 289 can have a similar or identical configuration to the abrading portion of the file or files used to clean the operative middle portion of the root canal or the files used to improve the access into the apical root portion.

The length of a file such as files 284a, 284b and 284c is sufficient such that when the files are inserted into the root canal the tips can at least approximately reach the apex and the abrading portion 289 of the files can substantially contact and clean the pulp material in the apical portion of the root canal. Such file lengths are generally within a range from about 8 mm to about 35 mm, more typically in a range from about 14 mm to about 35 mm and most typically in a range from about 12 mm to about 33 mm. The length of the abrading portion is generally within a range from about 1 mm to about 35 mm, more preferably in a range from about 2 mm to about 16 mm and most preferably in a range from about 3 mm to about 6 mm.

The diameter of the abrading portion is generally within a range from about 0.06 mm to about 0.4 mm. As shown in FIG. 22 each successive file has an abrading portion, identifed as 289a–c, which is successively larger in diameter at the top of the abrading portion than the abrading portion of the preceding file.

The diameter of the tips 288a–c of each file may be increased incrementally such that each sequentially utilized cleaning instrument has a slightly larger tip diameter than the preceding instrument as shown in FIG. 22 and FIG. 23 or the tips diameters may be about equal in diameter like the tips shown in FIG. 21.

Additionally, the taper of files 284 from tip 288 to the top end of the abrading portion may be constant as shown in FIG. 22. The taper may also increase from file to file like the files shown in FIG. 21 or like instruments shown in FIG. 35 in set 470. The diameter at top end 286 is shown being greater than the diameter of the abrading portion. However, the diameter at the top end of the tile can also be equal to or less than the diameter of abrading portion 289 or tip 288.

The abrading portion 289 of each file 284 of file instruments 280 is formed by twisting a blank so as to form a spiral. Files having such spiral-type abrading portions are preferred. The abrading portion 289 preferably has few spirals such that the action of abrading portion 289 against the walls or surfaces of the apical portion of the root canal is relatively gentle. Such an abrading portion is less aggressive as fewer spirals results in tines that have a wider angle.

FIG. 23 depicts an alternative embodiment of files configured for cleaning the apical portion of a root canal. The set of instruments depicted in FIG. 23 comprises three file instruments 290*a*, 290*b* and 290*c*. Each file instrument comprises a handle 292 connected to a file 294. Each file 294 has a shank portion 296 above an abrading portion 298. Shank portion 296*a* has substantially the same diameter along its length and the diameter of shank portion 296*a* is approximately the same as the diameter of shank portion 296*b* and 296*c*. The diameter of abrading portion 298*a* is essentially constant along the length of abrading portion 298*a*. Similarly, abrading portions 298*b* and 298*c* also have substantially constant diameters. The diameter of abrading portion 298*b* is larger than the diameter of abrading portion 298*a* and the diameter of abrading portion 298*c* is larger than the diameter of abrading portion 298*b*.

FIG. 24 depicts an additional alternative embodiment of files configured for cleaning the apical portion of a root canal. The set of instruments depicted in FIG. 24 comprises three file instruments 200*a*, 200*b* and 200*c*. Each file instrument comprise a handle 202 connected to a file 204. Each file 204 has a shank portion 206 above an abrading portion 208. Shank portion 206*a* has substantially the same diameter along its length and the diameter of shank portion 206*a* is approximately the same as the diameter of shank portions 206*b* and 206*c*. Each abrading portion 208 extends from each respective shank portion 206 with a shape that is generally elliptical. Additionally, the width of each successive abrading portion 208 is larger than that of the preceding abrading portion. More specifically, the width of each successive abrading portion is larger at its midpoint than at the midpoint of the preceding abrading portion.

Figure 25:
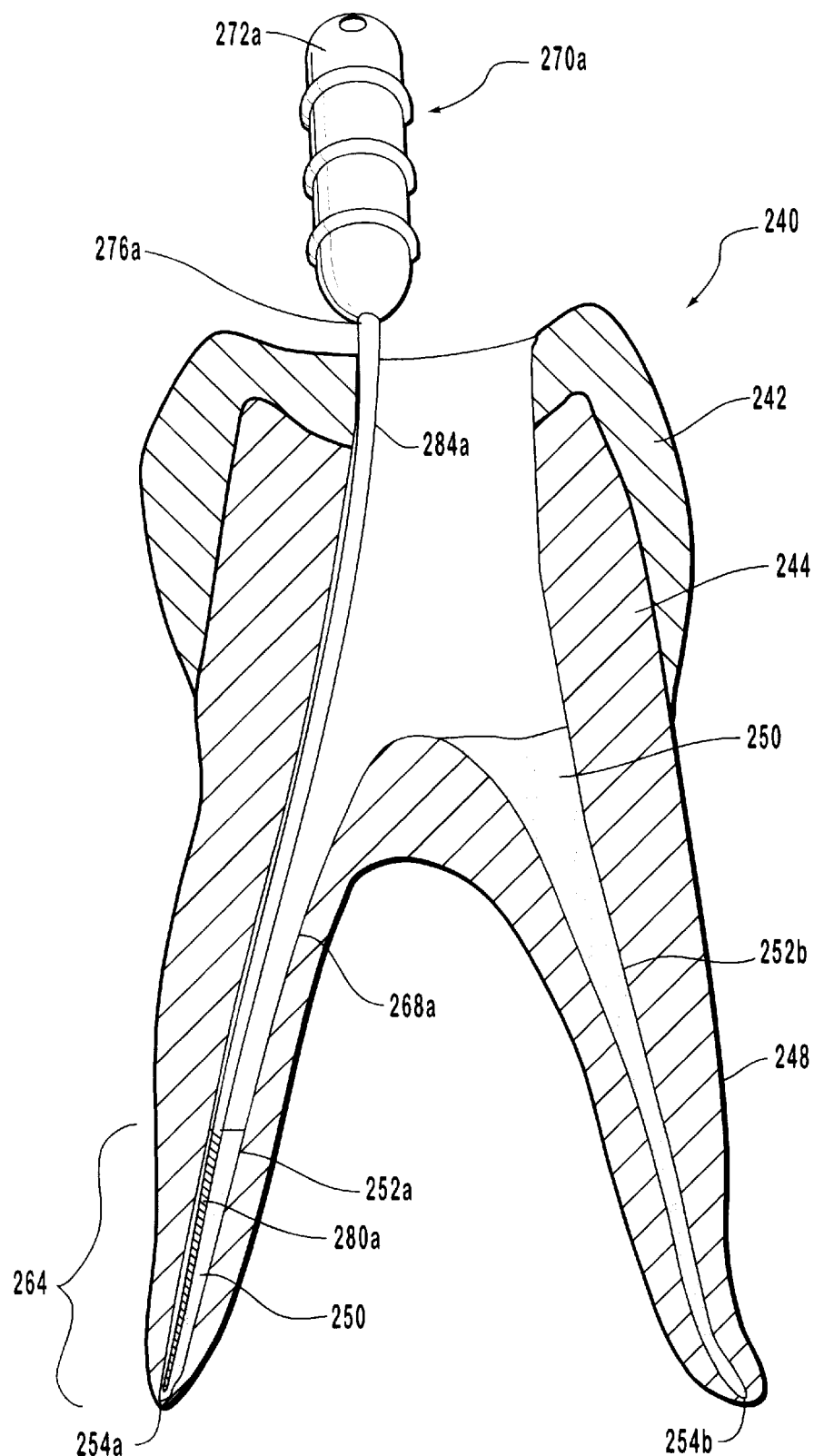
FIG. 25 is a longitudinal cross-sectional view of a tooth with a file inserted into a root canal having a length that is sufficient to reach the apex.

FIG. 25 depicts file 284*a* inserted into apical portion 264 of root canal 252*a*. The apical root portion file instruments are generally moved in a different pattern compared to the operative middle portion file instruments due primarily to the different perimeter anatomies of the two portions. A root canal generally becomes more cylindrical towards the apical portion such that a root canal that has a perimeter anatomy that is essentially elliptical in shape within the operative middle portion tapers to an essentially cylindrically shaped perimeter anatomy within the apical portion.

An elliptical perimeter anatomy typically requires that the practitioner move the file around the perimeter and/or flex the rotating file against the surfaces or walls in a milling motion such that the tip is moved to many locations around the perimeter. Due to the more cylindrical anatomy of an apical root portion, it becomes much less necessary, and virtually impossible to flex a rotating file in a milling motion. It is generally adequate to merely rotate the file within the apical root portion and/or move the file in a longitudinal motion. More specifically, after the file reaches the apex or approximately reaches the apex, the file is preferably moved upward while simultaneously being rotated, and it is withdrawn in order to be cleaned before being reintroduced.

Since file 284*a* is generally not moved around the perimeter as in cleaning the operative middle portion, the center of motion, such as the center of rotation, of file 284*a* generally corresponds with the center of the root canal. In contrast, the center of motion when the operative middle portion is cleaned is at various locations as the file is moved around the root canal.

The files used to clean the apical root portion can be designed for primarily longitudinal movement, rotational movement or combinations thereof. Since it is generally not necessary to flex a file when cleaning the apical root portion as the apical root portion is typically rounder than other sections of a root canal, apical root portion files need not necessarily have the same properties as the operative middle portion files in terms of flexibility, rigidity and resilience. The files used to clean the apical portion are, however, preferably sufficiently flexible to adjust to the anatomy or structure of a root canal in a manner that enables the tip of the file to reach the apex. The files also preferably have sufficient rigidity to apply pressure against the walls or surfaces of the root canal as the abrading portion of the file is urged against the walls of the root canal and simultaneously moved in a cleaning motion even after the file has moved throughout the length of the root canal. Additionally, a file configured for use in an apical root portion preferably has adequate resilience to avoid being substantially deformed as the file passes through a root canal and also as the abrading portion is applied against the walls of the root canal.

Figures 26A, 26B:
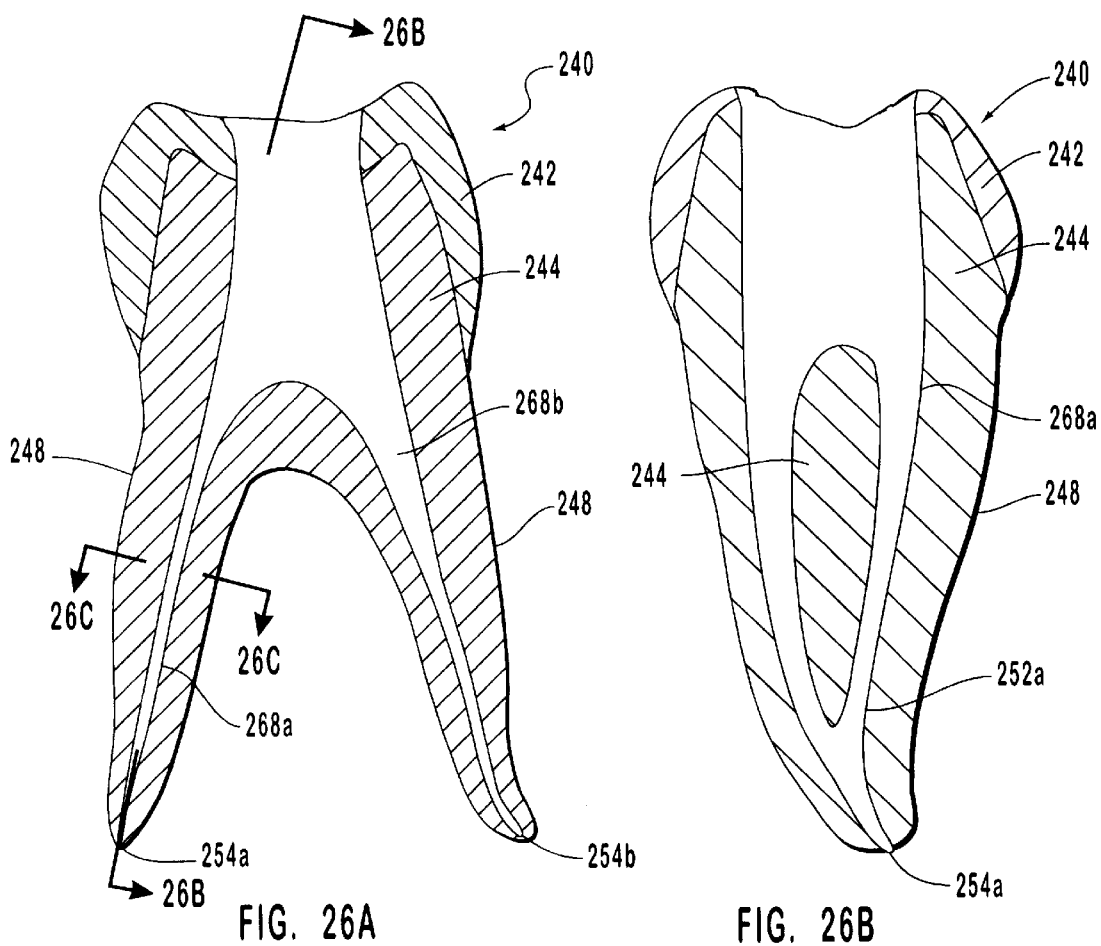
FIG. 26A is a longitudinal cross-sectional view of a tooth with a root canal that has been cleaned.
FIG. 26B is a longitudinal cross-sectional view of the tooth shown in FIG. 26A taken along cutting line 26B—26B to show that essentially all pulp material has been removed from the root canal.

FIG. 26A depicts a longitudinal cross-sectional view of tooth 240 after both root canals 252*a* and 252*b* have been cleaned. FIG. 26B depicts a cross-sectional view of tooth 240 taken along cutting line 26B—26B in FIG. 26A. From the view shown in FIG. 26B, it is clear that essentially all pulp material 250 has been removed from root canal 252*a*.

Figure 26C:
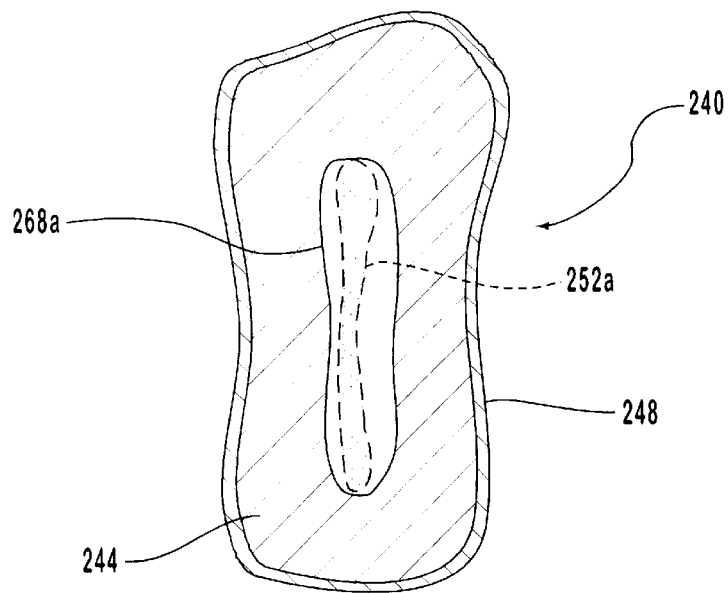
FIG. 26C is an enlarged transverse cross-sectional view of the tooth shown in FIG. 26A taken along cutting line 26C—26C to show that the anatomy of the root canal has not been substantially altered by the cleaning thereof and to show the shaping of the canal in preparation of filling the root canal.

FIG. 26C is a transverse cross-sectional view of root canal 252*a* taken along cutting line 26C—26C in FIG. 26A through cementum 248 and dentin 244 to depict the configuration of the cleaned and shaped root canal. The view shown in FIG. 26C shows in phantom lines the original configuration of the perimeter of the pulp canal 252*a* and the configuration of the cleaned and shaped walls 268*a*.

While the root canal is cleaned, it is also generally simultaneously shaped for subsequent filling with a filling material such as gutta percha. Cleaning and shaping a root canal, such as pulp canal 252*a*, to yield a cleaned and shaped root canal, such as shaped walls 268*a*, generally necessitates the widening of portions of the pulp canal and smoothing some contours of the pulp canal to yield a wider and smoother canal. The amount of dentin removed during the cleaning and shaping is preferably no more than just sufficient to adequately shape the root canal for subsequent filling.

Figure 8:
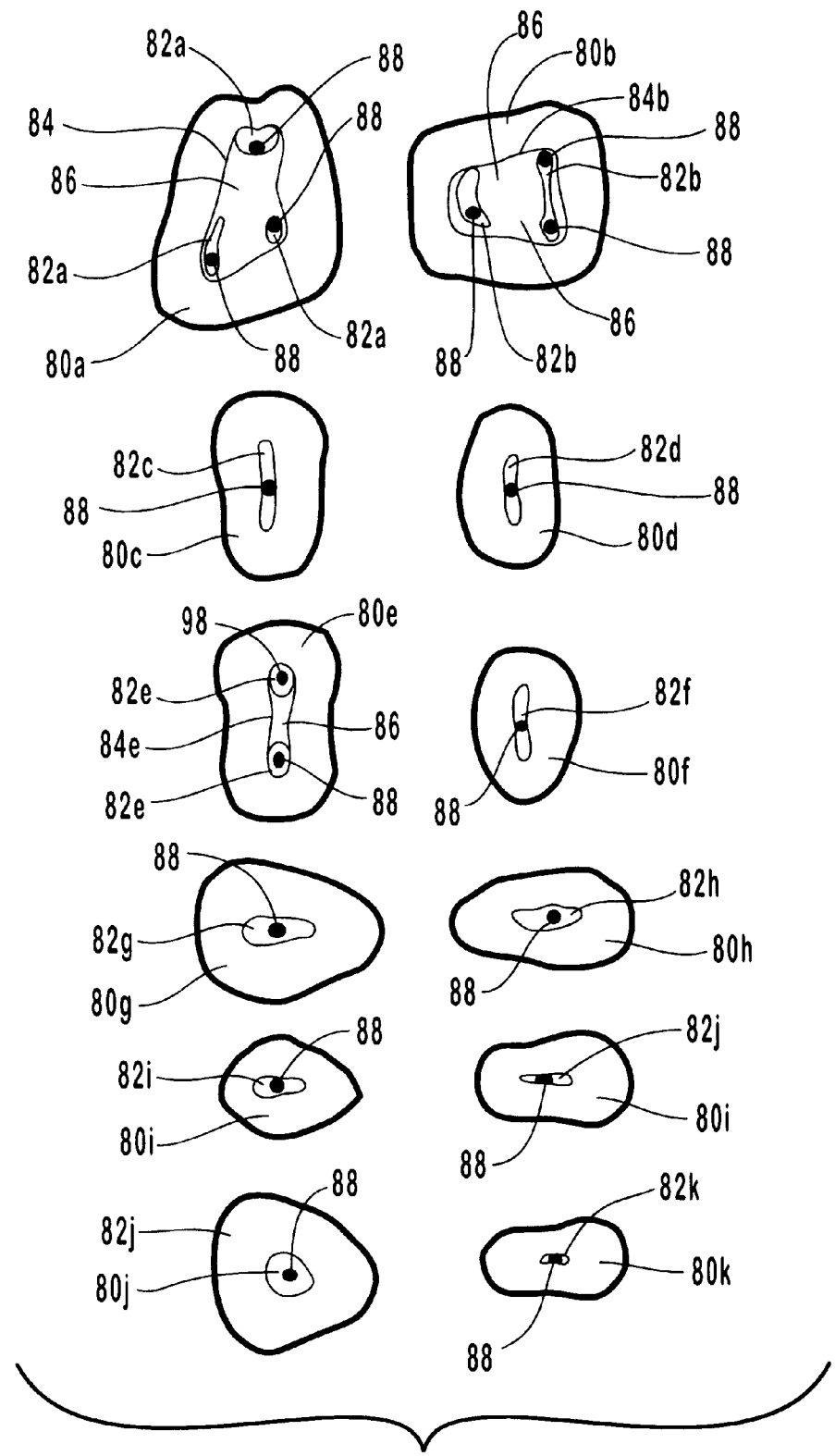
FIG. 8 is a cross-sectional view of extracted teeth which have been cut along into transverse cross-sectional segments to show the anatomy of various root canals.
Figure 9B:
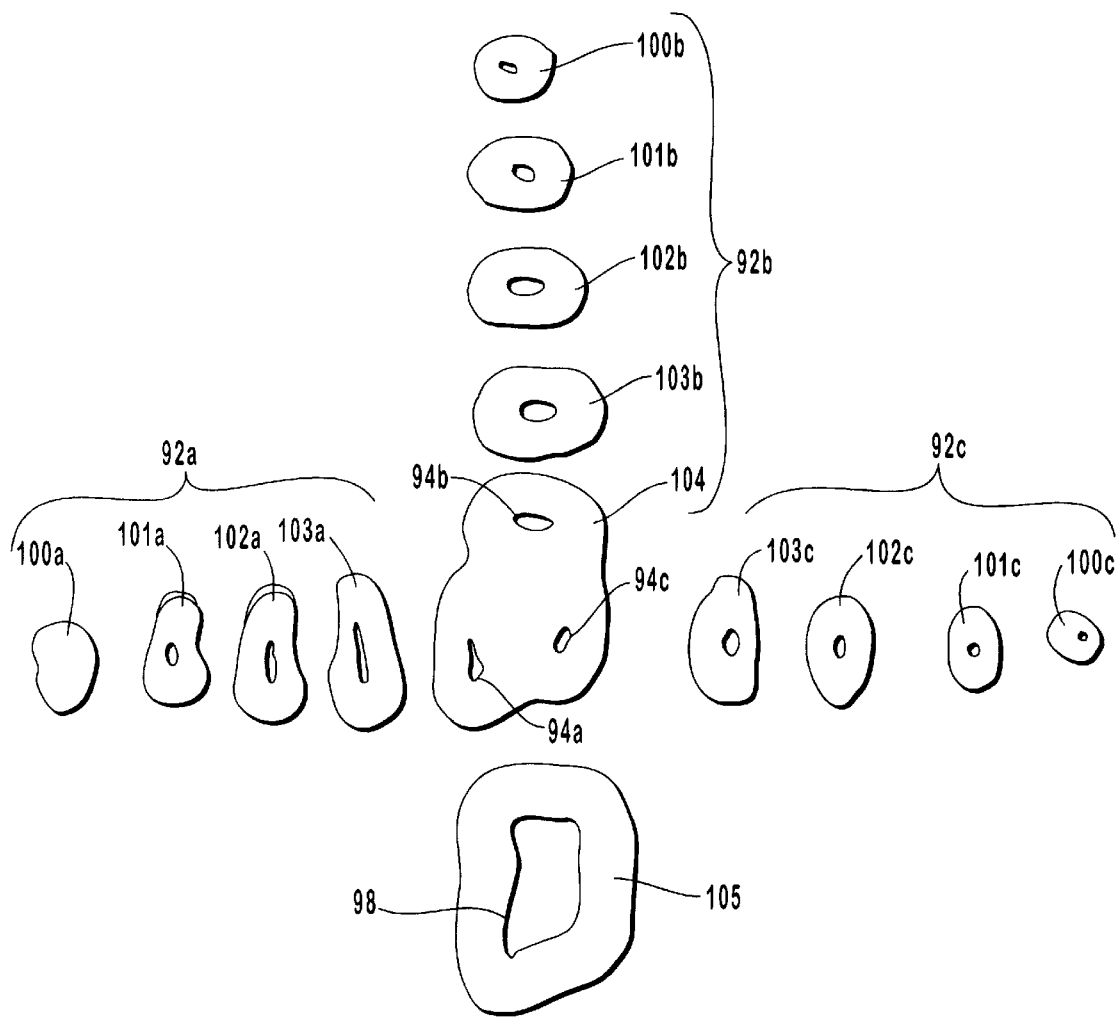
FIG. 9B depicts the cross-sectional segments of the molar shown in FIG. 9A to clearly show the variations of the root canals.
Figure 10A:
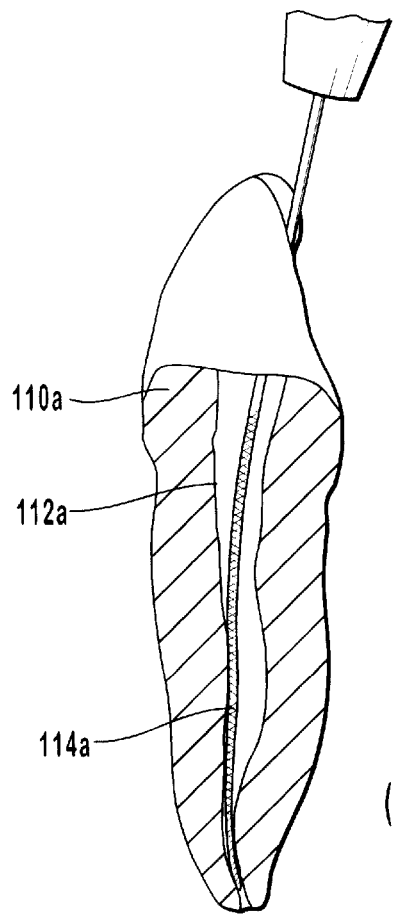
FIG. 10A is a perspective view of a prior art instrument cleaning a tooth that has been partially cut-away to reveal the inability of the instrument to clean the root canal.
Figure 10B:
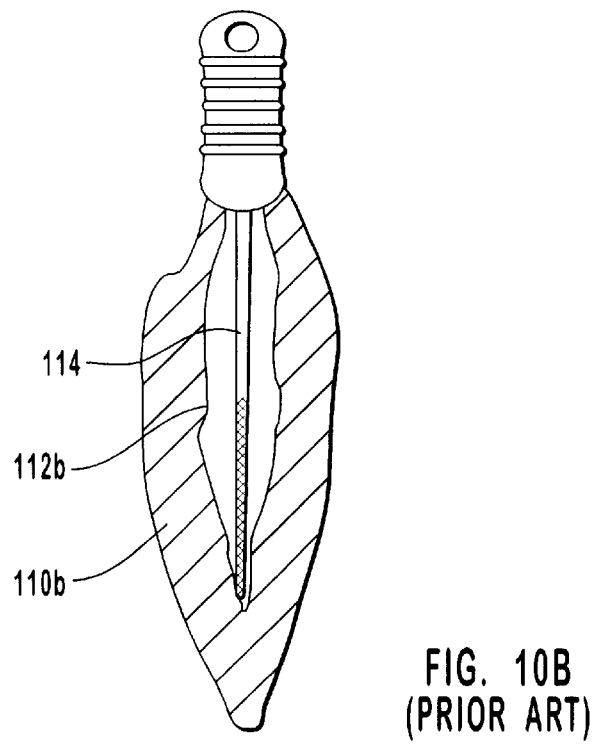
FIG. 10B is a perspective view of a prior art instrument cleaning another tooth that has been partially cut-away to reveal the inability of the instrument to clean the root canal.

Because the perimeter of the root canal is followed during cleaning and shaping of the root canal, the original anatomy of the root canal or shape of the perimeter is substantially maintained. According, when the original perimeter is, for example, generally elliptical such as the cross-sectional shape of pulp canal 252*a*, the resulting cleaned and shaped root canal has a perimeter that is still generally elliptical such as shaped walls 268*a* as shown in FIG. 26C. Similarly, if the original shape of the perimeter of a root canal as seen from a transverse cross-sectional view, such as the anatomies or perimeter configurations shown in FIGS. 7, 8 and 9B, is generally circular, laminar or tear shaped, then the cleaned and shaped walls will also be generally circular or tear shaped. In other words, the original anatomy of the root-canal controls the shape of the resulting cleaned and shaped anatomy due to the cleaning techniques enabled by the present invention.

In contrast, prior art methods yield a final anatomy that is dictated by the shape of the instrument. As shown in FIGS. 15A–F, prior art methods result in an anatomy with a significant footprint from the instrument without even cleaning all of the perimeter of the root canal. In addition to failing to fully clean the root canal, the tooth can be overly thinned, perforations may result or the tooth may be unnecessarily weakened when cleaned by such prior art methods.

FIGS. 27A–27J are transverse cross-sections of exemplary files that can be utilized to clean the operative middle portion, to improve the access to the apical root portion or to clean the apical root portion of the root canal. Each file has a different abrading portion. All of the files in combination with their respective abrading portions disclosed herein are examples of means for removing and cleaning of pulp material as the file instrument is operatively moved. Additionally, each abrading portion disclosed herein is an example of a means for abrading a root canal.

Conventional file designs can also be utilized within the scope of the present invention. Accordingly, the files are not limited to the designs shown in FIGS. 27A–27J. The files preferably, however, are configured in a manner such that when the potential for breakage is minimized. For example, a file with a square cross-section may be preferred over a triangular cross-section as the file with a square cross-section has a greater mass and is accordingly less likely to break. Additionally, a file configured with tines or extensions having wide angles are generally preferred over those with narrow angles. However, the preferred tine configuration depends primarily on the particular use as in some instances it is desirable to aggressively cut while in others the root can be passively cut. When it is more desirable to aggressively cut, it may be preferred for example to utilize a file with relatively narrow tines.

Figure 27A:
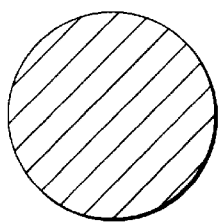
FIGS. 27A–J are transverse cross-sectional views of endodontic files.
Figure 27B:
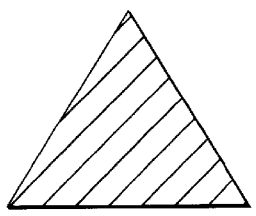
Figure 27C:
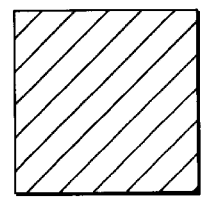
Figure 27D:
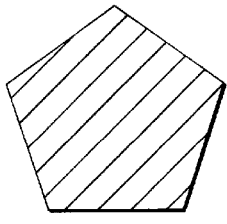
Figure 27E:
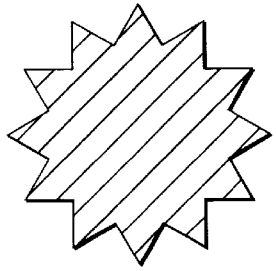
Figure 27F:
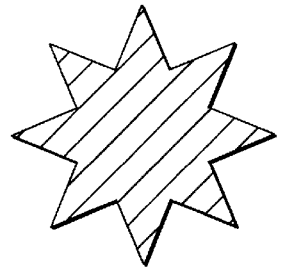
Figure 27G:
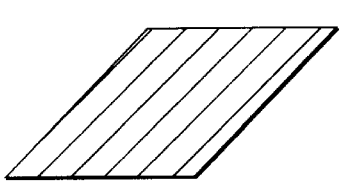
Figure 27H:
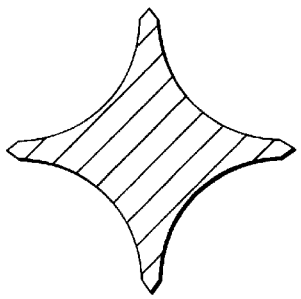
Figure 27I:
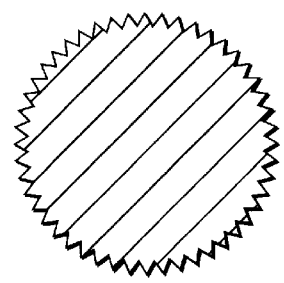
Figure 27J:
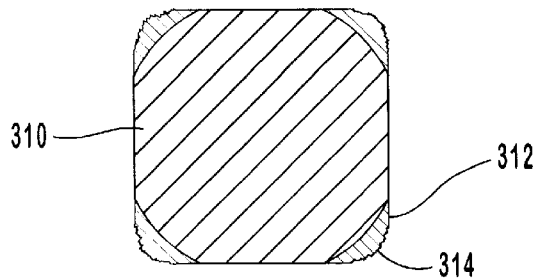

FIG. 27J depicts a file 310 with a generally square-shaped transverse cross-section and truncated corners 312. Abrasive grit 314 is located on truncated corners 312. Similarly such abrasive grit can be located around a file having any cross-sectional shape and be an effective abrading portion.

Figure 28:
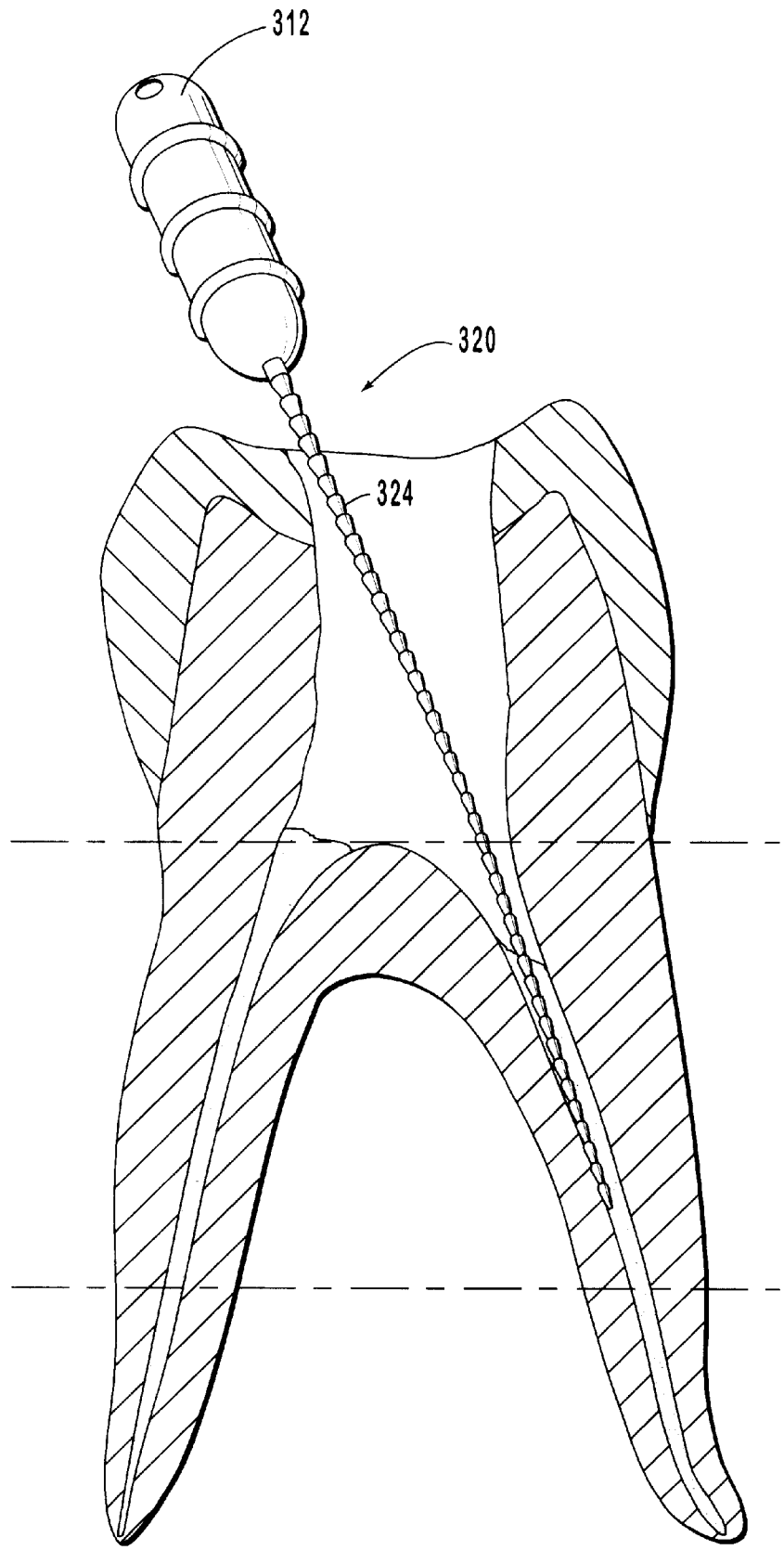
FIG. 28 is a longitudinal cross-sectional view of a tooth with a root canal being cleaned with a file instrument having a file formed by machining a groove into a metal blank.

The transverse cross-section of a file shown at FIG. 27A corresponds to a file as shown in FIG. 17A. In FIG. 28, a file instrument 320 is shown cleaning operative middle portion 160 of a root canal. Instrument 320 has a handle 322 connected to file 324 formed by machining a groove into a metal blank.

Figure 29:
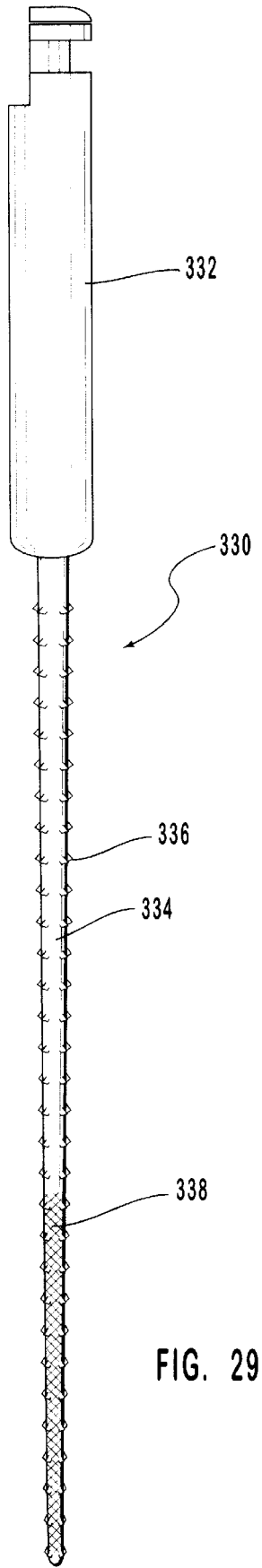
FIG. 29 is a perspective view of another embodiment of an endodontic instrument.
Figure 30:
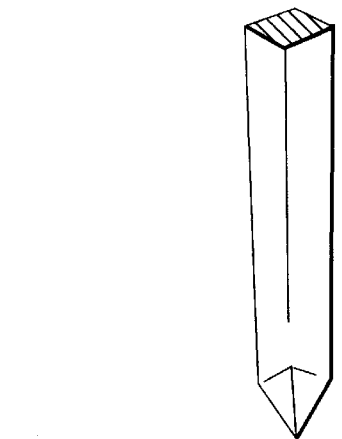
FIG. 30 is a partial perspective view of an endodontic file depicting the tip of the file.
Figure 31:
FIG. 31 is a partial perspective view of an endodontic file depicting the tip of the file.
Figure 32:
FIG. 32 is a partial perspective view of an endodontic file depicting the tip of the file.
Figure 33:
FIG. 33 is a partial perspective view of an endodontic file depicting the tip of the file.

FIG. 29 depicts another embodiment of a file instrument shown at 330. File instrument 330 has a handle 332 which is particularly adapted for use with a mechanical instrument. The file instruments of the present invention can, however, be utilized with any suitable handle configuration. All of the handles disclosed herein are examples of end means for grasping and operatively moving a file in an abrasive action.

File instrument 330 further comprises a file 334 which is preferably used to clean the operative middle portion. File 334 has an abrading portion comprising protrusions or barbs 336 at the upper end of the file and a combination of tines 336 and knurled surface 338 at the lower end. FIGS. 30–33 are depictions of various tips of files within the scope of the present invention.

EXAMPLES OF THE PREFERRED EMBODIMENTS

Testing was conducted to identify some of the anatomical characteristics of different teeth. The results of this testing are reported in Example 1. Additionally, Example 2 and Example 3 are hypothetical examples presented solely to illustrate some embodiments of the present invention. Note that reference is made in Example 2 to FIG. 35 and FIGS. 36A–D. The hypothetical examples are not to be construed as limiting the spirit and scope of the invention as these hypothetical examples were produced in furtherance of reducing the present invention to practice.

Example 1

Table 2 and Table 3 presented hereinbelow provide data regarding the anatomical characteristics of root canals of different teeth. More particularly, average measurements are provided of the canal diameters and the wall thicknesses of root canals at a location 2 mm from the apex of each root canal. A practioner should bear these average measurements in mind when widening the apical portion or cleaning the apical portion. Note that the roots of the first molars are referenced by their position with the abreviations m,v, d, and l for the terms mesial, vestibular, distal and lingual.

TABLE 2

Root Canal Anatomical Characteristics

| Maxillary Teeth | Number of Roots Examined | Distance From the Apex | Average Mesio-Distal Canal Diameter | Average Vestibulo-Distal Canal Diameter | Average Vestibular Wall Thickness | Average Lingual Wall Thickness | Average Mesial Wall Thickness | Average Distal Wall Thickness |
|---|---|---|---|---|---|---|---|---|
| Central Incisors | 20 | 2 mm | 0.39 mm | 0.38 mm | 0.93 mm | 1.12 mm | 0.91 mm | 1.05 mm |
| Lateral Incisors | 20 | 2 mm | 0.23 mm | 0.39 | 0.87 mm | 1.09 mm | 0.81 mm | 0.77 mm |
| First Premolars | 20 | 2 mm | 0.25 mm | 0.20 mm | 0.88 mm | 0.65 mm | 0.95 mm | 0.80 mm |
| Second Premolars | 20 | 2 mm | 0.27 mm | 0.23 mm | 1.16 mm | 0.99 mm | 0.99 mm | 0.86 mm |
| First Molar m-v Root | 25 | 2 mm | 0.18 mm | 0.32 mm | 1.04 mm | 1.07 mm | 0.73 mm | 0.82 mm |
| First Molar d-v Root | 25 | 2 mm | 0.21 mm | 0.23 mm | 0.87 mm | 0.81 mm | 0.89 mm | 0.85 mm |
| First Molar l Root | 25 | 2 mm | 0.23 mm | 0.22 mm | 0.68 mm | 0.85 mm | 0.85 mm | 1.03 mm |

TABLE 3

Root Canal Anatomical Characteristics

| Mandibular Teeth | Number of Roots Examined | Distance From the Apex | Average Mesio-Distal Canal Diameter | Average Vestibulo-Distal Canal Diameter | Average Vestibular Wall Thickness | Average Lingual Wall Thickness | Average Mesial Wall Thickness | Average Distal Wall Thickness |
|---|---|---|---|---|---|---|---|---|
| Central Incisors | 30 | 2 mm | 0.22 mm | 0.40 mm | 1.06 mm | 1.12 mm | 0.72 mm | 0.72 mm |
| Lateral Incisors | 25 | 2 mm | 0.22 mm | 0.28 mm | 0.76 mm | 0.71 mm | 0.73 mm | 0.67 mm |
| Canines | 30 | 2 mm | 0.29 mm | 0.36 mm | 0.95 mm | 0.10 mm | 0.71 mm | 0.77 mm |
| First Molar m Root | 30 | 2 mm | 0.39 mm | 0.38 mm | 1.21 mm | 1.25 mm | 0.94 mm | 0.94 mm |
| First Molar d Root | 30 | 2 mm | 0.23 mm | 0.54 mm | 1.23 mm | 1.28 mm | 0.87 mm | 0.92 mm |

Example 2

This example describes, in relation to FIG. 35 and FIGS. 36A–36D, an exemplary system and method for cleaning a root canal after the root canal has been properly accessed. After a tooth has been identified as requiring root canal therapy, an x-ray image is obtained in order to determine the state of health of a tooth as well as the structure and anatomical characteristics of the tooth. After all carious tissue has been removed and any old fillings have been infiltrated, a dam is installed.

Before the instruments designed for use in the operative middle portion or the apical portion of the root canal are utilized, the pulp chamber must be properly opened so that adequate access can be gained to the anatomical root canal. Access is gained by removing the top of the pulp chamber, preferably with an appropriate diamond bur instrument. The contents in the pulp chamber are then removed with the aid of appropriate irrigants. Examples of appropriate irrigants include hydrogen peroxide, primarily for use in the canals of living teeth, or sodium hypochlorite, primarily for the canals in necrotic teeth. If desired a cuspidectomy may be performed.

It is then preferable to remove or reduce dentinal or enamel protrusions or irregularities such as dentinal shelves, that may obscure or hinder access of instruments into the operative root canal by rectification of such protrusions with an appropriate instrument which preferably utilizes diamonds for abrasion. FIG. 36A depicts a tooth 540 before the removal of dentinal shelf 266 above root canal 252a. Dotted line 550 in FIG. 36A depicts the desired realignment through rectification in order to provide greater access for instrumentation during the subsequent phases. Rectified root canal 252a depicted in FIGS. 36B–D after subsequent phases shows that rectification would enable an instrument to be inserted in a relatively straight manner though the operative coronal portion 260 and the operative middle portion 262. Although, an instrument would need to flex within the apical portion 264 of root canal 252a due to its curvature, the required flexing is minimized as a result of the removal of dentinal shelf 266 above root canal 252a. Since the apical portion of root canal 252b is essentially straight, rectification of dentinal shelf 266 above root canal 252b would also enable an instrument to be inserted up to apex 254b through the apical portion 264 in an essentially straight configuration.

The progressive phases depicted in FIGS. 36A–D are similar to the phases shown in FIGS. 18, 19, 20, 25 and 26. For example. FIG. 36A depicts the same phase as is shown in FIG. 18. FIGS. 36A–D, however, better depict the changes of the shape of pulp canal 252a after each phase. The same numbers are used for the elements of tooth 540 as are used for tooth 240. Note that pulp material 250 is not shown in FIGS. 36A–D so that the changes to pulp canal 252a are clearly visible after each phase. As discussed hereinbelow. FIGS. 36B–D respectively depict root canal 252a of tooth 540 after cleaning operative coronal portion 262, after widening apical portion 264 and after cleaning apical portion 264.

After any necessary rectification, the working length is determined for the files used to clean the operative middle portion. The appropriate working length is determined by radiographically identifying the length of the operative root canal and then subtracting 3 mm from the length identified from the x-ray image. It is necessary to subtract 3 mm from the overall x-ray length in order to compensate for any distortions in the x-ray image and to avoid interfering with the apical portion while the operative middle portion is being prepared. After identifying the length of the root canal of a tooth and determining the working length of the files to be used, instruments can then be selected which have a length such that essentially all pulp material can be anatomically cleaned from the operative middle portion of a root canal without significantly removing pulp material from the apical root portion.

Figure 35:
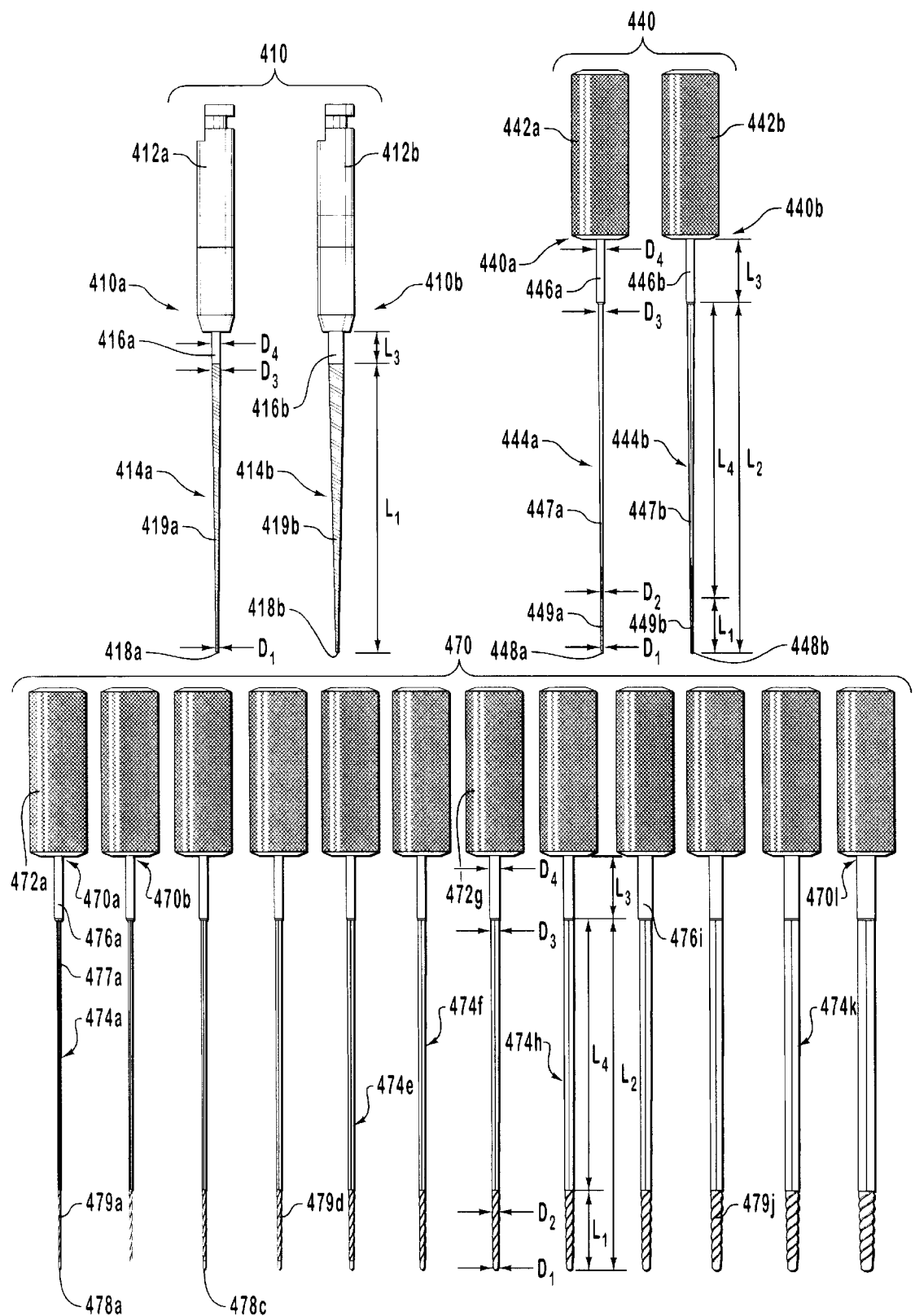
FIG. 35 is a view of a system of endodontic tools including a first set of instruments for cleaning the operative middle portion of an operative root canal, a second set of instruments for improving the access into the apical root portion and a third set of instruments for cleaning the apical root portion.

FIG. 35 depicts three sets of instruments identified at 410, 440 and 470 which are used to prepare a root canal. The sets of instruments identified respectively at 410, 440 and 470 are respectively used to clean the operative middle portion, to improve access into the apical portion and to clean the apical root portion.

Operative Middle Portion Phase and Related Sets of Instruments

Tables 4A, 4B and 4C presented hereinbelow describe the dimensions of three different set of instruments which can be used to clean the operative middle portion in different teeth depending on the particular operative root canal length. These three sets are preferably sold as part of a kit. Although, the kit includes several sets of instruments. Only one set of instruments is typically used for cleaning the operative middle portion. The practitioner selects from several sets in the kit depending on the particular length of the operative coronal portion and the operative middle portion. The instruments in Tables 4A, 4B and 4C have lengths which are respectively 16 mm, 17 mm and 20 mm.

In this example, the set of operative middle portion instruments selected for use in a tooth is the set presented in Table 4C due to the combined length of the operative coronal portion and the operative middle portion of the operative root canal. The set of instruments for cleaning the operative middle portion detailed in Table 4C corresponds with the set of instruments shown in FIG. 35 at 410. Since only one set of instruments is used to clean the operative middle portion only one set is shown in FIG. 35 at 410.

adjust the working length of file 414. Note that the file of each instrument detailed in Tables 4A, 4B and 4C has a 2 mm smooth portion or shank portion above the abrading portion. Handles 412a and 412b are respectively positioned on smooth shank portions 416a and 416b. These handles are configured for attachment to a handpiece. The sets of instruments presented in Table 4A and 4B have a similar appearance to set 410, however, the files of the instruments in Table 4B have an abrading portion configured to correspond with Hedstrom-type files.

The operative middle portion instruments in each set are formed from stainless steel. The instruments all have sufficient rigidity to apply pressure against root canal surfaces as each instrument is flexed or curved against root canal

TABLE 4A

Operative Middle Portion Instruments (16 mm)

| Instrument Number | Total Length of the File ($L_2 + L_3$) | Abrading Portion Length ($L_1$) | Shank Portion Length ($L_3$) | Tip Diameter ($D_1$) | Diameter at the top of the Abrading Portion ($D_3$) | Shank Portion Diameter ($D_4$) | Abrading Portion Taper |
|---|---|---|---|---|---|---|---|
| 1 | 16 mm | 14 mm | 2 mm | .10 mm | .38 mm | .50 mm | .02 |
| 2 | 16 mm | 14 mm | 2 mm | .13 mm | .69 mm | .70 mm | .04 |

TABLE 4B

Operative Middle Portion Instruments (17 mm)

| Instrument Number | Total Length of the File ($L_2 + L_3$) | Abrading Portion Length ($L_1$) | Shank Portion Length ($L_3$) | Tip Diameter ($D_1$) | Diameter at the top of the Abrading Portion ($D_3$) | Shank Portion Diameter ($D_4$) | Abrading Portion Taper |
|---|---|---|---|---|---|---|---|
| 1 | 17 mm | 15 mm | 2 mm | .10 mm | .40 mm | .50 mm | .02 |
| 2 | 17 mm | 15 mm | 2 mm | .10 mm | .70 mm | .70 mm | .04 |

TABLE 4C

Operative Middle Portion Instruments (20 mm)

| Instrument Number | Total Length of the File ($L_2 + L_3$) | Abrading Portion Length ($L_1$) | Shank Portion Length ($L_3$) | Tip Diameter ($D_1$) | Diameter at the top of the Abrading Portion ($D_3$) | Shank Portion Diameter ($D_4$) | Abrading Portion Taper |
|---|---|---|---|---|---|---|---|
| 1 | 20 mm | 18 mm | 2 mm | .10 mm | .46 mm | .50 mm | .02 |
| 2 | 20 mm | 18 mm | 2 mm | .13 mm | .85 mm | .90 mm | .04 |

As shown in Tables 4A, 4B and 4C, the operative middle portion instruments in the sets may have exactly the same tip diameters or tip diameters which are essentially the same. More particularly, the instruments in the set detailed in Table 4B both have a tip diameter of 0.10 mm while the instruments in the sets presented in Tables 4A and 4C have a tip diameter of either 0.10 mm or 0.13 mm. In each set, the second instrument has a greater taper than the file of the first instrument.

As indicated above, set 410 corresponds with the set presented in Table 4C. As shown, instruments 410a and 410b have files 414a and 414b. Each file has a shank portion 416 which tapers to an abrading portion 419 configured like conventional K-files and terminating at a tip 418. Smooth shank portion 416 may be used to accommodate stops to surfaces and simultaneously moved in a cleaning motion. Each instrument also has adequate resilience to avoid being substantially deformed as the instrument is flexed or curved to urge the abrading portion against root canal surfaces and as the instrument is simultaneously moved in a cleaning motion. Accordingly, a practitioner can move the instrument around the perimeter of the operative middle portion of the root canal using the contours of the operative middle portion as a guide for the movement of the instrument such that the original anatomy is enlarged and not significantly altered.

After set 410 as detailed in Table 4C is selected, the pulp chamber is flooded with an irrigation fluid or filled with a chelating lubricant gel, if the canal is atresic. The instruments in set 410 are then attached to a handpiece to move the instruments in either a rotating or reciprocating motion.

These instruments can also be manually moved. Instrument 410a and then 410b are then sequentially urged against the root canal for about one minute in conformance with the anatomy of the root canal. More particularly, the instruments are applied to the perimeter of the canal, acting on any protuberances or jagged edges in order to rectify the first two portions, the operative middle portion and the operative coronal portion, while still conforming to the anatomy of the canal.

After cleaning the operative middle portion, the root canal may appear as does root canal 252a of tooth 540 shown in FIG. 36B. FIG. 36B shows that dentinal shelf 266 has been fully rectified. The other contours of root canal 252a have been followed to clean operative middle portion 262 As a result, the diameter of the root canal in operative middle portion 262 has been widened, although, the original perimetrical anatomy has not been substantially altered, particuarly in the bottom half of the operative middle portion 262 of root canal 252a.

Apical Portion Widening Phase and Related Diets of Instruments

A probe is then inserted to the apex ot the root canal and another x-ray image is obtained. After the length has been determined, a set of instruments is selected for use in improving the access into the apical root portion or stated otherwise to enlarge the constricted region between the operative middle portion and the apical portion. This is achieved by manually moving one or more instruments until the transition zone between the operative middle portion and the apical root portion has been appropriately instrumented to have a diameter of about 0.40 mm, which is suitable for accommodating the diameters of the smallest irrigation needles.

Again the practitioner has a comprehensive kit with several sets of instruments which are designed for improving access into the apical root portion after the pulp material has been removed from the operative middle portion of a root canal. Each set is designed for use in a tooth with a different operative root canal length. Accordingly only one set from the kit is selected for use in operative root canal based on the length of the particular anatomical root canal being treated.

Tables 5A, 5B and 5C detail the dimensions of instruments with file lengths which are respectively 21 mm, 25 mm and 30 mm. In this example, the set presented in Table 5B is selected. The set presented in Table 5B is shown in FIG. 35 as set 440.

TABLE 5A

Apical Widening Instruments (21 mm)

| Inst. No. | Total Length of File $(L_1 + L_3 + L_4)$ | Abrad. Portion Length $(L_1)$ | Square Portion Length $(L_4)$ | Round Portion Length $(L_3)$ | Tip Diam $(D_1)$ | Abrad Portion Diam. $(D_2)$ | Square Portion Diam. $(D_3)$ | Shank Portion Diam. $(D_4)$ | Taper |
|---|---|---|---|---|---|---|---|---|---|
| 1 | 21 mm | 5 mm | 11 mm | 5 mm | .08 mm | .28 mm | .30 mm | .80 mm | .04 |
| 2 | 21 mm | 5 mm | 11 mm | 5 mm | .08 mm | .38 mm | .40 mm | 1.1 mm | .06 |

TABLE 5B

Apical Widening Instruments (25 mm)

| Inst. No. | Total Length of File $(L_1 + L_3 + L_4)$ | Abrad. Portion Length $(L_1)$ | Square Portion Length $(L_4)$ | Round Portion Length $(L_3)$ | Tip Diameter $(D_1)$ | Abrad Portion Diam. $(D_2)$ | Square Portion Diam. $(D_3)$ | Shank Portion Diam. $(D_4)$ | Taper |
|---|---|---|---|---|---|---|---|---|---|
| 1 | 25 mm | 5 mm | 15 mm | 5 mm | .08 mm | .28 mm | .30 mm | .90 mm | .04 |
| 2 | 25 mm | 5 mm | 15 mm | 5 mm | .08 mm | .38 mm | .40 mm | 1.3 mm | .06 |

TABLE 5C

Apical Widening Instruments (30 mm)

| Inst. No. | Total Length of File $(L_1 + L_3 + L_4)$ | Abrad. Portion Length $(L_1)$ | Square Portion Length $(L_4)$ | Round Portion Length $(L_3)$ | Tip Diameter $(D_1)$ | Abrad Portion Diam. $(D_2)$ | Square Portion Diam. $(D_3)$ | Shank Portion Diam. $(D_4)$ | Taper |
|---|---|---|---|---|---|---|---|---|---|
| 1 | 30 mm | 5 mm | 20 mm | 5 mm | .08 mm | .28 mm | .30 mm | 1.1 mm | .04 |
| 2 | 30 mm | 5 mm | 20 mm | 5 mm | .08 mm | .38 mm | .40 mm | 1.6 mm | .06 |

The files of the instruments in the sets detailed in Tables 5A, 5B and 5C are formed from stainless steel. Each file has three sections including a smooth shank portio, a square portion and an abrading portion. As indicated above, the set presented in Table 5B corresponds with set 440 shown in FIG. 35. Note, however, with the exception of length, the instruments detailed in Table 5A and Table 5C would appear just like set 440. Instrument 440a has a file 444a with smooth shank portion 446a, a square portion 447a, an abrading portion 449a and a file tip 448a. As shown, the smooth shank portion 446a is the top section of file 444a and a handle 442 is positioned on shank portion 446a. Smooth shank portion 446a tapers to square portion 447a which is between shank portion 446a and abrading portion 449a.

The smooth shank portion enables stops be positioned on the file to adjust the working length of the file. Each smooth shank portion of each file has a length of about 5 mm with various diameters. The instruments can be used for all operative lengths that are likely to be encountered in clinical practice through the positioning of the stops at the predetermined lengths. While the instruments can be offered in a more expanded series of millimetrically different lengths, the use of stops is acceptable, particularly sincen these instruments are manually moved.

In each set, the diameter at the top of the square portion of instrument number 1 and instrument number 2 is respectively 0.30 mm and 0.40 mm. The abrading portion is formed by twisting the square section so that the abrading portion has a K-file configuration. The instruments in each set all have the same tip diameters. The taper of the files from the tip ($D_1$) to the diameter at the top of the square portion ($D_3$) remains constant and is respectively 0.04 and 0.06 for instrument number 1 and instrument number 2 in each set.

Preferably, instrument 1 is first utilized and then instrument 2 to obtain, in a gradual manner, the desired enlargement of the specific transition zone between the operative middle portion and the apical portion. This enlargement is also preferably achieved without significantly changing the diameter of the apical portion of the canal. Accordingly, the tip diameter ($D_1$) of the various instruments in this set remains constant while the diameter at the top of the cutting area or abrading portion ($D_2$), located 5 mm from the tip, is graduated from one instrument to the next, reaching a maximum diameter of 0.38 mm. The rest of the shaft, up to the handle, does not have a cutting surface. To the extent that these instruments are used to expand the apical portion of the canal, the practitioner should constantly bear in mind the average diameters of the canals and the average thicknesses of the parietal walls at the apex, as listed in Table 2 and Table 3.

After widening the apical portion of the root canal with the set shown at 440 in FIG. 35 and as detailed in Table 5B. the root canal may appear as does root canal 252a in FIG. 36C with a widened apical portion 264. More particuarly, the region of root canal 252a extending from the bottom of operative middle portion 262 to the top half of apical portion 264 has been noticeably widened. The bottom half of apical portion 264 has also been widened but to a much lesser degree.

Apical Portion Cleaning Phase and Related Sets of Instruments

After the access into the apical portion has been adequately widened as discussed hereinabove and as shown in FIG. 36C, the apical portion is cleaned. Cleaning is halted at the working length as determined by the operator which should be at the apex. The practitioner should determine this length beforehand based on the biological condition of the apico-periapical region, in terms of the morphometrics of the diameters and thicknesses at the apex as set forth in the Table 2 and Table 3, and in accordance with the amount of widening to be applied to the apical portion of the canal.

Again sets of instruments are provided with each set having a different length. Three sets of instruments are described hereinbelow which are designed for removing and cleaning essentially all pulp material from the apical root portion after access into the apical root portion has been improved by a set of instruments such as set 440 detailed in Table 5B. In some instances, the instruments described in this example can also be used to clean the pulp material from the root canal immediately after the operative middle portion has been cleaned by a set of instruments such as the sets presented in Table 4C.

Tables 6A, 6B and 6C detail the dimensions of instruments with file lengths which are respectively 21 mm, 25 mm and 30 mm. However please note that only instruments from Table 6B are used in the tooth being cleaned in this example. The set of instruments detailed in Table 6B are shown in FIG. 35 as set 470. Set 470 includes instruments 470a–l which respectively correspond with instruments 1–12 in the set presented in Table 6B.

The instruments in set 470 have a similar appearance as the instruments in set 440. Instruments 470a–l have a handle 472 opposite a file 474. Each file 474 has a smooth shank portion 476a, a square portion 477, an abrading portion 479 and a file tip 478. The sets of instruments presented in Table 6A and 6C have a similar appearance to instruments detailed in Table 6B and shown at 470. however, the files have different lengths. The taper of the files from the tip ($D_1$) to the diameter at the top of the square portion ($D_3$) is provided in each table.

TABLE 6A

Apical Cleaning Instruments (25 mm)

| Inst. No. | Total Length of File ($L_1 + L_3 + L_4$) | Abrad. Portion Length ($L_1$) | Square Portion Length ($L_4$) | Round Portion Length ($L_3$) | Tip Diameter ($D_1$) | Abrad Portion Diam. ($D_2$) | Square Portion Diam. ($D_3$) | Shank Portion Diam. ($D_4$) | Taper |
|---|---|---|---|---|---|---|---|---|---|
| 1 | 21 mm | 5 mm | 11 mm | 5 mm | .10 mm | .20 mm | .42 mm | .50 mm | 0.02 |
| 2 | 21 mm | 5 mm | 11 mm | 5 mm | .15 mm | .25 mm | .47 mm | .50 mm | 0.02 |
| 3 | 21 mm | 5 mm | 11 mm | 5 mm | .20 mm | .30 mm | .52 mm | .60 mm | 0.02 |
| 4 | 21 mm | 5 mm | 11 mm | 5 mm | .25 mm | .375 mm | .65 mm | .70 mm | 0.025 |
| 5 | 21 mm | 5 mm | 11 mm | 5 mm | .30 mm | .425 mm | .70 mm | .70 mm | 0.025 |
| 6 | 21 mm | 5 mm | 11 mm | 5 mm | .35 mm | .475 mm | .75 mm | .80 mm | 0.025 |
| 7 | 21 mm | 5 mm | 11 mm | 5 mm | .40 mm | .525 mm | .80 mm | .80 mm | 0.025 |
| 8 | 21 mm | 5 mm | 11 mm | 5 mm | .50 mm | .625 mm | .90 mm | .90 mm | 0.025 |
| 9 | 21 mm | 5 mm | 11 mm | 5 mm | .60 mm | .725 mm | 1.0 mm | 1.0 mm | 0.025 |
| 10 | 21 mm | 5 mm | 11 mm | 5 mm | .70 mm | .825 mm | 1.1 mm | 1.1 mm | 0.025 |
| 11 | 21 mm | 5 mm | 11 mm | 5 mm | .80 mm | .925 mm | 1.2 mm | 1.2 mm | 0.025 |
| 12 | 21 mm | 5 mm | 11 mm | 5 mm | 1.0 mm | 1.125 mm | 1.4 mm | 1.5 mm | 0.025 |

TABLE 6B

Apical Cleaning Instruments (25 mm)

| Inst. No. | Total Length of File ($L_1 + L_3 + L_4$) | Abrad. Portion Length ($L_1$) | Square Portion Length ($L_4$) | Round Portion Length ($L_3$) | Tip Diameter ($D_1$) | Abrad Portion Diam. ($D_2$) | Square Portion Diam. ($D_3$) | Shank Portion Diam. ($D_4$) | Taper |
|---|---|---|---|---|---|---|---|---|---|
| 1 | 25 mm | 5 mm | 15 mm | 5 mm | .10 mm | .20 mm | .50 mm | .50 mm | 0.02 |
| 2 | 25 mm | 5 mm | 15 mm | 5 mm | .15 mm | .25 mm | .55 mm | .60 mm | 0.02 |
| 3 | 25 mm | 5 mm | 15 mm | 5 mm | .20 mm | .30 mm | .60 mm | .60 mm | 0.02 |
| 4 | 25 mm | 5 mm | 15 mm | 5 mm | .25 mm | .375 mm | .75 mm | .80 mm | 0.025 |
| 5 | 25 mm | 5 mm | 15 mm | 5 mm | .30 mm | .425 mm | .80 mm | .80 mm | 0.025 |
| 6 | 25 mm | 5 mm | 15 mm | 5 mm | .35 mm | .475 mm | .85 mm | .90 mm | 0.025 |
| 7 | 25 mm | 5 mm | 15 mm | 5 mm | .40 mm | .525 mm | .90 mm | .90 mm | 0.025 |
| 8 | 25 mm | 5 mm | 15 mm | 5 mm | .50 mm | .625 mm | 1.0 mm | 1.0 mm | 0.025 |
| 9 | 25 mm | 5 mm | 15 mm | 5 mm | .60 mm | .725 mm | 1.1 mm | 1.1 mm | 0.025 |
| 10 | 25 mm | 5 mm | 15 mm | 5 mm | .70 mm | .825 mm | 1.2 mm | 1.2 mm | 0.025 |
| 11 | 25 mm | 5 mm | 15 mm | 5 mm | .80 mm | .925 mm | 1.3 mm | 1.3 mm | 0.025 |
| 12 | 25 mm | 5 mm | 15 mm | 5 mm | 1.0 mm | 1.125 mm | 1.5 mm | 1.5 mm | 0.025 |

TABLE 6C

Apical Cleaning Instruments (30 mm)

| Inst. No. | Total Length of File ($L_1 + L_3 + L_4$) | Abrad. Portion Length ($L_1$) | Square Portion Length ($L_4$) | Round Portion Length ($L_3$) | Tip Diameter ($D_1$) | Abrad Portion Diam. ($D_2$) | Square Portion Diam. ($D_3$) | Shank Portion Diam. ($D_4$) | Taper |
|---|---|---|---|---|---|---|---|---|---|
| 1 | 30 mm | 5 mm | 20 mm | 5 mm | .10 mm | .20 mm | .60 mm | .60 mm | 0.02 |
| 2 | 30 mm | 5 mm | 20 mm | 5 mm | .15 mm | .25 mm | .65 mm | .70 mm | 0.02 |
| 3 | 30 mm | 5 mm | 20 mm | 5 mm | .20 mm | .30 mm | .70 mm | .70 mm | 0.02 |
| 4 | 30 mm | 5 mm | 20 mm | 5 mm | .25 mm | .375 mm | .875 mm | .90 mm | 0.025 |
| 5 | 30 mm | 5 mm | 20 mm | 5 mm | .30 mm | .425 mm | .925 mm | 1.0 mm | 0.025 |
| 6 | 30 mm | 5 mm | 20 mm | 5 mm | .35 mm | .475 mm | .975 mm | 1.0 mm | 0.025 |
| 7 | 30 mm | 5 mm | 20 mm | 5 mm | .40 mm | .525 mm | 1.025 mm | 1.1 mm | 0.025 |
| 8 | 30 mm | 5 mm | 20 mm | 5 mm | .50 mm | .625 mm | 1.125 mm | 1.2 mm | 0.025 |
| 9 | 30 mm | 5 mm | 20 mm | 5 mm | .60 mm | .725 mm | 1.225 mm | 1.3 mm | 0.025 |

TABLE 6C-continued

Apical Cleaning Instruments (30 mm)

| Inst. No. | Total Length of File $(L_1 + L_3 + L_4)$ | Abrad. Portion Length $(L_1)$ | Square Portion Length $(L_4)$ | Round Portion Length $(L_3)$ | Tip Diameter $(D_1)$ | Abrad Portion Diam. $(D_2)$ | Square Portion Diam. $(D_3)$ | Shank Portion Diam. $(D_4)$ | Taper |
|---|---|---|---|---|---|---|---|---|---|
| 10 | 30 mm | 5 mm | 20 mm | 5 mm | .70 mm | .825 mm | 1.325 mm | 1.4 mm | 0.025 |
| 11 | 30 mm | 5 mm | 20 mm | 5 mm | .80 mm | .925 mm | 1.425 mm | 1.5 mm | 0.025 |
| 12 | 30 mm | 5 mm | 20 mm | 5 mm | 1.0 mm | 1.125 mm | 1.625 mm | 1.7 mm | 0.025 |

After the apical portion has been properly widened, the practitioner selects a set of files having the appropriate length, such as one of the sets presented in Tables 6A, 6B or 6C. To ensure that the files have an appropriate working length, it may be necessary to place stops around the shank portions of the files identified for example at 416a, 446a and 476a. The practitioner then selects an instrument from the set identifed as having an appropriate length for introduction into the root canal down to the apical portion.

As indicated above, in this example, an instrument is selected from the set detailed in Table 6B, which is shown in FIG. 35 as set 470. After selecting an instrument, the practitioner then determines, based on feel and experience, whether the file is appropriately sized or whether a larger or smaller file is needed. For instance, if the practitioner selects instrument number 2 from the set detailed in Table 6B and shown in FIG. 35 at 470b which has a tip diameter of 0.15 mm and the file binds after insertion, then the practitioner would switch to instrument number 1 which has a tip diameter of 0.10 mm. Similarly, if instrument number 2 is too loose then the practitioner would then switch to instrument number 3 which has a tip diameter of 0.20 mm. The practitioner then uses that appropriately sized instrument to clean the apical portion of the root canal by hand. If the practitioner concludes after using an appropriately sized file, that further instrumentation is still needed within the apical portion then the instrument with the next largest file may be used. It is typically unnecessary to use a third instrument with an even larger file after using a series of two instruments. However, the practitioner may clean the apical root portion with a series of more than two instruments as deemed necessary by the practitioner in order to fully clean the apical portion.

After the apical portion of the root canal has been cleaned with the set shown at 470 in FIG. 35 and as detailed in Table 6B. the root canal may appear as does root canal 252a shown in FIG. 36D with a cleaned apical portion 264. More particularly, after use of an instrument such as instrument 2 from Table 6B shown at 470b, apical portion 264 may appear as shown. Note that cleaning apical portion 264 has substantially widened the bottom half of apical portion 264 while the top half is less significantly flared when compared to its appearance before being cleaned. The appearance of apical portion 264 results from the different configurations of the respective abrading portions of instruments used to widen and to clean the apical portion. More particularly, the diameter of the tip $(D_1)$ and the diameter at the top of the abrading portion $(D_2)$ of the last instrument used to widen the apical portion, instrument 440b, are respectively 0.08 mm and 0.38 mm while instrument 470b has a tip diameter $(D_1)$ of 0.15 mm and the diameter at the top of the abrading portion $(D_2)$ is 0.25 mm. Stated otherwise, the 0.06 taper of abrading portion 449b results in much greater flaring than the 0.02 taper of abrading portion 479b while the large tip diameter of instrument 440b causes the widening of the lower half of apical portion 264.

Set 410 and set 440 are preferably disposed after use. However, since only one or two instruments from set 470 are used, it is preferable to replace or clean the instruments used from set 470. All of the sets of instruments described in this example may be sold together as a comprehensive kit or various sets may be grouped together as kits intended for use with teeth of particular lengths. For example, the sets used in the tooth cleaned in this example which are detailed in Table 4C, 5B and 6B may be sold together. Additionally, since set 410 and set 440 are intended to be single use sets these sets may also be sold together as a single use disposable kit.

Example 3

This example describes another exemplary system for cleaning a root canal after the root canal has been properly accessed.

Operative Middle Portion Instruments

The sets of instruments designed for use in the operative middle portion of a root canal are set in Tables 7A, 7B and 7C. In contrast to the sets of operative middle portion instruments described in Example 2, each of these sets include four instruments instead of only two instruments. The lengths of the files in these sets include the various lengths that are likely to be encountered in clinical practice which range predominantely but not exclusively from 15 mm to 20 mm. Longer lengths, 25 mm, are typically needed for the middle segment of canine teeth. Accordingly, the files in each set of instruments have the following respective lengths: 17 mm, 20 mm and 25 mm. The lengths of the instruments in these three sets encompass the average variations in length that are likely to be encountered in clinical practice and in terms of the overall length of the operative coronal portion and the operative middle portion of various operative canals. However, please note that other sets may also be useful as these three sets are merely illustrative. For example, it may be useful to have a greater series of sets with lengths ranging from 15 mm to 20 mm in 1 mm increments and an additional set having a length of 25 mm.

As in Example 2, one set of instruments is selected based on the length of the tooth. Accordingly, after the length of the operative middle portion has been determined then either the set of instruments detailed in Table 7A, 7B or 7C is selected and if necessary stops may be utilized to adjust the working length of the file. When the length of the operative middle portion has been appropriately determined, each of these sets of instruments can be used to anatomically clean essentially all pulp material from the operative middle portion of a root canal without significantly removing pulp material from the apical root portion.

TABLE 7A

Operative Middle Portion Instruments (17 mm)

| Instrument Number | Total Length of the File | Abrading Portion | Tip Diameter ($D_1$) | Diameter at top of the Abrading Portion ($D_2$) |
|---|---|---|---|---|
| 1 | 17 mm | 17 mm | .10 mm | .40 mm |
| 2 | 17 mm | 17 mm | .13 mm | .50 mm |
| 3 | 17 mm | 17 mm | .13 mm | .70 mm |
| 4 | 17 mm | 17 mm | .13 mm | .90 mm |

TABLE 7B

Operative Middle Portion Instruments (21 mm)

| Instrument number | Total Length of the File | Abrading Portion | Tip Diameter ($D_1$) | Diameter at top of the Abrading Portion ($D_2$) |
|---|---|---|---|---|
| 1 | 20 mm | 20 mm | .10 mm | .45 mm |
| 2 | 20 mm | 20 mm | .13 mm | .55 mm |
| 3 | 20 mm | 20 mm | .13 mm | .75 mm |
| 4 | 20 mm | 20 mm | .13 mm | .95 mm |

TABLE 7C

Operative Middle Portion Instruments (25 mm)

| Instrument number | Total Length of the File | Abrading Portion | Tip Diameter ($D_1$) | Diameter at top of the Abrading Portion ($D_2$) |
|---|---|---|---|---|
| 1 | 25 mm | 25 mm | .10 mm | .55 mm |
| 2 | 25 mm | 25 mm | .10 mm | .65 mm |
| 3 | 25 mm | 25 mm | .13 mm | .75 mm |
| 4 | 25 mm | 25 mm | .13 mm | .95 mm |

The instruments in the sets detailed in Table 7A and Table 7B include a first instrument with a tip diameter of about 0.10 mm while the other instruments have a tip diameter of about 0.13 mm. The first and second instruments in the set presented in Table 7C have tip diameters of about 0.10 mm while the third and fourth instruments have tip diameters of about 0.13 mm. It is often useful to begin instrumenting with a slightly smaller tip diameter, however, the difference in diameter is so small that these tip diameters are considered to be essentially the same size. The difference is particularly insignificant when compared with the incremental increase in the size of the diameter tip from instrument to instrument of conventional instruments used in conventional cleaning techniques.

The sets of instruments described in this example would be expected to require more time to use than the instruments described in Example 2 as there are more instruments in each set. However, all of the sets can be used to clean the operative middle portion without substantially changing the original anatomy of the root canal. More particularly, each instrument is configured to enable a practitioner to move the file along a side of the operative middle portion in a manner such that the original anatomy is enlarged without being modified to have just the shape of the instrument.

Note that the abrading portion ot each file extends along the entire length of each file. Accordingly, each file is capable o simultaneously abrading both the operative coronal portion and the operative middle portion. In any event, the abrading portion extends beyond the conventional 16 mm length of instruments in present use.

Since sets are provided in different lengths it is not necessary to use stops to adjust the length of the file as the handle of the instrument ensures that the instrument stops safely at the proper working depth. Thus, the use of sets of instruments with graduated lengths eliminates the problems associated with traditional stopping depths. More particularly, the sets reduce the amount of time required to position the instruments at the desired length and eliminate the risk of bacterial contamination of the instruments due to handling.

Apical Portion Widening Instruments

The access into the apical portion is improved after the operative middle portion has been cleaned. More particularly, it is necessary to widen the access into the apical root portion of the root canal in order to enable irrigants to be delivered as needed. The dimensions of a set of instruments which can be used for this purpose are set forth in Table 5. The files of each instrument have a length of about 35 mm and an abrading portion which is about 5 mm long.

TABLE 8

Apical Widening Instruments (35 mm)

| Instrument Number | Total Length of the File ($L_1 + L_3 + L_4$) | Abrading Portion Length ($L_1$) | Tip Diameter ($D_1$) | Diameter the top of the Abrading Portion ($D_2$) | Taper |
|---|---|---|---|---|---|
| 1 | 35 mm | 5 mm | .08 mm | .20 mm | .020 |
| 2 | 35 mm | 5 mm | .08 mm | .25 mm | .020 |
| 3 | 35 mm | 5 mm | .08 mm | .30 mm | .036 |
| 4 | 35 mm | 5 m | .08 mm | .35 mm | .045 |

The instruments would each be expected to be useful for improving access into the apical root portion after the pulp material has been removed from the operative middle portion of a root canal. However, such a set of instruments would be expected to require more time to use than one of the sets of instruments described in Example 2 as there are more instruments in this set.

Apical Portion Cleaning Instruments

After the access into the apical portion has been adequately widened, the apical portion is cleaned. One of the sets of instruments detailed in Tables 6A, 6B or 6C may be used to clean the apical portion or alternatively the set detailed in Table 9 may be used. Each instrument in the set described in Table 9 has a file with a working length of about 35 mm and an abrading portion which is about 5 mm long. The files of the instruments all have the same tip diameters and have increasing larger tapers.

TABLE 9

| Instrument Number | Total Length of the File ($L_1 + L_3 + L_4$) | Abrading Portion Length ($L_1$) | Tip Diameter ($D_1$) | Diameter at the top of the Abrading Portion ($D_2$) | Taper |
|---|---|---|---|---|---|
| 1 | 35 mm | 5 mm | .06 mm | .18 mm | .02 |
| 2 | 35 mm | 5 mm | .08 mm | .20 mm | .02 |
| 3 | 35 mm | 5 mm | .10 mm | .22 mm | .02 |
| 4 | 35 mm | 5 mm | .15 mm | .27 mm | .02 |
| 5 | 35 mm | 5 mm | .20 mm | .32 mm | .02 |
| 6 | 35 mm | 5 mm | .25 mm | .37 mm | .02 |
| 7 | 35 mm | 5 mm | .30 mm | .42 mm | .02 |

TABLE 9-continued

| Instrument Number | Total Length of the File ($L_1 + L_3 + L_4$) | Abrading Portion Length ($L_1$) | Tip Diameter ($D_1$) | Diameter at the top of the Abrading Portion ($D_2$) | Taper |
|---|---|---|---|---|---|
| 8 | 35 mm | 5 mm | .35 mm | .47 mm | .02 |
| 9 | 35 mm | 5 mm | .40 mm | .52 mm | .02 |

The set of instruments detailed in Table 9 have longer files than the sets provided in Tables 6A, 6B and 6C so more stops would be necessary. In most other respects the set in Table 9 is very similar to the other sets discussed in Example 2 for cleaning the apical portion. Note, however, that the set in Table 9 begins with smaller tip diameters which may be useful in some instances.

The present invention may be embodied in other specific forms without departing from its spirit or essential characteristics. The described embodiments are to be considered in all respects only as illustrated and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A method for anatomical removal and cleaning of essentially all pulp material from the operative coronal portion, the operative middle portion and the apical root portion of an operative root canal in a tooth, the method comprising:

exposing the root canal by removing a portion of the tooth at a crown thereof and by removing the top of the pulp chamber;

removing and cleaning essentially all pulp material from the operative coronal portion and the operative middle portion without significantly removing pulp material from the apical root portion by flexibly moving an instrument within the operative middle portion in a cleaning motion in conformance with the anatomical shape of the operative middle portion; and improving access into the apical root portion after the pulp material has been essentially removed from the operative middle portion; and removing and cleaning essentially all remaining pulp material from the apical root portion after access into the apical root portion has been improved.

2. A method as recited in claim 1, wherein the step of removing and cleaning essentially all pulp material from the operative middle portion comprises flexing the instrument against the root canal surfaces such that pressure is applied against the root canal surfaces.

3. A method as defined in claim 1, wherein the step of removing and cleaning essentially all pulp material from the operative middle portion comprises flexing the instrument against root canal surfaces such that pressure is applied against the root canal surfaces without substantially deforming the instrument.

4. A method as defined in claim 1, wherein the step of removing and cleaning essentially all pulp material from the operative middle portion comprises moving the instrument around the perimeter of the operative middle portion of the root canal.

5. A method as defined in claim 1, wherein the step of removing and cleaning essentially all pulp material from the operative middle portion comprises moving the instrument along a side of the operative middle portion of the root canal such that the instrument generally has more than one center of motion during the step of removing and cleaning essentially all pulp material from the operative middle portion.

6. A method as defined in claim 1, wherein the step of removing and cleaning essentially all pulp material from the operative middle portion comprises moving the instrument within the operative middle portion in a manner such that contours of the operative middle portion are used as a guide for the movement of the instrument.

7. A method as defined in claim 1, wherein the instrument comprises at least a file having a length that limits the penetration of the file in the root canal to essentially only the operative middle portion of the root canal in accordance with a determination of a suitable working length in the operative root canal.

8. A method as defined in claim 1, wherein the instrument comprises a file opposite an end means for grasping and operatively moving the file in an abrasive action, and wherein the end means is configured for positioning on the occlusal surface of a tooth to serve as a stop.

9. A method as defined in claim 1, wherein the step of improving access into the apical root portion comprises widening the apical root portion such that irrigants can be delivered into the apical portion of the operative root canal from an irrigation needle.

10. A method as defined in claim 1, wherein the step of improving access into the apical root portion comprises widening the apical root portion such that the apical root portion has a diameter up to about 0.40 mm.

11. A method as defined in claim 1, further comprising the step of determing the length of the operative middle portion before removing and cleaning essentially all pulp material from the operative middle portion by identifying the length of the operative middle portion from a radiographic image of the operative root canal.

12. A method as defined in claim 1, further comprising the step of minimizing obstructions in the operative root canal before removing and cleaning essentially all pulp material from the operative middle portion such that instruments can be inserted in the operative middle portion in a relatively straight manner.

13. A method as defined in claim 1, further comprising the step of irrigating the operative root canal with an irrigant.

14. A method for anatomical removal and cleaning of essentially all pulp material from the operative coronal portion, the operative middle portion and the apical root portion of an operative root canal in a tooth, the method comprising:

exposing the root canal by removing a portion of the tooth at a crown thereof and by removing the top of the pulp chamber;

removing and cleaning essentially all pulp material from the operative coronal portion and the operative middle portion without significantly removing pulp material from the apical portion by sequentially introducing instruments from a set of first endodontic instruments into the operative middle portion and then flexibly urging each instrument against operative middle portion surfaces while simultaneously moving each instrument in a cleaning motion that confirms to the anatomical shape of the operative middle portion;

improving access into the apical root portion with instruments from a set of second endodontic instruments after the pulp material has been essentially removed from the operative middle portion by the set of first endodontic instruments; and removing and cleaning essentially all remaining pulp material from the apical root portion with instruments from a set of third endodontic instruments after access into the apical root portion has been improved by the set of second endodontic instruments.

15. A method as recited in claim 14, wherein the step of removing and cleaning essentially all pulp material from the operative middle portion comprises flexing each instrument in the set of first endodontic instruments against root canal surfaces such that pressure is applied against the root canal surfaces.

16. A method as recited in claim 14, wherein the step of removing and cleaning essentially all pulp material from the operative middle portion comprises flexing each instrument in the set of first endodontic instruments against root canal surfaces such that pressure is applied against the root canal surfaces without substantially deforming the instrument.

17. A method as defined in claim 14, wherein the step of removing and cleaning essentially all pulp material from the operative middle portion comprises moving each instrument in the set of first endodontic instruments around the perimeter of the operative middle portion of the root canal.

18. A method as defined in claim 14, wherein the step of removing and cleaning essentially all pulp material from the operative middle portion comprises moving each instrument in the set of first endodontic instruments along a side of the operative middle portion of the root canal such that the instrument generally has more than one center of motion during the step of removing and cleaning essentially all pulp material from the operative middle portion.

19. A method as defined in claim 14, wherein the step of removing and cleaning essentially all pulp material from the operative middle portion comprises moving each instrument in the set of first endodontic instruments within the operative middle portion in a manner such that contours of the operative middle portion are used as a guide for the movement of the instrument.

20. A method as defined in claim 14, wherein the step of removing and cleaning essentially all pulp material from the operative middle portion comprises moving each instrument in the set of first endodontic instruments around the perimeter of the operative middle portion of the root canal.

21. A method as defined in claim 14, wherein each instrument in the set of first endodontic instruments comprises at least a file, and wherein each file of each respective instrument has a length that limits the penetration of the file in the root canal to essentially only the operative middle portion of the root canal.

22. A method as defined in claim 14, wherein each instrument in the set of first endodontic instruments comprises at least a file, and wherein each file of each instrument in the set of first endodontic instruments has essentially the same length.

23. A method as defined in claim 14, wherein each instrument in the set of first endodontic instruments comprises at least a file having a tip opposite a top end, and wherein the files of all of the instruments in the set of first endodontic instruments have essentially the same tip diameter while having distinct top end diameters to enable the files to be sequentially introduced into the operative middle portion such that each successive file has a greater top end diameter than that of the preceding file.

24. A method as defined in claim 14, wherein each instrument in the set of first endodontic instruments comprises at least a file having a tip opposite a top end, and wherein the files of all of the instruments in the set of first endodontic instruments have distinct tapers to enable the files to be sequentially introduced into the operative middle portion such that each successive file has a greater taper than that of the preceding file.

25. A method as defined in claim 14, wherein the instrument comprises a file opposite an end means for grasping and operatively moving the file in an abrasive action, and wherein the end means is configured for positioning on the occlusal surface of a tooth to serve as a stop.

26. A method as defined in claim 14, wherein the step of improving access into the apical root portion comprises widening the apical root portion such that irrigants can be delivered into the apical portion of the operative root canal from an appropriately sized irrigation needle.

27. A method as defined in claim 14, wherein the step of improving access into the apical root portion comprises widening at least an upper segment of the apical root portion such that at least the upper segment of the apical root portion has a diameter up to about 0.40 mm.

28. A method as defined in claim 14, further comprising the step of determining the length of the operative middle portion before removing and cleaning essentially all pulp material from the operative middle portion by identifying the length of the operative middle portion from a radiographic image of the operative root canal.

29. A method as defined in claim 14, further comprising the step of minimizing obstructions in the operative root canal before removing and cleaning essentially all pulp material from the operative middle portion such that instruments can be inserted in the operative middle portion in a relatively straight manner.

30. A method as defined in claim 14, further comprising the step of irrigating the operative root canal with an irrigant.

31. A method for anatomical removal and cleaning of essentially all pulp material from the operative middle portion and the apical root portion of an operative root canal in a tooth, the method comprising:

exposing the root canal by removing a portion of the tooth at a crown thereof and by removing the top of the pulp chamber;

removing and cleaning essentially all pulp material from the operative coronal portion and the operative middle portion without significantly removing pulp material from the apical root portion with instruments from a set of first endodontic instruments, wherein each instrument comprises a file having a tip opposite a top end that extends from an end means for grasping and operatively moving the file, by sequentially introducing the instruments into the operative middle portion such that each successive file has a greater top end diameter than that of the preceding file and then flexibly urging each instrument against operative middle portion surfaces while simultaneously moving each instrument in a cleaning motion without substantially altering the anatomical shape of the operative middle portion; and improving access into the apical root portion with instruments from a set of second endodontic instruments after the pulp material has been essentially removed from the operative middle portion by the set of first endodontic instruments; and removing and cleaning essentially all remaining pulp material from the apical root portion with instruments from a set of third endodontic instruments after access into the apical root portion has been improved by the set of second endodontic instruments.

32. A method as recited in claim 31, wherein the step of removing and cleaning essentially all pulp material from the operative middle portion comprises flexing each instrument in the set of first endodontic instruments against root canal surfaces such that pressure is applied against the root canal surfaces.

33. A method as recited in claim 31 wherein the step of removing and cleaning essentially all pulp material from the operative middle portion comprises flexing each instrument in the set of first endodontic instruments against root canal surfaces such that pressure is applied against the root canal surfaces without substantially deforming the instrument.

34. A method as defined in claim 31, wherein the step of removing and cleaning essentially all pulp material from the operative middle portion comprises moving each instrument in the set of first endodontic instruments around the perimeter of the operative middle portion of the root canal.

35. A method as defined in claim 31, wherein the step of removing and cleaning essentially all pulp material from the operative middle portion comprises moving each instrument in the set of first endodontic instruments along a side of the operative middle portion of the root canal such that the instrument generally has more than one center of motion during the step of removing and cleaning essentially all pulp material from the operative middle portion.

36. A method as defined in claim 31, wherein the step of removing and cleaning essentially all pulp material from the operative middle portion comprises moving each instrument in the set of first endodontic instruments within the operative middle portion in a manner such that contours of the operative middle portion are used as a guide for the movement of the instrument.

37. A method as defined in claim 31, wherein the step of removing and cleaning essentially all pulp material from the operative middle portion comprises moving each instrument in the set of first endodontic instruments around the perimeter of the operative middle portion of the root canal.

38. A method as defined in claim 31, wherein each instrument in the set of first endodontic instruments comprises at least a file, and wherein each file of each respective instrument has a length that limits the penetration of the file in the root canal to essentially only the operative middle portion of the root canal.

39. A method as defined in claim 31, wherein each instrument in the set of first endodontic instruments comprises at least a file, and wherein each file of each instrument in the set of first endodontic instruments has essentially the same length.

40. A method as defined in claim 31, wherein the files of all of the instruments in the set of first endodontic instruments have essentially the same tip diameter.

41. A method as defined in claim 31, wherein the files of all of the instruments in the set of first endodontic instruments have distinct tapers to enable the files to be sequentially introduced into the operative middle portion such that each successive file has a greater taper than that of the preceding file.

42. A method as defined in claim 31, wherein the end means of each instrument in the set of first endodontic instruments is connected to the top end of the file such that movement of the end means also moves at least the top end of the file along a common axis with the end means.

43. A method as defined in claim 31, wherein the end means of each instrument in the set of first endodontic instruments is configured for positioning on the occlusal surface of a tooth to serve as a stop.

44. A method as defined in claim 31, wherein the step of improving access into the apical root portion comprises widening the apical root portion such that irritants can be delivered into the apical portion of the operative root canal from an irrigation needle.

45. A method as defined in claim 31, wherein the step of improving access into the apical root portion comprises widening the apical root portion such that the apical root portion has a diameter up to about 0.40 mm.

46. A method as defined in claim 31, further comprising the step of determining the length of the operative middle portion before removing and cleaning essentially all pulp material from the operative middle portion by identifying the length of the operative middle portion from a radiographic image of the operative root canal.

47. A method as defined in claim 31, further comprising the step of minimizing obstructions in the operative root canal before removing and cleaning essentially all pulp material from the operative middle portion such such that instruments can be inserted in the operative middle portion in a relatively straight manner.

48. A method as defined in claim 31, further comprising the step of irrigating the operative root canal with an irrigant.

* * * * *

UNITED STATES PATENT AND TRADEMARK OFFICE
CERTIFICATE OF CORRECTION

PATENT NO. : 6,059,572
DATED : May 9, 2000
INVENTOR(S) : Francesco Riitano

It is certified that error appears in the above-identified patent and that said Letters Patent are hereby corrected as shown below:

Col. 2, ln. 5: after "generally" change "show" to --shows--

Col. 2, ln. 5: after "teeth" insert --10--

Col. 3, ln. 3: after "through a" change "stud" to --study--

Col. 3, ln. 34: after "a" change "practitioners" to --practitioner--

Col. 6, ln. 17: after "the" change "crows" to --crown--

Col. 7, ln. 29: after "completeness" change "effected" to --affected--

Col. 11, ln. 28: after "a" change "big(ger" to --bigger--

Col. 11, ln. 34: after "biggest" change "tile" to --file--

Col. 12, ln. 8: after "flies" change "costs" to --cost--

Col. 15, ln. 44: after "may" and before "desirable" insert --may--

Col. 16, ln. 34: after "two" change "portion" to --portions--

Col. 17, ln. 38: before "operative" insert --The--

Col. 19, ln. 40: after "cleaned" change "lith" to --with--

Col. 20, ln. 38: after "view" change "ot" to --of--

UNITED STATES PATENT AND TRADEMARK OFFICE
CERTIFICATE OF CORRECTION

PATENT NO. : 6,059,572
DATED : May 9, 2000
INVENTOR(S) : Francesco Riitano

It is certified that error appears in the above-identified patent and that said Letters Patent are hereby corrected as shown below:

Col. 22, ln. 59: after "a" change "lout" to --low--

Col. 23, ln. 23: after "dentists" change "man" to --may--

Col. 23, ln. 49: after "and" and before "easy" delete |24|

Col. 24, ln. 16: after "0.15" change "m" to --mm--

Col. 24, ln. 33: after "16A" change "are" to ---is--

Col. 24, ln. 64: change "properly," to --properly--

Col. 24, ln. 65: change "rectify," to --rectify--

Col. 26, ln. 20: after "have" change "files" to --file--

Col. 26, ln. 29: after "FIG." change "1 9 A" to --19A--

Col. 27, ln. 4: after "process," change "or" to --for--

Col. 32, ln. 49: after "about" change "0.4" to --1.4--

Col. 32, ln. 66: after "the" change "tile" to --file--

Col. 35, ln. 40: after "truncated" change "comers" to --corners--

Col. 36, ln. 40: after "A" change "practioner" to --practitioner--

UNITED STATES PATENT AND TRADEMARK OFFICE
CERTIFICATE OF CORRECTION

PATENT NO. : 6,059,572

DATED : May 9, 2000

INVENTOR(S) : Francesco Riitano

It is certified that error appears in the above-identified patent and that said Letters Patent is hereby corrected as shown below:

Col. 36, Table 2 Heading: "Lateral Incisors" after "0.39" insert --mm--

Col. 38, ln. 66: after "of" change "instruments. Only" --instruments, only--

Col. 41, ln. 22: after "Related" change "Diets" to --Sets--

Col. 43, ln. 3: after "shank" change "portio" to --portion--

Col. 43, ln. 23: after "particularly" change "sincen" to --since--

Col. 49, ln. 67: after "capable" change "o" to --of--

Col. 50, ln. 35: after "5" change "m" to --mm--

Col. 51, ln. 48: after "improved" insert --by the second endodontic instrument means.--

Col. 52, ln. 32: after "of" change "determing" to --determining--

Col. 54, ln. 19: after "of" change "determing" to --determining--

UNITED STATES PATENT AND TRADEMARK OFFICE
CERTIFICATE OF CORRECTION

PATENT NO. : 6,059,572

DATED : May 9, 2000

INVENTOR(S) : Francesco Riitano

It is certified that error appears in the above-identified patent and that said Letters Patent is hereby corrected as shown below:

Col. 56, ln. 22: after "that" change "irritants" to --irrigants--

Col. 56, ln. 30: after "of" change "determing" to --determining--

Col. 56, ln. 38: after "portion" and before "such" delete [such]

Signed and Sealed this

Fifteenth Day of May, 2001

Attest:

NICHOLAS P. GODICI

*Attesting Officer*   *Acting Director of the United States Patent and Trademark Office*